United States Patent [19]
Tischfield et al.

[11] Patent Number: 5,972,677
[45] Date of Patent: *Oct. 26, 1999

[54] MAMMALIAN PHOSPHOLIPASE $A_2$ NUCLEOTIDE SEQUENCES LOW MOLECULAR WEIGHT AMINO ACID SEQUENCES ENCODED THEREBY ANTISENSE SEQUENCES AND NUCLEOTIDE SEQUENCES HAVING INTERNAL RIBOSOME BINDING SITES

[75] Inventors: Jay A. Tischfield, Carmel, Ind.; Jeffrey J. Seilhamer, Los Altos Hills, Calif.

[73] Assignees: J. Tischfield; Incyte Pharmaceuticals, Inc.

[ * ] Notice: This patent issued on a continued prosecution application filed under 37 CFR 1.53(d), and is subject to the twenty year patent term provisions of 35 U.S.C. 154(a)(2).

[21] Appl. No.: 08/888,497
[22] Filed: Jul. 7, 1997

Related U.S. Application Data

[63] Continuation of application No. 08/651,405, May 22, 1996, abandoned, which is a continuation of application No. 08/097,354, Jul. 26, 1993, abandoned.

[51] Int. Cl.⁶ .............................. C12N 9/20; C12N 15/55
[52] U.S. Cl. ............................ 435/198; 536/23.2
[58] Field of Search ............................ 435/198; 536/23.2

[56] References Cited

U.S. PATENT DOCUMENTS 5,019,508  5/1991  Johnson et al. ......................... 435/198

OTHER PUBLICATIONS

Westermann, et al., "Inhibition of expression of SV40 virus large T–antigen by antisense oligodeoxyribonucleotides," Biomed. Biochim. Acta 48 (1989) 1, 85–93.

Seilhamer, et al., "Novel Gene Exon Homologous to Pancreatic Phospholipase $A_2$: Sequence and Chromosomal Mapping of Both Human Genes," Journal of Cellular Biochemistry 39:327–337 (1989).

Macejak, et al., "Internal initiation of translation mediated by the 5'leader of a cellular mRNA," Nature. vol. 353, Sep. 5, 1991, 90–94.

Young, et al., "Utilization of an Epstein–Barr virus replicon as a eukaryotic expression vector," Gene, 62 (Feb. 1988) 171–185.

Bekkers, et al, "The use of genetic engineering to obtain efficient production of porcine pancreatic phospholipase $A_2$ by *Saccharomyces cerevisiae*," Biochimica et Biophisica Acta, 1089 (1991) 345–351.

Deng, et al, "A novel expression vector for high–level synthesis and secretion of foreign proteins in *Escherichia coli*: overproduction of bovine pancreatic phospholipase $A_2$," Gene 93 (1990) 229–234.

J.J. Seilhamer et al. "Novel Gene Exon Homologous to . . . " J. Cell. Biochem. 39:327–337 (1989).

R.L. Heinrikson "Dissection and Sequence Analysis . . . " Meth. in Enzymology 197:201–214 (1991).

Davidson, et al., Evolutionary Relationships and Implications for the Regulation of Phospholipase $A_2$ from Snake Venom to Human Secreted Forms, *J. Mol. Evol* (1990) 31:228–238.

*Primary Examiner*—Rebecca E. Prouty
*Attorney, Agent, or Firm*—Jenkins & Gilchrist, A Professional Corporation

[57] ABSTRACT

Novel mammalian phospholipase ($PLA_2$) nucleotide sequences and low molecular weight (about 14KD) amino acid sequences encoded thereby are disclosed. More particularly, a cloned human $HPLA_2$ cDNA expressing $HPLA_2$-10 and its cloned rat $RPLA_2$ cDNA counterpart, expressing $RPLA_2$-10, which are characterized as $PLA_2$ Type IV, are disclosed. A second type of $PLA_2$ cDNA, characterized as $PLA_2$ Type III and exemplified by a rat $PLA_2$ cDNA encoding $RPLA_2$-8 and a partial human $PLA_2$ nucleotide sequence encoding $HPLA_2$-8, is disclosed. Expression of the cDNAs encode the two new types of $PLA_2$ enzymes which have phospholipase activity. The novel $PLA_2$s do not include disulfide bridges between cysteine amino acids 11 and 77 or elapid loops. However, the novel $PLA_2$s may include amino acid COOH-terminal extensions which can vary in length. Seventeen of the eighteen absolutely conserved amino acids in all active 14KD $PLA_2$s are believed to be conserved in $RPLA_2$-8 and $HPLA_2$-8, whereas all eighteen are believed to be conserved in $RPLA_2$-10 and $HPLA_2$-10. Because the encoded sequences of $RPLA_2$-8 and $HPLA_2$-8 include only 16 cysteine amino acids, they have been designated as Type III. $RPLA_2$-10 and $HPLA_2$-10 are designated as Type IV since their encoded sequences include only 12 cysteine amino acids.

38 Claims, 47 Drawing Sheets

RPLA2-8 cDNA Structure

▨ Represents 121 bp repeat sequence  ■ Represents RPLA2-8 open reading frame.

RPLA2-8 cDNA Secondary Structure

Fig. 3A

```
          10        20        30        40        50        60
GAATTCCGCCTCCACCTCTCAAATGCTGGGATTGCAGGATGTCCCCCCACCCCTGCTCCC
clone linker
          70        80        90       100       110       120
TTGTGTCCTTGCTTCCTGCTGCCGGAATGTATCACTTAATTGCCAGGTACCCATGGTCTG
            Pla8-8 (primer)
         130       140       150       160       170       180
ATTCCAGGATAGAAGGGCGGGCGAGGGGGTTGGAGGAGAGGCCTCTATTATTTCCGCGGT 190       200       210       220       230       240
CTGGCAGGCCTGGAAGCAAAGCTTCAAGTGCAGAAGGAGGAGTGTCGGGGAATGGCAGAA
            Pla8-7 (primer)
         250       260       270       280       290       300
AAGGCTGGAACAGCAATGCAGACCTAGGTAAAGGGCACAGAGCTGAGGGAAGCTCCTGGG 310       320       330       340       350       360
AGGCTCCCTGCAGCTCCTGCCTCTGCACATGACCCGGACTCCTTTTCTCTCTTTGGATCT 370       380       390       400       410       420
GCGTCCAGGGACTGGCTTGTACACACCCCTCCCAGGAGACCCCTTGGCAGCTGCACACTC 430       440       450       460       470       480
AGGCTCCATCCAAGTTGGCTCTGCCCCTGGGGAAGGCTGCTCAAAAGGCCTGGCTCCCAG 490       500       510       520       530       540
TTTCTGGGGACCCACAGAGAGCCTCTCACCTCGCAGCTCAGCTCCATCCGCCTCCTGTGC 550       560       570       580       590       600
CTGGCTGCGACCAGCTGGGTCTAACTATAGACAGTCAGCAACTTCAGCCACTTCACCGAG 610       620       630       640       650       660
TTTCCCAACAGCTTTGAGATTTGGAAGCCGGAAGCCTGACTGCCTTCTCAGAAGCTACGG 670       680       690       700       710       720
TCCACTACCTCAGCCATTCTGTTGGAGCTGAACTGGCAGATGAAGGTGAGACCCAGGCAC 730       740       750       760       770       780
CATGGACCTCCTGGTCTCCTCAGGAATGAAGGGCATCGCTGTCTTCCTTGTCTTTATCTT
 MetAspLeuLeuValSerSerGlyMetLysGlyIleAlaValPheLeuValPheIlePh
 Rclo8-5' (primer)
         790       800       810       820       830       840
CTGCTGGACAACCTCCACCCTCAGCAGCTTCTGGCAGTTCCAGAGGATGGTCAAACACAT
 eCysTrpThrThrSerThrLeuSerSerPheTrpGlnPheGlnArgMetValLysHisIl
                                   Pla8-1 (primer)
         850       860       870       880       890       900
CACGGGGCGCAGCGCCTTCTTCTCCTATTACGGATATGGCTGCTACTGTGGGCTTGGGG
 eThrGlyArgSerAlaPhePheSerTyrTyrGlyTyrGlyCysTyrCysGlyLeuGlyGl 910       920       930       940       950       960
CCGAGGGATCCCTGTGGACGCCACAGACAGGTGCTGCTGGGCTCATGACTGTTGCTACCA
 yArgGlyIleProValAspAlaThrAspArgCysCysTrpAlaHisAspCysCysTyrHi
```

Fig. 3B

```
Pla8-2 (primer)
       970       980       990      1000      1010      1020
CAAGCTTAAGGAATATGGCTGCCAGCCCATCTTGAATGCCTATCAGTTTGCCATTGTCAA
sLysLeuLysGluTyrGlyCysGlnProIleLeuAsnAlaTyrGlnPheAlaIleValAs 1030      1040      1050      1060      1070      1080
CGGGACCGTGACCTGTGGATGCACCATGGGTGGCGGCTGCTTGTGCGGGCAGAAAGCCTG
nGlyThrValThrCysGlyCysThrMetGlyGlyGlyCysLeuCysGlyGlnLysAlaCy 1090      1100      1110      1120      1130      1140
TGAGTGTGACAAACTGTCTGTGTACTGCTTCAAGGAGAACCTGGCCACCTACGAGAAAAC
sGluCysAspLysLeuSerValTyrCysPheLysGluAsnLeuAlaThrTyrGluLysTh 1150      1160      1170      1180      1190      1200
TTTCAAGCAGCTCTTCCCCACCAGGCCCCAGTGTGGCAGGGACAAACTCCATTGCTAGGC
rPheLysGlnLeuPheProThrArgProGlnCysGlyArgAspLysLeuHisCysEnd
                                              Rclo8-3' (primer)
      1210      1220      1230      1240      1250      1260

1270      1280      1290      1300      1310      1320
CTTCCCCTCCAAGAGTCCCCAGGCTCCTGCAGCTCAGCCTTGCTGTCTAGGGAGTGTCTT 1330      1340      1350      1360      1370      1380
CTCAGGCATTAGGGGACCGGAGGTGGAGAATTCCTGCCCTGGAATCAGACCATGGGTACC 1390      1400      1410      1420      1430      1440
TGGCAATTAAGTGATACATTCCGGCAGCAGGAAGCAAGGACACAAGGGAGCAGGGGTGGG 1450      1460      1470      1480      1490      1500
GGGACATCCTGCAATCCCAGCATTTGAGAGGTGGAGGCAAGAGGTGGGGGGTAGCCTCCA 1510      1520      1530      1540      1550      1560
CTATACGGTAAGTTCAAGGCTAACCTGAGCTACCTGAGACCTTGCCTTGAAAAAACTTTT 1570      1580      1590      1600      1610      1620
TTAAAAAACGTTTAAAGGAAAAGAAAACAGAAAGACACGGGACTGGGCTGAAAGGTACT 1630      1640      1650      1660      1670      1680
CTCAAACCGATTTCCCAGGAAGAGCGGAGAGCCCCAGGTTCAGCTCCAGCCTGAACTCCC 1690      1700      1710      1720      1730      1740
CCATACCCTCAGTCCTGGTCAGGATGTGTGTCTGACTGGGGAACCAAGTCCTCCACCCGG 1750      1760      1770      1780      1790      1800
GTGGAGCTTAGCTGGGAACTACGCAGGTGTCCTAGAAAATACAGTCCTAAGAGCCTCACC 1810      1820      1830      1840      1850      1860
CGGAGTCTCATCCCCATTTGCTCCAGGACTGACCTCTGTAAATCTTCCAGCAGGAAGCAG 1870      1880      1890      1900      1910      1920
GCTGTACCCATCTCAGGAGGTGGGGTGCTGTTAGAACAATGGTGTGCACCAGTGACACAA 1930      1940      1950      1960      1970      1980
```

Fig. 3C

```
AGATGTCATGGTTAAGATGGCATCAAGAAGTGGAAAGGACATTCGGAACAGTGGGTCCAA
     1990      2000      2010      2020      2030      2040
GGCACCCAAAGTCCTCACCCCAATTTAGAAGCCGTTGGTCCTGTAAGACTTAAATCTACT
     2050      2060      2070      2080      2090      2100
AAACAAGGAAGGTCTAACTGGGCTGGAATCTGAAGTTCATGGTGCCAGGCTGGGGCGGTG
     2110      2120      2130      2140      2150      2160
GGTGGGGACGTGGCCGTGGCCATGACCATGATTGCCTCTCTGCATGGTGACACTTGCCTT
     2170      2180      2190      2200      2210      2220
TTGCACCCTAGCTCTCAGCACATCTGAAAAGGACAGACTCTCCTGTTCATTCCTTGAATC
     2230      2240      2250      2260      2270      2280
TGAGACTCTCCTCACTAATGTAGCAAAAATGGAGGTCTAAAGTGCAGGCTTCAGCCTCTG
     2290      2300      2310      2320      2330      2340
AGGTCCAGGGCAGGAGGAAGCTGGGGCTCAGCCTCCTGGAGGATGAGAGCTTGCCGGGTG
     2350      2360      2370      2380      2390      2400
AGCATCAGCGACAGCAGACCCTTGGGCTCAGAGAGTCCGCAAGCCTGGGAGAGCCTGGCC
     2410      2420      2430      2440      2450      2460
GAGCCCTGACTGCAGCACACAGAGCCGTGAGCCTCATACAAGAAGCCACATTTTGGGGAA
     2470      2480      2490      2500      2510      2520
GCTTCAGGGTGGCTGATTCCACAGCTGTTGGGTTCAGAACGGAAGCCGGGAGCACTCACT
     2530      2540      2550      2560      2570      2580
TCAGATATGGAAGCTTTGTTTTACGAGCGCTTAGCACCAGTTCAGGATCTGAACTTCGTC
     2590      2600      2610      2620      2630      2640
CTGACCGGAGAGTCCGTACCACATTTTTATAGGATGGGAACACAGAGCGAGGGGCGTGGA
     2650      2660      2670      2680      2690      2700
GTAAGCTGTTGAACGACCGATCATATTTTGACCTAAGAGGTTAAGTAAGGACGTTAACAT
     2710      2720      2730      2740      2750      2760
GGGTGACTGGGCATTAGTCAGGTCACCTGGTTTTGGGGTCTTTGAATCAGCTTTCGTGGC
     2770      2780      2790      2800      2810      2820
CAGGTCCCTTCCTGGACTTTGGCTCGGAATTTAGAACGATAAGGGAACGAAGAGGTGGGC
     2830      2840      2850      2860      2870      2880
AAGCTTCGGGCAGTCAGTAAGAGGCAGCACATTCATGACCTGTGTGCCTTGTTTAGATAA
     2890      2900      2910      2920      2930      2940
TGGGATAAGAGTATCTCCTCTCTTACACCCCTTACTGGTTAACAGACAAACACGAGACAT
     2950      2960      2970      2980      2990      3000
CTGAAGAAGCAGGACAGGAGTTAGGTTCTGGGGCACAGGAACATGAACTCGGTTTTGATC
     3010      3020      3030      3040      3050      3060
```

Fig. 3D

```
CTGCCGGCAAGGTGGATCTTGTTCCTGAGAAGGCTGGACTCAGGAAACTTCCTCTTAACA
     3070      3080      3090      3100      3110      3120
AGTTAGTTGATGGCGCTGGTCCTTAGTCACCGATACTGTCAGGCTCTCAGCTCTTGGGCC
     3130      3140      3150      3160      3170      3180
AGACTTGGCGGCCATGGGAGTGTGGTCACTTGCCCCGTCCCCTTCTTCCAGGAGGTACTG
     3190      3200      3210      3220      3230      3240
GGGAAAATGGTTGGATTTGTGGAGTTGTAGGGAACACTCATGGCTCCCTTCACTTAGTAG
     3250      3260      3270      3280      3290      3300
GTCAGCTAACATATGTGTATCGAGCCCATACCGTGTGCCATGTGCAGTGCTGAGCAGCAG
     3310      3320      3330      3340      3350      3360
GGAGTCAGAGATTTAAAGACACACACACAGACTTCAAGTCTGAGAATTTTGAATCCCAGG
     3370      3380      3390      3400      3410      3420
GAGAACCGCTGAGAGCCATGGCGCTTCTACCAATGCCAGAGGCTAACACCCGGACTGAGA
     3430      3440      3450      3460      3470      3480
AAACTAAGCACGAGGAGACAGCAGGGTCAGCAGAGGGCCTGGGAGCTAGGGCCCTGAGCA
     3490      3500      3510      3520      3530      3540
GTACCTAGTTCAAATCACAGAGTCGTCTTTCTTCCTCCACCCTACCCAGGTACAGCAAGT
     3550      3560      3570      3580      3590      3600
AGACACGGGTGGGGGCAGGGCAGGGATGCAGGAACATTAGGGCACACCGATGTGGCTAGG
     3610      3620      3630      3640      3650      3660
CTAAGCTAGAGCATGTTACCTTCTCAGGGGTCCTGTCATGTCAGAGACTGGTTCCAACCT
     3670      3680      3690      3700      3710      3720
GGAAAGATGTCTGAGTGACAGCTGTGGTAGAAGAAGAGAGGCCAGGGTGATATCAGCATG
     3730      3740      3750      3760      3770      3780
AAGGGCTGGATTGCTATGTGAGATCCAGATCTCTTCTGCCACTGGGGTCAGCTTCTACAC
     3790      3800      3810      3820      3830      3840
TGGAAATAGATGGGCTGCGTTATGGAGGGTGGTGTGAGTCCCTGTCTGCGTTGTGCCGGG
     3850      3860      3870      3880      3890      3900
AATCAGAGCAGAGTGTTAGCGCTGTAAAAGGACATGCTGGTGCTTGCAGGAAATCATCGA
     3910      3920      3930      3940      3950      3960
TTTCTTGGAAGGGCAGCCATTCATCTACACCAGGGATTGACTTTATGCCAGGCTTGTGAT
     3970      3980      3990      4000      4010      4020
GAGGGTAGAAAAGTAGAAATTCTGTCCGCTGCAAGGAGCAGTCAGAGGACACAAGGACCA
     4030      4040      4050      4060      4070      4080
AATAGCTTGGGAGTTGCGGAAGTAGGTGTCTGCTGAGGGAGCAGTGACCACTGGGGGAAA
     4090      4100      4110      4120      4130      4140
```

Fig. 3E

```
GGCTCCTTCAAGGAATTCAGGGACAGGGGTGAGGGCTGACATCTTGCCTGAGACCCTAAA
        4150      4160      4170      4180      4190      4200
GAAGAGAAGGAGTTGAGAGGGCTGAGTATGCTGTGTGGAGCCCCACCCCCACCCCCACCC
        4210      4220      4230      4240      4250      4260
CCACCCCCACCCCAGGTATATGGATGGAGGATAATGCGGGGGTCGGGTTCCTCTCAAATC
        4270      4280      4290      4300      4310      4320
CATCATCCCACCTTCGAGCTGCTGGCACGGCCTTGCCAGCACAGCCCGATTCTGTGTTGA
        4330      4340      4350      4360      4370      4380
CAAAATACTCGAACGAAATGATTACATGCAAATAAAATGCAAGAGGAAAAATCTAAACGG
                                Polyadenylation site AATTC
clone linker
```

Fig. 5

```
400  ACCTCAGACCCCCTGGTCTCCTCAGGAATGAAGGTCATTGCCATCCTCACCCTCCTC
     |||  ||| ||||||||||||||||||||||||  ||  ||  ||  ||  ||  ||
719  ACCATGGACCTCCTGGTCTCCTCAGGAATGAAGGGCATCGCTGTCTTCCTTGTCTTTATC

460  TTCTGCT
     |||||||
779  TTCTGCT
```

Matches = 51      Mismatches = 16      Unmatched = 0
Length = 67       Matches/length = 76.1 percent Top strand is HPLA2-8 exon I sequence; bottom is RPLA2-8 exon I sequence.
The underlined ATG is the putative RPLA2-8 translation start codon.

---

Top strand is SEQ ID NO: 23:;

Bottom is SEQ ID NO: 24:.

Fig. 6

```
2633 tgg TGGCAGCCCCCACCCACAGCAGCAGTTTCTGGCAGTTTCAGAGAGGGTCAAACACATCACGG
         ||| |||||| ||||| |||||| ||||||||||||| ||||||||||||| ||||||||||
 786 cag GGACAACCTCCACCCCTCAGCAGCTTCTGGCAGTTCCAGAGGATGGTCAAACACATCACGG 2693 GGCGAAGTGCCTTCTTCTCTCATATTACGGATATGGCTGCTACTGTGGGCTTGGGGATAAAG
     |||||| ||||| ||| ||||| ||||||||| ||||||||||||||||||| |||| ||
 846 GGCGCAGCGCCTTCTTCTCCTATTACGGATATGGCTGCTACTGTGGGCTTGGGCTTGGGGGCCCGAG 2753 GGATCCCCGTGGATGACACTGACAG gtg
     |||||| |||| ||| || ||||| |||
 906 GGATCCCCGTGTGGACGCCACAGACAG gtg Matches    = 126    Mismatches = 19    Unmatched = 0
Length     = 145    Matches/length = 86.9 percent Top strand is HPLA2-8 coding exon II sequence; bottom strand is RPLA2-8
exon II sequence Top strand is SEQ ID NO: 25:;

Bottom strand is SEQ ID NO: 26:.
```

Fig. 7

```
13862 tag GTGGATGCACCCTTGGTCTCCTGGTGCCAGCTGCCACTGCCAGGCTGAAGGCCTGTGAGTGT
          ||||||| ||  |||             ||| ||||   || ||| ||||||||||||||
1034  cag GTGGATGCA CCATG             GGTGGGGGCTGTGTGCGGGCAGAAAGCCTGTGAGTGT 13921 GACAAGCAATCCGTGTGCACTGCTTCAAAGAGAGCCTGCCACCTATGAGAAAACTTCAAG
      ||||   ||| |||||||||||||||| ||||||  || |||||| |||||||||||||
1088  GACAAACTGTCTGTGTACTGCTTCAAGGAGAACTGGCCACCTACGAGAAACTTTCAAG 13981 CAG    TTCTCCAGCCGGCCCAGGTGTGGCAGACATAAGCCCTGGTGCTAG
      |||    |||||| |||  ||||  |||||||||| | | |||  |||||||
1148  CAGCTCTTCCCCACCAGGCCCCAGTGTGGCAGGACAAACTCCATTGCTAG Matches   = 128     Mismatches = 33     Unmatched = 9
Length    = 170     Matches/length = 75.3 percent
```

Top strand is SEQ ID NO: 27:;

Bottom strand is SEQ ID NO: 28:.

Fig. 8

```
 1    MetAspLeuLeuValSerSerGlyMetLysGlyIleAlaValPheLeuValPheIlePhe
      |   |  |    :         :      :          :  :             |
 1    MetLysLeuLeuLeuAlaAlaLeu       LeuThrAla    GlyVal    Thr

21    CysTrpThrThrSerThrLeuSerSerPheTrpGlnPheGlnArgMetValLys   His
          :          |  |         |  |       :     |   |
16    AlaHisSerIleSerThrArgAlaVal    TrpGlnPheArgAsnMetIleLysCysThr

40    IleThrGlyArgSerAlaPhePheSerTyrTyrGlyTyrGlyCysTyrCysGlyLeuGly
      |  |           |                   |  |   |  |  |   |  |  |
35    IleProGlySerAspProLeuArgGluTyrAsnAsnTyrGlyCysTyrCysGlyLeuGly

60    GlyArgGlyIleProValAspAlaThrAspArgCysCysTrpAlaHisAspCysCysTyr
      |     |  |  |  |              |  |  |           |  |  |  |
55    GlySerGlyThrProValAspAspLeuAspArgCysCysGlnThrHisAspHisCysTyr

80    HisLysLeuLysGluTyrGly   CysGlnProIleLeu    AsnAlaTyr    Gln
         |     |     |        |              :  :  |   |    :
75    AsnGlnAlaLysLysLeuGluSerCysLysPheLeuIleAspAsnProTyrThrAsnThr

96    PheAla   IleValAsnGlyThrValThrCysGlyCysThrMetGlyGlyGlyCysLeu
      :   :                          |  |  |           :
95    TyrSerTyrLysCysSerGlyAsnValIleThr   CysSerAspLysAsnAsnAsp

115   CysGlyGlnLysAlaCysGluCysAspLysLeuSerValTyrCysPheLysGluAsnLeu
      |      |     |  |    |  |    :     :        |  |           :
113   CysGluSerPheIleCysAsnCysAspArgGlnAlaAlaIleCysPhe   SerLysVal

135   AlaThrTyrGluLysThrPheLysGlnLeuPheProThrArgProGlnCysGlyArgAsp
      |     |         :  |      |             |    :
132   Pro   TyrAsnLysGluTyrLysAspLeu      AspThrLys

155   LysLeuHisCys
      |     |   |
144   Lys   HisCys
```

Matches = 56    Mismatches = 84    Unmatched = 24
Length = 164    Matches/length = 34.1 percent Top line is RPLA2-8 deduced amino acid sequence; bottom line is rat type I PLA2 amino acid sequence. a vertical line indicates a match, : a conservative substitution, and no symbols a mismatch.

Fig. 9

```
  1      MetAspLeuLeuValSerSerGlyMetLysGlyIleAlaValPheLeuValPheIlePhe
         |  |    :  |    :              :  |  |        :    :        |
  1      MetLysValLeuLeu     Leu        LeuAlaVal      ValIleMetAlaPhe

21      CysTrpThrThrSerThrLeuSerSerPheTrpGlnPheGlnArgMetValLysHisIle
                        :         |         |         |  |         :
 15      Gly   SerIleGlnValGlnGlySerLeuLeuGluPheGlyGlnMetIleLeuPheLys

41      ThrGly  ArgSerAlaPhePheSerTyr    TyrGlyTyrGlyCysTyrCysGlyLeu
         |  |    |  |    |    :           |  |    :     |  |  |  |  :
 34      ThrGlyLysArgAlaAspVal   SerTyrGlyPhe    TyrGlyCysHisCysGlyVal

59      GlyGlyArgGlyIleProValAspAlaThrAspArgCysCysTrpAlaHisAspCysCys
         |  |  |  |  |  |  |  |  |  |  |  |  |  |  |        |  |  |
 52      GlyGlyArgGlySerProLysAspAlaThrAspTrpCysCysValThrHisAspCysCys

79      TyrHisLysLeuLysGluTyrGlyCysGlnProIleLeuAsnAlaTyrGlnPheAlaIle
         |  :  |  |  |  |  |     |  |        :  |     :  |     |  :
 72      TyrAsnArgLeuGluLysArgGlyCysGlyThrLysPheValThrTyrLysPheSerTyr

99      ValAsnGlyThrValThrCysGlyCysThrMetGlyGlyGlyCysLeuCysGlyGlnLys
                     :  :     |                    |        |     |
 92      ArgGlyGlyGlnIleSerCysSerThrAsn    GlnAspSerCysArg   LysGlnLeu

119      AlaCysGluCysAspLysLeuSerValTyrCysPheLysGluAsnLeuAlaThrTyrGlu
            |  |  |  |  |  |  :    |    |  |  |     |  |     :  |
110         CysGlnCysAspLysAlaAlaAlaGluCysPheAlaArgAsnLysLysSerTyrSer

139      LysThrPheLysGlnLeuPheProThrArgProGlnCys    GlyArgAspLysLeuHis
            :  |  :  |  :  |  :        |    |  |  :
129      LeuLysTyr   GlnPheTyrProAsnLys    PheCysLysGlyLysThrPro   Ser

158      Cys
         |
146      Cys
```

Matches = 56      Mismatches = 87      Unmatched = 18
Length = 161      Matches/length = 34.8 percent Top line is RPLA2-8 deduced amino acid sequence; bottom line is rat type II amino acid sequence. 1 indicates match, : a consevative substitution and no symbol, a mismatch.

Fig. 11A

```
         10        20        30        40        50        60
GAATTCCGGTGGATGGAGGGGGCTGAGCAGGATGTTGACTGGCTATCGTTCATTGAGCAC
Clone linker
         70        80        90       100       110       120
TCTCACGATCAGCATCACGCACGGAATCCATCCTTCCTGTGTTGCAGCTTGTAGACCCTG 130       140       150       160       170       180
ATGCTTGGGCTGCCAGCATAAACGTGGGGATCCAGACTCTGTCTACCGAGGCTGCCCATA
gaattccggtccaggcctgtcctatgggcagcagcctcggtagacagagt....
Clone linker
        190       200       210       220       230       240
GGGACAGGCCCTGGGAAGAGGAGCTGAGACCAGGCTAAAAAGAACCCAAGAAATGAAGCG
                                                    MetLysAr
        250       260       270       280       290       300
CCTCCTCACGCTGGCTTGGTTCCTGGCTTGCAGTGTGCCTGCAGTCCCAGGGGGCTTGCT
gLeuLeuThrLeuAlaTrpPheLeuAlaCysSerValProAlaValProGlyGlyLeuLe
Rclo10-5' (primer)
        310       320       330       340       350       360
AGAACTGAAGTCCATGATTGAGAAGGTGACTGGGAAGAATGCCGTAAAGAACTATGGCTT
uGluLeuLysSerMetIleGluLysValThrGlyLysAsnAlaValLysAsnTyrGlyPh
Rclo10-1 (primer)
        370       380       390       400       410       420
CTACGGCTGCTACTGTGGCTGGGGCGGCCACGGGACCCCTAAGGATGGCACTGATTGGTG
eTyrGlyCysTyrCysGlyTrpGlyGlyHisGlyThrProLysAspGlyThrAspTrpCy
                                         Rclo10-2 (primer)
        430       440       450       460       470       480
CTGTCGGATGCACGACCGTTGTTATGGGCTACTGGAGGAGAAACACTGTGCCATCCGGAC
sCysArgMetHisAspArgCysTyrGlyLeuLeuGluGluLysHisCysAlaIleArgTh 490       500       510       520       530       540
CCAGTCCTATGACTACAGATTCACACAGGACTTAGTCATCTGCGAACACGACTCCTTCTG
rGlnSerTyrAspTyrArgPheThrGlnAspLeuValIleCysGluHisAspSerPheCy 550       560       570       580       590       600
TCCAGTGAGGCTTTGTGCTTGTGACCGGAAGCTGGTCTACTGCCTGAGGAGAAACCTCTG
sProValArgLeuCysAlaCysAspArgLysLeuValTyrCysLeuArgArgAsnLeuTr 610       620       630       640       650       660
GAGTTACAACCGTCTTTACCAGTATTACCCCAACTTCCTCTGCTAATGTCCTCTGTGGGC
pSerTyrAsnArgLeuTyrGlnTyrTyrProAsnPheLeuCysEnd
                                     Rclo10-3' (primer)
        670       680       690       700       710       720
TCTCGCCGGGAGTGCCTCCCACAGTGGCGGCCCCCCTCGGCTGTATTCCTGATCCGTCCA 730       740       750       760       770       780
CCCAAGGTCTTGGATCTGCCTTCCTCTGTGTACCACTGGGCTGGACAGAGCCCAGGGTTA 790       800       810       820       830       840
CACCCTACCCTCCAGAATCCTAGAGAGGGACTCTGATGTAGAGTCTGCGGACTCTGGATA
```

Fig. 11B

```
            850       860       870       880       890       900
GCTGAGCCTGCACTTGCAGAATTTGGCGCTGGGCCCCGGAGCTCCCTCAGCTCCAGGCCA 910       920       930       940       950       960
GTGTCGTGTTGACTTTCCTTTCAATTTCTGGAACCCAACTGCCATTACCACCCTCCAGAG 970       980       990      1000      1010      1020
ACCTCTTACTAGAGGAGAAGCCAAATTAACTCTATAAATCTGCCATGTAGCTATTAAATA 1030      1040      1050      1060      1070      1080
AAACCCATTCACGAGGCGAGAAGAACACCACCCCAGCACTCCCTCTGACAGGGCTGGGGT 1090      1100      1110      1120      1130      1140
AGGAGTGCCAATGCTTCTCTAACCCCTGAGGCATCTGTGCACCCTCTAGGATGGAGGTCA 1150      1160      1170      1180      1190      1200
GGAAACAGGTGGGGGCCTTACATGCCTTTCATGGTTTGTCTTGAGTTTATTTTCTTAAAC 1210      1220      1230      1240      1250      1260
CTTAGGGTCTTTCAAGCCAGACCTGGAGCTCAAGATTCTTCTGGAGGAAGGTGAGACACA 1270      1280      1290      1300      1310      1320
GCCCTATGCCACCTTGAGCTCCAGGCTAGAAAGGGACAGCCCCTAGCCCTGGCTTCTGCA 1330      1340      1350      1360      1370      1380
ACTGTGTGGTCTTGAACCTCCGTATAGTCCGAATCCCTCTGGCTCTCCTCAAAATATAAA 1390      1400      1410      1420      1430      1440
ACAAGCCTCCTTCCAATAGCATATTGGTGCACACCCCTAATCCCATCACCTGGGAGGAGG 1450      1460      1470      1480      1490      1500
AGGCGGCAGGAGCATCAGGAGTTCAAGGCCAGCTCCTGCCCCCTAGCAGGGATGGTAGGC 1510      1520      1530      1540      1550      1560
TGCATGAGAGTGTGTCTCAGAAAGAACCACCTGGTGCGGGTACAGGGATGCTGGGATTCT 1570      1580      1590      1600      1610      1620
GAGATGTCACTCAGTGCGGGAAAAGATTCAAGGAGGGGAACAGATCAATGGCAGAATGAC 1630      1640      1650      1660      1670      1680
TGTCTGTGCCGAGTTAAGGGCACTGAAAATCTCAGCTCATCTATCGCTTTATAGAAGATA 1690      1700      1710      1720      1730      1740
GAGCTTTGGGAGGAAGCAAGGCACTCTACAGTAAAGGAGTGGCCTTTCCAAGGAAGGGTC
                              Polyadenylation site
       1750      1760      1770      1780      1790      1800
TAGGCTCCTTCTTCTCCAGAACATGCACAGGACATAGGAGATCCATTATTTAGAGACCTT 1810
TCGTGTTCGAACGTTTTCTCCGGAATTC----RPLA2-10-1
                    Clone linker
      ......aaataaagttaattatattgagccggaattc----RPLA2-10-2
   Additional Polyadenylation site.   Clone linker
```

Fig. 11C

The top sequence comes from RPLA2-10-1. The bottom sequence is from RPLA2-10-2. Both the sequences are identical except for the 5' and 3' sequences indicated by the lower case letters.

Fig. 12

```
              10        20        30        40        50        60
         GGATACCAATGTTCCGACTGGAGACGGGGAGCCCGCGAGACCCGGGTCTCCAGGGTCTGC
              70        80        90       100       110       120
         CCAAGGAAGTTGCTCATGGGAGCAGACCCCTAGAGCAGGATTTGAGGCCAGGCCAAAGAG
             130       140       150       160       170       180
         AACCCCAGAGATGAAAGGCCTCCTCCCACTGGCTTGGTTCCTGGCTTGTAGTGTGCCTGC
                       MetLysGlyLeuLeuProLeuAlaTrpPheLeuAlaCysSerValProAl
         Hclo10-5'(primer)              Hclo10-A (primer)
         Clone HPLA2-10-5----CCTCC....
             190       200       210       220       230       240
         TGTGCAAGGAGGCTTGCTGGACCTAAAATCAATGATCGAGAAGGTGACAGGGAAGAACGC
         aValGlnGlyGlyLeuLeuAspLeuLysSerMetIleGluLysValThrGlyLysAsnAl
                 Clo10-1 (primer)              Clone HPLA2-10-7----AACGC....
             250       260       270       280       290       300
         CCTGACAAACTACGGCTTCTACGGCTGTTACTGCGGCTGGGGCGGCCGAGGAACCCCCAA
         aLeuThrAsnTyrGlyPheTyrGlyCysTyrCysGlyTrpGlyGlyArgGlyThrProLy
             310       320       330       340       350       360
         GGATGGCACCGATTGGTGCTGTTGGGCGCATGACCACTGCTATGGGCGGCTGGAGGAGAA
         sAspGlyThrAspTrpCysCysTrpAlaHisAspHisCysTyrGlyArgLeuGluGluLy
              Clo10-1a (primer)
             370       380       390       400       410       420
         GGGCTGCAACATTCGCACACAGTCCTACAAATACAGATTCGCGTGGGGCGTGGTCACCTG
         sGlyCysAsnIleArgThrGlnSerTyrLysTyrArgPheAlaTrpGlyValValThrCy
             430       440       450       460       470       480
         CGAGCCCGGGCCCTTCTGCCATGTGAACCTCTGTGCCTGTGACCGGAAGCTCGTCTACTG
         sGluProGlyProPheCysHisValAsnLeuCysAlaCysAspArgLysLeuValTyrCy
             490       500       510       520       530       540
         CCTCAAGAGAAACCTACGGAGCTACAACCCACAGTACCAATACTTTCCCAACATCCTCTG
         sLeuLysArgAsnLeuArgSerTyrAsnProGlnTyrGlnTyrPheProAsnIleLeuCy
                                                        Hclo10-C (primer)
             550       560       570       580       590       600
         CTCCTAGGCCTCCCCAGCGAGCTCCTCCCAGACCAAGACTTTTGTTCTGTTTTTCTACAA
         sSerEnd
         Hclo10-3' (primer)
             610       620       630       640       650       660
         CACAGAGTACTGACTCTGCCTGGTTCCTGAGAGAGGCTCCTAAGTCACAGACCTCAGTCT
             670       680       690       700       710       720
         TTCTCGAAGCTTGGCGGACCCCCAGGGCCACACTGTACCCTCCAGCGAGTCCCAGGGGAG
             730       740       750       760       770       780
         TGACTCTGGTCATAGGACTTGGTAGGGTCCCAGGGTCCCTAGGCCTCCACTTCTGAGGGC
             790       800       810       820       830       840
         AGCCCCTCTGGTGCCAAGAGCTCTCCTCCAACTCAGGGTTGGCTGTGTCTCTTTTCTTCT
             850       860       870       880       890       900
         CTGAAGACAGCGTCCTGGCTCCAGTTGGAACACTTTCCTGAGATGCACTTACTTCTCAGC
             910       920       930       940       950       960
         TTCTGCGATCAGATTATCATCACCACCACCCTCCAGAGAATTTTACGCAAGAAGAGCCAA
             970       980       990      1000      1010
         ATTGACTCTCTAAATCTGGTGTATGGGTATTAAATAAAATTCATTCTCAAGGCT
                                       Polyadenylation site
                                                             .....AATAAA
                                                              Additional
         AACCACATTGGCATTTTC----HPLA2-10-3
         Polyadenylation site
```

Fig. 13

```
1    MetLysGlyLeuLeuProLeuAlaTrpPheLeuAlaCysSerValProAlaValGlnGly
     |  |  |  |  |  |  |  |  |  |  |  |  |  |  |  |  |  |  |  |
1    MetLysArgLeuLeuThrLeuAlaTrpPheLeuAlaCysSerValProAlaValProGly

21   GlyLeuLeuAspLeuLysSerMetIleGluLysValThrGlyLysAsnAlaLeuThrAsn
     |  |  |  :  |  |  |  |  |  |  |  |  |  |  |  |  |  |  :  |
21   GlyLeuLeuGluLeuLysSerMetIleGluLysValThrGlyLysAsnAlaValLysAsn

41   TyrGlyPheTyrGlyCysTyrCysGlyTrpGlyGlyArgGlyThrProLysAspGlyThr
     |  |  |  |  |  |  |  |  |  |  |  |  :  |  |  |  |  |  |  |
41   TyrGlyPheTyrGlyCysTyrCysGlyTrpGlyGlyHisGlyThrProLysAspGlyThr

61   AspTrpCysCysTrpAlaHisAspHisCysTyrGlyArgLeuGluGluLysGlyCysAsn
     |  |  |  |  |  |  |  |  :  |  |  |  |  |  |  |  |  |  |  |
61   AspTrpCysCysArgMetHisAspArgCysTyrGlyLeuLeuGluGluLysHisCysAla

81   IleArgThrGlnSerTyrLysTyrArgPheAlaTrpGlyValValThrCysGluProGly
     |  |  |  |  |  |  |  |  |  |  :  |  |  |  |  :  |  |  |  |
81   IleArgThrGlnSerTyrAspTyrArgPheThrGlnAspLeuValIleCysGluHisAsp

101  ProPheCysHisValAsnLeuCysAlaCysAspArgLysLeuValTyrCysLeuLysArg
     |  |  |  |  |  |  |  |  |  |  |  |  |  |  |  |  |  :  |
101  SerPheCysProValArgLeuCysAlaCysAspArgLysLeuValTyrCysLeuArgArg

121  AsnLeuArgSerTyrAsnProGlnTyrGlnTyrPheProAsnIleLeuCysSer
     |  |  |  |  |  |  |  |  |  |  |  |  :  |  |  |  |
121  AsnLeuTrpSerTyrAsnArgLeuTyrGlnTyrTyrProAsnPheLeuCys
```

Matches = 107     Mismatches = 30     Unmatched = 1
Length = 138      Matches/length = 77.5 percent Top and bottom lines are deduced amino acid sequences of HPLA2-10 and RPLA2-10, respectively.

Fig. 14

```
1    MetLysGlyLeuLeuProLeuAlaTrpPheLeuAlaCysSerValProAlaValGln
       | |       | |     | |       | :        :
1    MetLys    LeuLeuValLeuAlaValLeuLeuThrValAlaAlaAlaAspSerGlyIle

20   GlyGly    LeuLeu   AspLeuLysSerMetIleGlu    LysValThrGlyLysAsn
                :        :          | |            :        |
20   SerProArgAlaValTrpGlnPheArgLysMetIleLysCysValIleProGlySerAsp

37   AlaLeuThrAsnTyrGlyPheTyrGlyCysTyrCysGlyTrpGlyGlyArgGlyThrPro
                          | |    | |    | |      | |   | | |
40   ProPheLeuGluTyrAsnAsnTyrGlyCysTyrCysGlyLeuGlyGlySerGlyThrPro

57   LysAspGlyThrAspTrpCysCysTrpAlaHisAspHisCysTyrGlyArgLeuGluGlu
                       | |     :        | |    | |
60   ValAspGluLeuAspLysCysCysGlnThrHisAspAsnCysTyrAspGlnAlaLysLys

77   LysGlyCysAsn    IleArgThrGlnSerTyrLysTyrArgPheAlaTrp
             |       :          :    |          : : :
80   LeuAspSerCysLysPheLeuLeuAspAsnProTyrThrHisThrTyrSerTyrSerCys

93        GlyVal    ValThrCysGluProGlyProPhe    CysHisValAsnLeuCysAla
                       : |                          : |
100  SerGlySerAlaIleThrCysSerSerLysAsnLysGluCysGluAlaPheIleCysAsn

110  CysAspArgLysLeuValTyrCysLeuLysArgAsnLeuArgSerTyrAsnProGlnTyr
        | | |            |         :                   | |
120  CysAspArgAsnAlaAlaIleCysPheSerLysAla    ProTyrAsnLysAlaHis

130  GlnTyrPheProAsnIleLeu    Cys    Ser
                               |      |
138  LysAsnLeuAspThrLysLysTyrCysGlnSer
```

Matches = 45    Mismatches = 90    Unmatched = 16
Length = 151    Matches/length = 29.8 percent Top line is HPLA2-10 deduced amino acid sequence; bottom line is human type I amino acid sequence.

Fig. 15

| | |
|---|---|
| 1 | MetLysGlyLeuLeuProLeuAlaTrpPheLeuAlaCysSerValProAlaValGlnGly |
| 1 | MetLysThrLeuLeuLeuLeuAlaValIleMetIlePheGlyLeuLeuGlnAlaHisGly |
| 21 | GlyLeuLeuAspLeuLysSerMetIleGluLysValThrGlyLysAsnAlaLeuThrAsn |
| 21 | AsnLeuValAsnPheHisArgMetIleLysLeuThrThrGlyLysGluAlaAlaLeuSer |
| 41 | TyrGlyPheTyrGlyCysTyrCysGlyTrpGlyGlyArgGlyThrProLysAspGlyThr |
| 41 | TyrGlyPheTyrGlyCysHisCysGlyValGlyGlyArgGlySerProLysAspAlaThr |
| 61 | AspTrpCysCysTrpAlaHisAspHisCysTyrGlyArgLeuGluGluLysGlyCysAsn |
| 61 | AspArgCysCysValThrHisAspCysCysTyrLysArgLeuGluLysArgGlyCysGly |
| 81 | IleArgThrGlnSerTyrLysTyrArgPheAlaTrpGlyVal  ValThrCysGluPro |
| 81 | ThrLysPheLeuSerTyrLysPheSerAsnSer  GlySerArgIleThrCysAlaLys |
| 100 | GlyProPheCysHisValAsnLeuCysAlaCysAspArgLysLeuValTyrCysLeuLys |
| 100 | GlnAspSerCysArgSerGlnLeuCysGluCysAspLysAlaAlaAlaThrCysPheAla |
| 120 | ArgAsnLeuArgSerTyrAsnProGlnTyrGlnTyrPheProAsnIleLeuCys  Ser |
| 120 | ArgAsnLysThrThrTyrAsnLysLysTyrGlnTyrTyrSerAsnLysHisCysArgGly |
| 140 | SerThrProArgCys |

Matches = 63    Mismatches = 74    Unmatched = 8
Length = 145    Matches/length = 43.4 percent Top line is HPLA2-10 deduced amino acid sequence; bottom line is human PLA2 type II amino acid sequence.

Fig. 16

```
 1      MetLysArgLeuLeuThrLeuAlaTrpPheLeuAlaCys   SerValProAlaValPro
        |  |     |  |  |  |     |     :           |                |
 1      MetLysValLeuLeuLeuLeuAlaValValIleMetAlaPheGlySerIleGlnValGln

20      GlyGlyLeuLeuGluLeuLysSerMetIleGluLysValThrGlyLysAsnAlaValLys
        |  |     |  |     |        |  |     |     |  |  |        |
21      GlySerLeuLeuGluPheGlyGlnMetIleLeuPheLysThrGlyLysArgAlaAspVal

40      AsnTyrGlyPheTyrGlyCysTyrCysGlyTrpGlyGlyHisGlyThrProLysAspGly
        |  |  |  |  |  |  |  |  :  |  :  :  |  |  |
41      SerTyrGlyPheTyrGlyCysHisCysGlyValGlyGlyArgGlySerProLysAspAla

60      ThrAspTrpCysCysArgMetHisAspArgCysTyrGlyLeuLeuGluGluLysHisCys
        |  |  |  |  |  |     |  |  |  |  |              |     :  |
61      ThrAspTrpCysCysValThrHisAspCysCysTyrAsnArgLeuGluLysArgGlyCys

80      AlaIleArgThrGlnSerTyrAspTyrArgPheThrGlnAspLeuValIleCysGlu
                 :        :  |  :     :                 :  |
81      GlyThrLysPheValThrTyrLysPheSerTyrArgGlyGlyGlnIleSerCysSerThr

99      HisAspSerPheCysProValArgLeuCysAlaCysAspArgLysLeuValTyrCysLeu
        |              |        |  |  |  |  |  |  |  :           |
101     AsnGlnAspSerCysArgLysGlnLeuCysGlnCysAspLysAlaAlaAlaGluCysPhe

119     ArgArgAsnLeuTrpSerTyrAsnArgLeuTyrGlnTyrTyrProAsn   Phe
        |  |     |  |     |  |     |  :  |  |  |  |        |
121     AlaArgAsnLysLysSerTyrSerLeuLysTyrGlnPheTyrProAsnLysPheCysLys

136              Leu         Cys
                              |
141     GlyLysThrProSerCys
```

Matches = 62    Mismatches = 75    Unmatched = 9
Length = 146    Matches/length = 42.5 percent Top line is RPLA2-10 deduced amino acid sequence; bottom line is rat PLA2 type II amino acid sequence.

Fig. 17

```
1      MetLysArgLeuLeuThr    Leu   Ala         Trp        PheLeuAla
       |   |    |  : :       :               :           |  |  :
1      MetAspLeuLeuValSerSerGlyMetLysGlyIleAlaValPheLeuValPheIlePhe

13     Cys   SerValProAlaValProGlyGlyLeuLeuGluLeuLysSerMetIleGluLys
       |     :              : :                    |  |  :
21     CysTrpThrThrSerThrLeu   SerSerPheTrpGlnPheGlnArgMetValLysHis

32     ValThrGlyLysAsnAlaValLysAsnTyrGlyPhe    TyrGlyCysTyrCysGlyTrp
       :  |  |  :   |         |   :  |  :      |  |  |   |  |   |  |
40     IleThrGlyArgSerAlaPhePheSerTyr          TyrGlyTyrGlyCysTyrCysGlyLeu

51     GlyGlyHisGlyThrProLysAspGlyThrAspTrpCysCysArgMetHisAspArgCys
       |  |   :  |   |   |   |   |   |   |   |  |   |   |   |   |  |
59     GlyGlyArgGlyIleProValAspAlaThrAspArgCysCysTrpAlaHisAspCysCys

71     TyrGlyLeuLeuGluGluLysHisCysAlaIleArgThrGlnSerTyrAspTyrArgPhe
       |  |                    |         |          :  :  |   :
79     TyrHisLysLeuLysGluTyrGlyCysGlnProIleLeuAsnAlaTyrGlnPheAlaIle

91     ThrGlnAspLeuValIleCysGlu   His   AspSer      PheCysProValArg
           :           |   |                                |
99     ValAsnGlyThrValThrCysGlyCysThrMetGlyGlyGlyCysLeuCysGlyGlnLys

107    LeuCysAlaCysAspArgLysLeuValTyrCysLeuArgArgAsnLeuTrpSerTyrAsn
       |  |   |   |  :    |   |  |   |  |       :        |   |  :  |
119    AlaCysGluCysAspLysLeuSerValTyrCysPheLysGluAsnLeuAlaThrTyrGlu

127    ArgLeuTyr   GlnTyrTyrProAsnPhe                        Leu   Cys
       :   :       |   |       |                            |     |
139    LysThrPheLysGlnLeuPheProThrArgProGlnCysGlyArgAspLysLeuHisCys
```

Matches = 48      Mismatches = 87     Unmatched = 25
Length = 160      Matches/length = 30.0 percent Top line is RPLA2-10 deduced amino acid sequence; bottom line is RPLA2-8 deduced amino acid sequence.

Fig. 18

```
1     MetLysArgLeuLeuThrLeuAlaTrpPheLeuAlaCysSerVal   Pro   AlaVal
      |  |  |  |  |  |  |  |  |  |  :  |           |     :  :
1     MetLys    LeuLeuLeuLeuAlaAlaLeuLeuThrAlaGlyValThrAlaHisSerIle

19    ProGly   GlyLeuLeuGluLeuLysSerMetIleGlu    LysValThrGlyLysAsn
               :           :        |  |         :                |
20    SerThrArgAlaValTrpGlnPheArgAsnMetIleLysCysThrIleProGlySerAsp

37    AlaValLysAsnTyrGlyPheTyrGlyCysTyrCysGlyTrpGlyGlyHisGlyThrPro
      :  :        |     |  |  |  |  |  |  |  |  |  |     |  |  |
40    ProLeuArgGluTyrAsnAsnTyrGlyCysTyrCysGlyLeuGlyGlySerGlyThrPro

57    LysAspGlyThrAspTrpCysCysArgMetHisAspArgCysTyrGlyLeuLeuGluGlu
      |     |     |     |  |     |  |     :  |  |        :  |  |
60    ValAspAspLeuAspArgCysCysGlnThrHisAspHisCysTyrAsnGlnAlaLysLys

77       LysHisCysAla    IleArgThrGlnSerTyr    Asp    TyrArgPhe
               |   :           :           |          |        :
80    LeuGluSerCysLysPheLeuIleAspAsnProTyrThrAsnThrTyrSerTyrLysCys

91    ThrGlnAspLeuValIleCys    GluHisAspSerPheCysProValArgLeuCysAla
      :           :  :     |   :  :              |              :  |
100   SerGlyAsnValIleThrCysSerAspLysAsnAsnAspCysGluSerPheIleCysAsn

110   CysAspArgLysLeuValTyrCysLeuArgArgAsnLeuTrpSerTyrAsnArgLeuTyr
      |  |  |           |           :     :           |  |  :     |
120   CysAspArgGlnAlaAlaIleCysPheSerLys    Val    ProTyrAsnLysGluTyr

130      GlnTyrTyrProAsnPheLeuCys
                               |
138   LysAspLeuAspThrLysLysHisCys
```

Matches = 45      Mismatches = 89      Unmatched = 15
Length = 149      Matches/length = 30.2 percent Top line is RPLA2-10 deduced amino acid sequence; bottom line is rat PLA2 type I amino acid sequence.

Fig. 19A

SEQ ID NO: 33:

```
         10         20         30         40         50         60
AAGCTTTGTG GGATTTCTAT TATGAACAAC ATAGGTGCCT TTCCAACTCG GGAACAGAGG 70         80         90        100        110        120
AAATATGGAC TCCTCAAAAG AAAAAAAGAA GAGATGAAGG GATGATGTTG CCAAAGAAAG 130        140        150        160        170        180
AAATTTGGAA AAAAAAAAAC CAAACCAACA TTTGCACTTT CAAAACCATG GAACCCTTCT 190        200        210        220        230        240
TATTTTTATA TGTTCAGATC TAAATGCCAG AAAGGTTACC ACATTCAAAG GGAATGAGAT 250        260        270        280        290        300
TTGAAAATGA TTTCTTTGAG TCCTCTGCTG AGGTCTTTCC AAGGCACTAC AATTAGGGCT 310        320        330        340        350        360
TTGCACCCAA ATACCCTTGC CTCATTTTGG TCATTTTTGT CCTGGAACAG AGGTTCAGCT 370        380        390        400        410        420
GGGAGACCCC TCACACACAG GTGAAGGCGT GGCTGTAGAA CCTCAGACCC CCTGGTCTCC
                                                  Exon 1 ?
        430        440        450        460        470        480
TCAGGAATGA AGGTCATTGC CATCCTCACC CTCCTCCTCT TCTGCTGTAA GTAGAGAGCG 490        500        510        520        530        540
TTGGTGGGTC AGCACCAAGC TTCTGTCTTC CTGTTTATGT CAGTGGGAGG GGGGACTCTC 550        560        570        580        590        600
CAGGTGGCAC CAGGTGAGGG AAGTCACAAG TCCCGCAGAA AAGAATCAGG AAAGGAACGG 610        620        630        640        650        660
GCTCCCACCA ACGTCCTCTT GCTTCTGTTT CTGCTATAAA ATGGGCTGAT CCCAGTGTTG 670        680        690        700        710        720
GGATCTTATA AAGTGTCTAG GAAATCAGAG GTTGCCAACC ATTTGCTAGA AAGGGAGTTT 730        740        750        760        770        780
GAGTAGTATT TTACCCCCCC TCACCCTCAA GAGTCTTTTT ACTTTGGATG CTAGTAGCCT 790        800        810        820        830        840
TTTATTTAGG CATTGGATCA GAACAAAAAT GCAGGACATA TATCCAGCCT AATTTAACCA 850        860        870        880        890        900
ATGGATTAAA TGGCCTTATC AGGAAAAGAC CATTTTATGG TGACTTATGG GATAATTGGT 910        920        930        940        950        960
AGTTATAAGT CATTGCTGCC GGGAGATCCG ATTGCTTACC TCTGCAAAGT GAAGAAAGAC 970        980        990       1000       1010       1020
CTACTGGGAA ACAGTTTGGG GTCTACTGGA GACTGATAGA CTCTTTTGCT GGATTCGTTG
```

Fig. 19B

```
              1030       1040       1050       1060       1070       1080
         AGTGGAGGTT TCTCCAGATC CATTTTCCTG TCTCTTTCAA TTGAGTCACA ATAACTTTTG 1090       1100       1110       1120       1130       1140
         AGTCCCTAAG TCAAAGATGT CAAAAACAGA CTTCCTTTCC CCACAGTGAG TGGTGGAATT 1150       1160       1170       1180       1190       1200
         TACACTTTGC AAGGTGATAG TGCAGGAGGA TACCTGTACG CAGGGATGAC CGCCTCTGCA 1210       1220       1230       1240       1250       1260
         GCCCTCAGTG CGGCTCCAGG ACTGCTTGGG CACCAGTGAC CGCCCCATGG GTTTCTTCCG 1270       1280       1290       1300       1310       1320
         CCACACCCCC GTTTAGACTG AACACGATAG GTAGATCGAA GGCCACCTGA GAAAACTCCC 1330       1340       1350       1360       1370       1380
         CCAAAACTCT ATTTCTGTTT CTCTTCTTCA AAGTTCATGT CTTTGTTGTA TTTTTATTGC 1390       1400       1410       1420       1430       1440
         AAATTTACTA CATGCTTATA GTTAAAAAGT AAAATAAATG AGTATATAGC AACAAGGTAA 1450       1460       1470       1480       1490       1500
         AGCTCCTCCT CATCCTCCCC AGACCCCAGT TTTTTCCCTA CATCCAGATG TGACCACTCT 1510       1520       1530       1540       1550       1560
         TAAGAGTTTG ATATACATCC TCTATACAGC GTTTACCACA CACACATTCA AAACACCATA 1570       1580       1590       1600       1610       1620
         ATAGGAAGGG AACACATGCT GGGCCGGGCG CGGTTGTTCA TGACTATAAT CCCAGCACTT 1630       1640       1650       1660       1670       1680
         TGGGAGGCCG AGGCGGGCGG ATCACCTGAG GTCAGGAGTT CGAGACCAGC CTGGCCAGCT 1690       1700       1710       1720       1730       1740
         GGCAACATGG TGAAACCCGT CTCTATTAAA AATACAAAAA ATTAGTCAAG CATGGCAGTT 1750       1760       1770       1780       1790       1800
         GGGCACCTGT AATCCCAGCT ACTCAGGAGG CTGAGGCAGG AGAATTGCCT GAACCCGGGA 1810       1820       1830       1840       1850       1860
         GGCGGAGGTT GCAGTGAGCC GAGATCACAC CATTGCACTC CAGCCTGGGT AACAACAGCG 1870       1880       1890       1900       1910       1920
         AAACTCCGTC TCAAAAAAAA AAAAAAAAGA AGGAAAGGGA CACACGCTTA TTATGAAAGA 1930       1940       1950       1960       1970       1980
         CATGAGACAG CGGAGACGTG TATAAATGAT GTTGCCTGTT TTCTTTCTCT CTCTTCATCC 1990       2000       2010       2020       2030       2040
         ATGCTAGAGA TAGTGCTATC AAATGTAGTT ATTTTTGAGA CACATATTTC GTATTATCCC 2050       2060       2070       2080       2090       2100
         TGTCGTGACA TGTGGGTGGT TTCCAATTTT TTGATATCAC AGATAATGCT TCAGGAAACC
```

Fig. 19C

```
        2110       2120       2130       2140       2150       2160
ATTTTGTGTA TCGATTTGTG CCCACTCTCA TAAGCATCTT GTAGAAGCAA AAACAGCTGA 2170       2180       2190       2200       2210       2220
GTTCATGTGT ACTTGTCATT TAAAAAAATA ATAATTGAGG ATACCTTTCC TGCCTCTTAA 2230       2240       2250       2260       2270       2280
GTATTTTGTT TCTCCTGTGA GATAGTAAAG GCCTGATGAC ATCTGGAGGG ACTGGCGTTT 2290       2300       2310       2320       2330       2340
CTGGCTTTGA ACTTTTGCCA TTCATGTTGC ATCAGACCCG AGGGTGTTCT GCCTAGAACT 2350       2360       2370       2380       2390       2400
GTGGTTTCTT GCTTTGAGGG GGAAGACTAT GGTTGATGGG AAAGCCTTGT TCTGAACCTC 2410       2420       2430       2440       2450       2460
ATGGAAACTG GGTATTCATC TGGGTTAGCA AAAAACTAGC TGTGTTACAG GGGCAAATCT 2470       2480       2490       2500       2510       2520
GAACCTATTT TATTCCCCAG GAAAGAGGCT GGTGATTCCA GCCATGCCCC TTGCACTTCG 2530       2540       2550       2560       2570       2580
CTTTGGGGAT CTGGTGATAT TTCGAATGCT CAGCACTCTA GTAAGGGGAG GGGACATCAA 2590       2600       2610       2620       2630       2640
GGCAGCATCA TGCTCATTGC AACTTCCTTC TTCCTTTTTT TCTCATCGGT GGTGGCAGCC 2650       2660       2670       2680       2690       2700
CCCACCCACA GCAGTTTCTG GCAGTTTCAG AGGAGGGTCA AACACATCAC GGGGCGAAGT 2710       2720       2730       2740       2750       2760
GCCTTCTTCT CATATTACGG ATATGGCTGC TACTGTGGGC TTGGGGATAA AGGGATCCCC
Exon 2

2770       2780       2790       2800       2810       2820
GTGGATGACA CTGACAGGTG GGTGCAGAGG CTCTAAGGCC ACTTATCATT TGTTTTGCAT 2830       2840       2850       2860       2870       2880
TAAAGTTCAT GCTCAAAGCC AGAGAGAGGG TCTTAGGATT CTTGCCTGGC AAATAACAGA 2890       2900       2910       2920       2930       2940
AAACAACTCA GGCTAATGGA AGGAAGAACT GAACGGGATT TGGAGGATGG GTCTTGAGAA 2950       2960       2970       2980       2990       3000
ACCCAGGGTC GGGGCCAGCT TCTTGAGTGT GTGACCTGTG AAGTTTCACA GGGCCCAACA 3010       3020       3030       3040       3050       3060
CTCATAAGGG TCAGGGCCAG CTTCTTGAGC GTGTGATCTG TAAAGTTTCA CAGGGCCTGG 3070       3080       3090       3100       3110       3120
CACTCATAAC CCCCTAAACA TGGTTTACTG CTCTGCTGCC ACATCTTGAA ATTCTTAATA
```

Fig. 19D

```
          3130       3140       3150       3160       3170       3180
     AAGGGCCTCA TGTTTTCATT TTGCTTTACT CTCTGCAATT ATGCCGTTGG TCCTGCCCAG 3190       3200       3210       3220       3230       3240
     AGCTCTAGAA GCTGTTTCAT CCTCATAGTA AAAGTGCTCT GCTTTCAGCT CTCCAGCTTT 3250       3260       3270       3280       3290       3300
     TAGCACTATA CCCACAGCAC AACTGACTCA CTAGTCCTAA TTCCATATTC TGGAGAGGGC 3310       3320       3330       3340       3350       3360
     TCCAAAGTGG CCCACTTTGG AGAAGTTGTC CATCTGGGTG AGGTTGCATG GCACAAACCT 3370       3380       3390       3400       3410       3420
     GGCTTCAGGC CTACTCCAAA GGATGGGGGT GGGGGAGTGT GAGTTCCTAG AAAAAGTAGA 3430       3440       3450       3460       3470       3480
     GGTGGGTGTC ATCTGGTGAA TGTACGTGTG GGGAGGTAAG AAACGGGACA GTTTGCGTCT 3490       3500       3510       3520       3530       3540
     CAATTCATTT GAAGACATAA GAAAGCAAAA TGTTCCTTGC CACATTTAAG GTAGTATGGA 3550       3560       3570       3580       3590       3600
     GAAACATGTC CCACAGTGGC CTTAAATATC ACTCTGAGCT CGAGTCTTGT GGTGGCTCAT 3610       3620       3630       3640       3650       3660
     GAACCATGGA GGACCTAGAG GTTCGAAGGG CAATTGACGC TTATCAAATG CCCTTATGTG 3670       3680       3690       3700       3710       3720
     CCAAGCACTG GGACTGGCCG ATTGGCATAC AAACCTAATT TAATTCTCGC AGGGAATGCA 3730       3740       3750       3760       3770       3780
     CGACACAGTT GATACCAGCC CATTTGACAG CCTGAGGACA TGTGAGTTGC TAAACCACCT 3790       3800       3810       3820       3830       3840
     CCTAAAGGCA ATGCAGCTTC TAAGTGGCAG AGTTTAGGAT TGAACGAGAA TTTGCCTATT 3850       3860       3870       3880       3890       3900
     TCAAAGTTTG TCCCCTCTCC TTGATGGTCT GTGCCTCCCC TGTCAAAGTC CAAAGGCTGA 3910       3920       3930       3940       3950       3960
     TTAGAAATTG AACATCATTA GCCAAAGCTG ATCAACAGCA GAGCCCCCAC TTGCAGATGG 3970       3980       3990       4000       4010       4020
     GAATGGTGAG AGAGGGAGAC TGAAACACTT TTTTCTTGGC CTTTCAGGGT TTAGAATCCA 4030       4040       4050       4060       4070       4080
     AGCTTAAGTT TCTGCCTTCC TGTCCCTTGT GTAGTGGTTG AGGACATGGA CTGAGCCCAT 4090       4100       4110       4120       4130       4140
     GCTCCAGATG GTATTTCTCC TCCAGTGCTC TCCCATCCAG CCCCCAGCCA ACTCTGGGTG 4150       4160       4170       4180       4190       4200
     CCATGAATGG GACTACGTCG GCTTTTACAG ACAGTTGTCT CCTCAGAGAC CGTTACAGTG
```

Fig. 19E

```
           4210       4220       4230       4240       4250       4260
      CCTGACTCAC AGTAGGTGCT CAGTAAAAAG TGTTAAATGA ATGAATGGGC CTAGGTTTGT 4270       4280       4290       4300       4310       4320
      GTCCTGGGTC TATCATTCTC CAGCTGCCTA AGTTTGGGAA ATTGGCCTCT TGGAATCTCA 4330       4340       4350       4360       4370       4380
      GTCCCTCCCC TACAAAAGGG CAGCAATGAT TGTACTTTAT AGTTTCTAGT AGCTAATGAG 4390       4400       4410       4420       4430       4440
      ATAGCAACAG ATACTACAGA GGGCTCAGGA AATGCTACTG GTTATTATTA TTATTTTTA 4450       4460       4470       4480       4490       4500
      TTTTATTTAT TTTTTGGGAG ACGGGGTCTT GCTCTATTAT CCAGGCCTGG GGTGGAGAGG 4510       4520       4530       4540       4550       4560
      CTCAATCAGA GCTCACTGCA GGTCCTCAAG CAATCCACCC ACTTCACCTC CTGAGTAGCC 4570       4580       4590       4600       4610       4620
      GGGACCACAG GCTGGTGCCA CCATGCCTGG CTTTTTTTTT TTTTTAAAC TTAAAAAACA 4630       4640       4650       4660       4670       4680
      TAGGCGGCTC CCTATGTTGC CCAGGCTGGT CTCAAACTCC TGGACTGAAG CGATCCTCCT 4690       4700       4710       4720       4730       4740
      GCCTTATCCT CACAAAGTGC TGGGATTGCA GGCATGAGCC ACCACACCTG GCCTATGTTT 4750       4760       4770       4780       4790       4800
      AATATTATTG ATAATTCACC TCCTCACCTT CAATGCCTTC TTGCCTAGAG GAGGAGGCAG 4810       4820       4830       4840       4850       4860
      GTGAGCCCTT TCTAGTCCCC AGATAAGGTC CTCCAGCAGA TTCCTGAGGG ACCCACTTCC 4870       4880       4890       4900       4910       4920
      AGGCACAGCC CCTCATCTCC CTCTCCCTAC GAGAAGCTGA AGGAGTTCAG CTGCCAGCCT 4930       4940       4950       4960       4970       4980
      GTGTTGAACA GCTACCAGTT CCACATCGTC AATGGCGCAG TGGTTTGTGA GTAGCCTTTT 4990       5000       5010       5020       5030       5040
      CTGTATGGAA ATGTCTTTTA ACCTGGGCCT TTCCTTAACG TTCACCTCCT CTTTGACCCA 5050       5060       5070       5080       5090       5100
      GAGATCTTTT AGAAAATGAA ATGCTTCCAA GTGCTTGGAA GGAGATATTC CTGAGCTTTC 5110       5120       5130       5140       5150       5160
      TCCTGATGCT CCAGAGCTTC TCAGAGTGTC CGTGCTCATC CTGCCCTGGT CTCTCCCACC 5170       5180       5190       5200       5210       5220
      CATGAGTGTA CCTCCTGAAC TCTCTGGGGG CCCAGAGCCT GGCAGATAGT ACATGCTCAG 5230       5240       5250       5260       5270       5280
      TAAATACTTG TTCACTTGAG CTAATCTTGA AGCTTCCCTT GACAACTGCT GCTGTTGAGA
```

Fig. 19F

```
        5290       5300       5310       5320       5330       5340
   ACATGTTTCC TTGTTTCTGT GATTTTGTTA ACAAAACGGC TCAGCTGTCT TCCAGTTGGA 5350       5360       5370       5380       5390       5400
   CAAATATTTA TTAAGGGCGA CTGCATGCCA AGCACTAAGA TAGGTGCTGC CAGGGCCACA 5410       5420       5430       5440       5450       5460
   AAAGCAAATA GGTGGGAAGG GAAGGGGGAC TCACATGTTA CTGAGACCAT TCAAGGAGCC 5470       5480       5490       5500       5510       5520
   ATGTGGGCAA GTGGATCAGT GCCCTTCACA TGGGGCGTGG CCTGGCATCC GGAGCGTGTT 5530       5540       5550       5560       5570       5580
   CTGCGGCTGG TAGGGTATGG GTATGTGCAG GGCAATCCTG GCCTAGACAG CAGGCACATT 5590       5600       5610       5620       5630       5640
   TGGAGGCACG GGACAGTAGT CTTTCGTGAG CACCATCCTT TCCAGCATAG CCAGGGTGGA 5650       5660       5670       5680       5690       5700
   TCCTGGGGTC CTGGGCTGGG AGGGTGAAGA GCAACAAATA AAGAAGTGGC TTCTTGGCCG 5710       5720       5730       5740       5750       5760
   GGCGCGGTGG CTCACGCTTG TAATCCCAGC ACTTTGGGAG GCCGAGGCGG GCGGATCACG 5770       5780       5790       5800       5810       5820
   AGGTCAGGAG ATCGAGACCA TCCTGGCTAA CACGGTGAAA CCCCGTCTCT ACTAAAAATA 5830       5840       5850       5860       5870       5880
   CAAAAAAAAT TAGCCGGGCG TGATGGTGGG CGCCTGTAGT CCCAGCTACT CGGGAGGCTG 5890       5900       5910       5920       5930       5940
   AGGCAGGAGA ATGGCGTGAA CCCGGGAGGC GGAGCTTGCA GTGAGCCGAG ATTGCGCCAC 5950       5960       5970       5980       5990       6000
   TGCACTCCCG CCTGGGCCAC AGAGCGAGAC TCCGTCTCAA AAAAAAAAA AAAAAAAAG 6010       6020       6030       6040       6050       6060
   AAGAAGTGGC TTCTTATAGT GTGTGGCTCA CTTCCTGCCT GGCCTCGTGG GGTTGCATGA 6070       6080       6090       6100       6110       6120
   ATCACTTTCC TTCCCAGGTG TATTTATTCA GAGCTGTGAG TGCACCTTGG AGTTCCTCTG 6130       6140       6150       6160       6170       6180
   TTTCCTCCTG AGGTCAGGGA ACTACCACCT CTCTGCCACT CATCCCCTAT GGCGGGAGAT 6190       6200       6210       6220       6230       6240
   ACATCCTCCA TCCCGTAGTG GGTTCCAGGG CTCAGAACCC TGGTACTCCT GAGCTCCCCA 6250       6260       6270       6280       6290       6300
   ACCCACCACT TCAGCTCAGC ACACACCAAT ACCCAGAGTT AGGACTGTGA GGTCTCCCTG 6310       6320       6330       6340       6350       6360
   GCACCAGCTG TGTGGGTTGG GGGCTCGGAC CCCTGCACCG GGAGGACCTG CCTCAGCTCT
```

Fig. 19G

```
      6370        6380        6390        6400        6410        6420
TGGCCTGCCC  TGCCCACTGC  CACCAGCACG  TGGTTGACAG  GGAAAGAACC  CCCTTTTGTT 6430        6440        6450        6460        6470        6480
CCCCACGTGA  GCTCAAGCAA  TCCACCCACT  TCAGCCTCCT  GAGTAGCTGG  GATTACAGGT 6490        6500        6510        6520        6530        6540
GCCCACTGCC  ATGCTTGACT  AATTTTTTGT  ATTTTTAATA  GAGACGGGGT  TTCACCATCT 6550        6560        6570        6580        6590        6600
TGGCCAGCTC  AGCACACACC  AATACCCAGA  GTTAGGACTG  TGAGGTCTCC  CTGGCACCAG 6610        6620        6630        6640        6650        6660
CTGTGTGGGT  TGGGGGCTCG  GACCCTGCAC  CGGGAGACCT  GCCTCAGCTC  TTGGACTGCC 6670        6680        6690        6700        6710        6720
TGCCACTGCC  ACCAGCACGT  GTTGACAGGG  AAAGAACCCC  TTTTGTTCCC  ACGTGAGCTC 6730        6740        6750        6760        6770        6780
AAGGAGACTT  CCCTGAGTTG  GAGCTCTCTG  GTGTGGTCCT  TCTCAGGCCT  AAAGCAAAGT 6790        6800        6810        6820        6830        6840
GTCTTTTCTG  TGACACCTCC  AAGGCCATGT  TCAGGAGAGG  GGAAGGGATC  AGGGCCTGGT 6850        6860        6870        6880        6890        6900
GGGAGGGATG  GGGAGAGGGG  ACTGGAGAAG  GTGGCCTCCA  GGGATCGAGT  TTCCCATGGC 6910        6920        6930        6940        6950        6960
CTCTTCCCAC  CTGTCTTTGC  CACAGGGGTG  GGGACACCTG  GCTGGCCCAG  CCCAAGCCTC 6970        6980        6990        7000        7010        7020
CACCCTGGGC  TCCTGTGGGC  TGGCTGCACT  CGCCAGGGCT  GGCCTAGGCT  CTCTGCACCC 7030        7040        7050        7060        7070        7080
AGGGAAGCTT  CTCTATTCAA  TGCTCTTCAC  CCTCCCAGCC  CAGGACCCCA  GGAGATGAGG 7090        7100        7110        7120        7130        7140
GAGAGTGGAG  CAAAGGTTGA  GGAGCAGAGG  CTGGAGCCCC  AGGCAGTGGC  ACTGCTGGGC 7150        7160        7170        7180        7190        7200
AGTGGTGGGA  GGTGCCAGCC  AGGGCTGGGA  GTTGGACCCG  AAAGTACGTG  GCCTGGGCTG 7210        7220        7230        7240        7250        7260
TACTTTCTTC  CCACGTTGCC  CCTTCAGAGC  AGAAGCAGCC  AGTTGCTCCT  GAAGCCTTGA 7270        7280        7290        7300        7310        7320
CCAGGGCTCC  TGAGTCCAGA  GCCTTGCTCA  GGGCACTAGC  GTGGGAGGAG  GCTTCCGCAT 7330        7340        7350        7360        7370        7380
CAGTACAGGG  CATCAGCACC  CGCCTCCTCA  GCTGACCCAG  CCCCGTGAGG  ACCCAGGCCC 7390        7400        7410        7420        7430        7440
AGCCCCTGT   CATCCCCACC  CCCACCTTGC  CAAGCCCCTG  CCCCCAGGAG  CAGGGCTGAG
```

Fig. 19H

```
        7450       7460       7470       7480       7490       7500
    AGCGAGGTGA TCTGGGTTCT AATCCAGAGT CTGCTGCTGA CATGTGCTGA GCCCCAGGCC 7510       7520       7530       7540       7550       7560
    CATTGGTTTA CTTGCCCCAG TATTGAGCGA GCATCCACTG GGTACCCGCC CAGTGCCGGT 7570       7580       7590       7600       7610       7620
    GCTGTGCCAG GGGCCGGGGC ACAGAATAAA GCAGACCCGT CCCTGCTCTT CTGGCATTCA 7630       7640       7650       7660       7670       7680
    CAGTCTTGTG GAAACTCCAG ACTGAAAGTG CCCTTAGAGA TTATCCAGAT CAGCCCCTCC 7690       7700       7710       7720       7730       7740
    TTGTAGCAAT GAAGAGACTG AGACCCACAG AGGGGATGAG TTTGATCCAA GAAACAGACA 7750       7760       7770       7780       7790       7800
    AGATTAAGAT GCATGTGTCT TGAACCTTTT CAGTGCTCTG GAACATACCG TCTGGCCGGA 7810       7820       7830       7840       7850       7860
    GTTGTCTGGG CTTTGGTTTT CCCATCCATG AAATGGGTAC AATAACAACA GCTATAGTGT 7870       7880       7890       7900       7910       7920
    ATGAGCCTCT GTGATAGATG CTGTACGCAC AGCACCTGAA CTCACATGAT AAACCACTGA 7930       7940       7950       7960       7970       7980
    GGTGAGCATT ATCTCCCATT ATCAAGGAGG ACCCTGGGGC TCAGAGAGGT TAAGCACGAT 7990       8000       8010       8020       8030       8040
    GCCAAGGCCA CACAGCCAGG GAAAGAAGAG TTGGAATTCA AACCCCGGGT GCCCTGTCTC 8050       8060       8070       8080       8090       8100
    ACACTAGCTT CCCCTGTGGA GGGTGCTGGT GTGTGCATGA TTGGAGGCCC TCACACAGTG 8110       8120       8130       8140       8150       8160
    TAAGTCTCAG GATCTGCAGC AAACTGGTCA GAATGCTCTG CCCTGGCCCA GGGAAGGAAA 8170       8180       8190       8200       8210       8220
    GAGGGGCAGA TGGAGTTTGC TTCGCTGTAA GGCCCCGGAG CTTTGTGTTC CTGCTGAGAA 8230       8240       8250       8260       8270       8280
    GCCTCAGAGT CGGGCAACAC TGGGTCTAAT TCCAGCTCCA CCCCTTGTAT TAATAGCTGG 8290       8300       8310       8320       8330       8340
    GCCTTAATCT CCTCATCTGT AAAATGGAGA GAATCGTCGC CTGTACTTCA TAAGGCTGCT 8350       8360       8370       8380       8390       8400
    GGAAGGATTA GCTAAAGCAA CCCAGCTACA GTGGCTGGCC TACAGTAGGT GCTTCATTAA 8410       8420       8430       8440       8450       8460
    TGCCCTTCCT TTTAGATGTG GAAATTCCTC TTTTTGTCCA AGTTTTCTTT TCCTCTTTGC 8470       8480       8490       8500       8510       8520
    TTACGGCACT GGGATTTTCT TTATTACTGT TTCTTTGAAG AGTCCGCTCT GTACTTGTGC
```

Fig. 19I

```
          8530       8540       8550       8560       8570       8580
    CCACGGCTAT GGTCAGTAAC CCCTTATGGA ATAAAACCCC TTTCCTGGCC AGGTGTGGTG 8590       8600       8610       8620       8630       8640
    GCTCATACCT GTAATCCCAG CACTCTGGGA GGCTGAGGCG GGAGGATCAC TTGAGCCCAG 8650       8660       8670       8680       8690       8700
    GAGTTCGAGA CCAGCCTGGG CAACACAGTG AGACCCCTGT CTCTACTAAA CATACAAACA 8710       8720       8730       8740       8750       8760
    ATTAGCCAGA TGTGGTGGTG CATACCTGTA GTCCCAGCTA CTCAGAAGGC TGAGATAGGA 8770       8780       8790       8800       8810       8820
    GGATCACCTG AGCCCAGGAG ATGAGGCCAC AGTGAGCTGT GATTGCACCA CTGCACTCCA 8830       8840       8850       8860       8870       8880
    GCCTGGGCAA CAGAGTGAGA CCCTACCTCA AAAAGAAAGC AACAACAGAA AACCTATTTC 8890       8900       8910       8920       8930       8940
    CCTATCCTAA TTGCACCTCC ATTCAAAGAG CTGCCCCTGC AAGAGTTAAC CAACTCCCTA 8950       8960       8970       8980       8990       9000
    GCCTCCCATG AGTTCTGAAA TCCTGCACCC AGGCCTGGTC CCAGTTGCCT AGCAACCGGG 9010       9020       9030       9040       9050       9060
    GGCTGCTCTG GGATGCAGTA GGTAAGCAGG GGAGGGAGAG GAAGAAAACA ACTTGGTCTG 9070       9080       9090       9100       9110       9120
    TCCACGACTC TAAATGTCAC TGAGAGATCA GTGCAGAGAA AGGCCTGTCA CCAGAGCCCA 9130       9140       9150       9160       9170       9180
    GGGCCCAATT TGCCTGGTGG TAGGGACAGC TGCCCTCAGG CCACCTGGGA GGTGGTTATC 9190       9200       9210       9220       9230       9240
    CCTCCTTTGA GTGGGCTTAC ATAACTACTT GGCATTTTTG CAAGGGACTT TAAGCTCACT 9250       9260       9270       9280       9290       9300
    CAGCAGTGAC ACCCCCCTCC GCCCACATGC ACATACATGT GTGGTACAGG GAGGACCCGG 9310       9320       9330       9340       9350       9360
    TGTGGGAGGC AGAGATGGGG TTCCAGCCAA CTGAAACTCC ATCATCTGCA TCTCCCGGCC 9370       9380       9390       9400       9410       9420
    TCTGACTGCC TCCCTCTGCC AAAGCGGGAA GATGAAAATG GTAACTGCTG GAATTTGTAT 9430       9440       9450       9460       9470       9480
    TTTGCAAAGA CTTTTCTCAT TTACTGCTGA ATATATTCCT CATCTCAGCC TCCACTCGCT 9490       9500       9510       9520       9530       9540
    GACACGCTAC CCACTGTCTC TCCCAGCATT CATCTCTACC TGAAATGATC TTGTTTACTT 9550       9560       9570       9580       9590       9600
    CTCTGTGTCT GTGTGCCTCG ACTCTCCCCC ACCGACTAGA AAGGTCCGTG AGAGCAAGGA
```

Fig. 19J

```
            9610       9620       9630       9640       9650       9660
        GCAAGCCTGT CTTGTTTGAG GGCACTGGTT CTCATAGAGC CACAGGGAAT GATGCCCCTG 9670       9680       9690       9700       9710       9720
        GACTAAGCAG TGTGGGGTCT GCTGGCTTGC ACCTGTGCCC CCAGCTCCTA GCCAAAGACC 9730       9740       9750       9760       9770       9780
        AGACACATGT TGGGAACTCA ATACTTGTTT GTTTAATGAG TAGATGAACA AAAGCACTCA 9790       9800       9810       9820       9830       9840
        TGAAATAGGC AGTGCACGTA TCTTTATCAC CATTTGAAAG CTGAGGAAAC AGGCTTGGAG 9850       9860       9870       9880       9890       9900
        AGGGAAGCAA CTTGCCTGAC ACCCCAAATC ACAGAAGCAG CATATTTGGC CCAAGAACCT 9910       9920       9930       9940       9950       9960
        GGCTTCCTGT CTCCAAGGGG TCAGGTCCAG CTGGCATTGG CCTGTAGGCA TGTGAGTGTG 9970       9980       9990      10000      10010      10020
        GCAAGGTAGT CAGCAAAGAG CCTTTACTGC ATGTTGGGGT CAGAAGATCA GCAATAAGGA 10030      10040      10050      10060      10070      10080
        GGACAAAATC CTTGCCTGGA AGGAGCTTGT GTTCCAAAAA GAACAAGAGA CCACAGCATA 10090      10100      10110      10120      10130      10140
        TTCATTAATA AAGACACATT CAAACAGGGC CAAGTGCTCT GAAGCACCTC AGACAAAGCG 10150      10160      10170      10180      10190      10200
        ACAGGCTGCA AAATGACAGC GTTTGGGGGT CAGGAGACAG AAGGGTGCCT GCTTTAGGTG 10210      10220      10230      10240      10250      10260
        GTCGAAGAAG GCCTCTCTGG GGAGGTGGCA TTTGGTCTGA GACCTCAGGG CCAATGTGCT 10270      10280      10290      10300      10310      10320
        AGGAGCAGAG GAGCCTTGGG GAAGAATGGA GATGAGGTTG GACAGGATGA GACACGTGCC 10330      10340      10350      10360      10370      10380
        TTCTATGTCA ATGGCAAGGG AGTCATTGGA GCATGTGAAG CAGAGGATGC TCTACTTTTG 10390      10400      10410      10420      10430      10440
        CCCCAGAAAG ATCACTCTGG CTACAGTGCA GAGAAAGAAG AGAGTCAAGG AGGAAAGAAG 10450      10460      10470      10480      10490      10500
        GGCCTCATTA GGGGACTGTT GCAAAGCACA GGGAGGCACA ACCACAGCCA AGATCAGCAT 10510      10520      10530      10540      10550      10560
        GGTGACCAAT GGATGGAAGT GTCAGATGTC GCATGCTGTC GGTAGGTCAG GGCCGACAGG 10570      10580      10590      10600      10610      10620
        ACCTGTCGAT GGGTTCAGCG TGGGGTGTGA AGGAACACAG GCTGCACCCC AGCTCCTGGC 10630      10640      10650      10660      10670      10680
        CTGAGTGGCT GTAGATAGTG GCACCAAATA CTGAGCTCGT GAAGATGGGG GAGAGCTGAT
```

Fig. 19K

```
    10690      10700      10710      10720      10730      10740
GATGAAGACA GCAAGAGTTT GGTGTGAGTC ACCTTGAGTT TGAGACACGT GTCAGACATG 10750      10760      10770      10780      10790      10800
TAAGGGGTAG GCAGGTGGAC ACGTGCTTAT TGAAGTCTGG AGCCAAGGGA GAGGTGTGGG 10810      10820      10830      10840      10850      10860
CTGCAGCGGA GAAGTTGGGA GTATTCAGAG TTCTGACACT GACCAAGAAC ACCCCTCAGA 10870      10880      10890      10900      10910      10920
GAATTCAGAG ACAACCAGGG CTGAGGCGAG GGGCTTAGAC TGGGGCCTGG GACAGCCACA 10930      10940      10950      10960      10970      10980
GGCAGGAATG CAGACTTGCT GCCTCTTCTT ATTTGTGGAG ATGTAGTTCA TGCAGCAAGA 10990      11000      11010      11020      11030      11040
AAGTCATTCC AAAGCCCTCC TTTCCTTTCT TCATGCCTCA GTTTCTCCAT TAGCACATTA 11050      11060      11070      11080      11090      11100
AAAGATGCAA GATCTGGAGT TAAGCTTGTT TTTAAAAGGT GGCCTCCAAA GACGGTTTTT 11110      11120      11130      11140      11150      11160
CTTGGCCTGG GGCTGTCTCA TCATCCAGGT CATGACAGGC CCGGTCCATG GTTGAGGAAT 11170      11180      11190      11200      11210      11220
GCCACAGAAG TGACAGTCCA CTGCAAAAGA CTGCTGCTCC AGATCAGTTC TGGAAGGCCT 11230      11240      11250      11260      11270      11280
GGCAATGGGG CAGGCCACTG AAGTAGAACT GGATGTCAGA TGCACGCATT AGAAAGGACA 11290      11300      11310      11320      11330      11340
GGAAGACCAA ATGAGAAAGG GAGAGGGGGC AGGGAGAAAG GAAGGAGAGC TAGAGACTTG 11350      11360      11370      11380      11390      11400
AGGCAAAGGA AACAAGAGAT GGAATAGAAG AAGACAGAGG ACCAGAAGAC AGTGAGACCA 11410      11420      11430      11440      11450      11460
ACAGAAAGAG AGAGGGACGA GAAAGAAGGT GGCTGAGGAA GGTGAGAAAA GTGTTTCCAG 11470      11480      11490      11500      11510      11520
GGCGACAGCA ACTGGACCAG GCCCTCTAGT TGGACAGTGA GGCTGGCTGG GGGGCCTGAG 11530      11540      11550      11560      11570      11580
CTCAAGTAGC CCTCGTCCCC TGAGAGAGTG GGGGCTACCT GGGGAGCTGG GCTTGATGCA 11590      11600      11610      11620      11630      11640
TCTGGAAGGA TCTTCACAGA GGCAGGAGGG GGAGTGGGAG GGCAGAGGGC ACCCAGGCGC 11650      11660      11670      11680      11690      11700
TAGAACAGTG GGAGTGGCGG GACGCAAAAC CGGAGAGCCA GAGGAGTGAA CATCCCTGGC 11710      11720      11730      11740      11750      11760
AGATTCCCCT GCGGCCGAGC AGGAGGGCAG GAAGCTCAGT GGTGTTGGCA CAACGTGAGA
```

Fig. 19L

```
          11770      11780      11790      11800      11810      11820
      AGTTCCAGGG AGGCGTGGGA GGACGGCTTC TGCAGGACGC AGACTTTGCA GAGGGAGAGT 11830      11840      11850      11860      11870      11880
      GGCAAACAGA CTGACTGCAG GCAGCTCTGC CGGCTCCACA GGGCGCTGCT TTTTCTCCAC 11890      11900      11910      11920      11930      11940
      GGTGGAGCTG GAGTGCATCA CCCTGAGAAC CAGCAGCAAG CCCCCACAGG GCACCTTCTG 11950      11960      11970      11980      11990      12000
      CGTGCCAGGC ACATCCGGAC CACTTGTCGG TAGACACCAG TGACCCTCAC CACCACCCCA 12010      12020      12030      12040      12050      12060
      GGAATGGGAC AGTGTCATGT GTTTCTGAAA TGACTAGGTT TTAGCACCAT TTCATAGATG 12070      12080      12090      12100      12110      12120
      AGGAAGCTGA AGCTAACTTG CCCAAGGTCA TAAACCGGGC GTCTGGTGGC CTCCCCTCCT 12130      12140      12150      12160      12170      12180
      CACTGCCAAC CCTGAGAGCG GACTAGGGTG GAGTTATCTG GAAAGAGGAA GCTGTACCTG 12190      12200      12210      12220      12230      12240
      AGAGCCCTAA ACACACATGC GCGCGCACGA CACACACACA CGCACAAACA CACAATGCAC 12250      12260      12270      12280      12290      12300
      GCACACACAT GCGCACGCAC ATACACACAC ATGCACACAT GGACACATAC CTGCACACAC 12310      12320      12330      12340      12350      12360
      AAGCATACAC ATGCACACAG GCACACGCAT GCACACACGC GCATGCACAC ACATGCACAC 12370      12380      12390      12400      12410      12420
      ACATGTGCAT GCACACAGTG CGACAGCTCT GATTAGTAGG TAAATAAAAG GTTCCCATCT 12430      12440      12450      12460      12470      12480
      AGTGGTGACT CGGCCAAAGT GCAGACACTG AACCCCAAAG GCCCATAGAG GCTTCATTCA 12490      12500      12510      12520      12530      12540
      TCCCTTCTCT TATTCTTCAT TCATGGATTC TATTGAGCAT CTGCTCTGTG CAGCATCTGT 12550      12560      12570      12580      12590      12600
      CCTGGATGCT GGGGATACTG TGATGACTTA GACAAGGTCT CAGCCGCACA CAGCTTATGC 12610      12620      12630      12640      12650      12660
      TTCTTTGAGG GGAGGCAGAC ACAAGCCAGG AAACCAATAA GAGAAGTTAA GTAAAAAGCA 12670      12680      12690      12700      12710      12720
      CAGTGAGTGA GACAAACGGG TACGGAGGAC ATGGCCAGAG AGAGCTTTAG TTCAGGTGGT 12730      12740      12750      12760      12770      12780
      CAGGGAGCAC CTCTCTGAGG AGGTGAAATT TGACCAAGCC TCAAACAGTG GCAGGGATCC 12790      12800      12810      12820      12830      12840
      CACTGCTTGC AGATCCTGGG GAGAAGCATT TTAGACAAAA AGAACAGCAA GTCCAAAGGC
```

Fig. 19M

```
         12850       12860       12870       12880       12890       12900
     CCAGAGACAA  GACAGAGCAA  GACCTGTGAC  ATGAAACAGG  CTGGTGTGCC  CAGAGCAGGG 12910       12920       12930       12940       12950       12960
     AGGCTGGGAG  AGTGGAGGGG  GAGGGCGATG  AGGGTGGAGA  AGCTGGTGAG  GGTGGCATCC 12970       12980       12990       13000       13010       13020
     CGGCAAGTGT  GCCTGGCCAC  GGAGGCCACG  GAAGGATTCA  GCATGTCTTT  CCCGAATAGG 13030       13040       13050       13060       13070       13080
     AACCACACTG  GGCTGTAACA  GAGAGTGACG  TACTCGGTAC  GTTGAGAAGG  TCCTGCTTAT 13090       13100       13110       13120       13130       13140
     TTCCTTCCGT  GAAGGAGGAA  GAGCTGCTGA  TGACAGAGAT  TGGCAGTGGC  CAAAGACATA 13150       13160       13170       13180       13190       13200
     GAGAGAAGAG  GGCAGAACAT  GGGCTATTTT  AAACACAGAG  AAGATTAGCG  GGACCCGCTG 13210       13220       13230       13240       13250       13260
     GCAGACCGGA  CGTGAAATGT  GGAAGGAGCG  GGGGCAGCGA  GGTCGGCTCC  TAGTTTCCTG 13270       13280       13290       13300       13310       13320
     AGAATGTGGG  TGAATCACGG  GCTCACAGGC  AGAGGGAGCA  CTAGGATATC  AAGGGTTCCC 13330       13340       13350       13360       13370       13380
     TTGTGAACGC  CTCAAGTTGG  AGATGCCTGA  GACATCCAAG  TGAGATGTCA  AGCAGGCAGC 13390       13400       13410       13420       13430       13440
     TGGAAATAGG  AGATGAGCTC  TGGGAAAATG  CTCCCATCAC  CCTGGCCTGT  GTGCTGCCTG 13450       13460       13470       13480       13490       13500
     GGCGCACCCA  TTCAGGGCCC  TCCACGCAGC  CCACGCCCCT  GCCTCCTGAT  TCCTTCTAGG 13510       13520       13530       13540       13550       13560
     CTTCTCCAGC  ACTCGTGGGA  TGCCCAGATG  TGATCAGGGA  AGGGCTTGAG  GATGCAGGGA 13570       13580       13590       13600       13610       13620
     AGCTGTGGCT  GAGAGCCCTA  AACACACACA  TGCACACGCA  CACACACATA  CACAGGCACA 13630       13640       13650       13660       13670       13680
     TGCACACACG  ACCATACACA  CACACAAATG  CACGCAGATG  CACACAAATG  CATATGCACG 13690       13700       13710       13720       13730       13740
     CACACAAATG  CATATGCACA  CACACACATG  CACACATATG  CATACACGTA  TCCCTTTCAG 13750       13760       13770       13780       13790       13800
     TGGCTTTCCT  TTCTGTCCTT  AACCCTTGGC  CCCTTACAGT  GAGCTCCCAG  TTCTCCCCAG 13810       13820       13830       13840       13850       13860
     CCTTAGAACC  AAACCCTGGG  GCTGGGCTGG  GAGCCCCAG   TGACCCTCTG  TGTCTCTGTA 13870       13880       13890       13900       13910       13920
     GGTGGATGCA  CCCTTGGTCC  TGGTGCCAGC  TGCCACTGCA  GGCTGAAGGC  CTGTGAGTGT
```

Fig. 19N

```
         13930      13940      13950      13960      13970      13980
GACAAGCAAT CCGTGCACTG CTTCAAAGAG AGCCTGCCCA CCTATGAGAA AAACTTCAAG
                    Exon 4

13990      14000      14010      14020      14030      14040
CAGTTCTCCA GCCGGCCCAG GTGTGGCAGA CATAAGCCCT GGTGCTAGGG ACACCACAGG 14050      14060      14070      14080      14090      14100
GTCCCTCTCA TCATCCAGCA TCCGCTCTAG TGTTGCTCTT CCAGGAAGCC TTCTCAGATC 14110      14120      14130      14140      14150      14160
ATCCCCAACA GGCCCCTGTT CTTCCACTGG GAGGGAGGAC AAAATGTCTC CCGCAGGGCA 14170      14180      14190      14200      14210      14220
GCTCACCCTT CAGCATTCTG ACCAAGGGGA CTCCCTGTCG TTCAGCATCA GAGGGCTGGA 14230      14240      14250      14260      14270      14280
GAGCAGAAAT GGGAAAGATG AGATGCCTGC CCTGCAGGAG CTGGCATTCT GTGGAGTGGG 14290      14300      14310      14320      14330      14340
GAGGACTACA AATGCATGGA TATAGAAGTA AGAGACACAT TAGACTGTAG TAAGTGCTAT 14350      14360      14370      14380      14390      14400
GATGCAGTAA AACAAAGGGA CGGGATAGAG ATGCACCCAA CCCCACATCC CAGGGGTTTC 14410      14420      14430      14440      14450      14460
CAGGAGGGGA GAAGCCCCAG GATCTACCCC AAACTCTCTC TTCACCCCCA CTGCAAACCG 14470      14480      14490      14500      14510      14520
GGACACAGAG CAGACTTGAG CGCCAGGCCC ATGCCCAGCT CTAGCTGGCA ACAAAGCCAC 14530      14540      14550      14560      14570      14580
CACTTTCCTT GCCCCTCTGC GTCCTCAGTT TTTATGATGT CATTCTTAGC TTTTCTTATC 14590      14600      14610      14620      14630      14640
AAGAGGCAGA ATCTGTTTTC CCCATCCCAT GAATCTGAAC TGGTCTTGTG GCTTAGTTTG 14650      14660      14670      14680      14690      14700
GTCAATAGAA TGTTGTGGGA GGGATGGTTT ACCAGTTTTG AGCTAGGCCT CAGGAGGTCT 14710      14720      14730      14740      14750      14760
AGGGCATGTC TACTCTCTCT TAGGACAGCT GCCCCCACCC TGCAAAAAAG CCTGGGCTAG 14770      14780      14790      14800      14810      14820
CCTGCTGGAG GATGAGAGCC CACCTGGATC AGTTGTCTCA GCTGATTTCA GACACGTGAG 14830      14840      14850      14860      14870      14880
AGAGAGCTCA GCGAGACTCA GCTTGTAGCT GACTACAGAT GTGTGAGGGA ACCTGGCTGA 14890      14900      14910      14920      14930      14940
GACCAAAACA ACTGTCCAGC TGAGCCCAGG CTAAACTGCC AACATGCAGA ATTGTGAGCT 14950      14960      14970      14980      14990      15000
AAATAAAGGC TGCTGTTCTA AGTCACTGGG TTTTGGTATG GTTTGTTAGG CAGCCATAAC
```

Fig. 19O

```
       15010       15020       15030       15040       15050       15060
   TAACAGGTGT  AATTGGTCCT  TATTCCCTTA  TTCACTGAGA  GTGATGGGTT  CTCAGCCCTG 15070       15080       15090       15100       15110       15120
   AGCTGGACTT  GGAGGCCATG  GAAATGCAGT  GGACATGGCC  TTTGTTCCTT  ACCTTGAAGC 15130       15140       15150       15160       15170       15180
   TGTGGAAGGA  GGTCAAGTTC  ATGGAATAAT  GGAGAACACA  CAGCTGTAAT  CGTTTGCTTG 15190       15200       15210       15220       15230       15240
   TTCAGGGAAC  ACACATTTAT  TGAGCACTTG  CTATGTGCCA  GGCACAGTGC  CAGGCAGTAG 15250       15260       15270       15280       15290       15300
   GGATCCAGAT  ATTTAAAGAA  AACAAACAAA  AATCAGGTCC  AAAACTCCTG  GGGAGAATGC 15310       15320
   TGAGAGTGGT  ATCAGCTTTT  AGGAATTC
```

Fig. 20
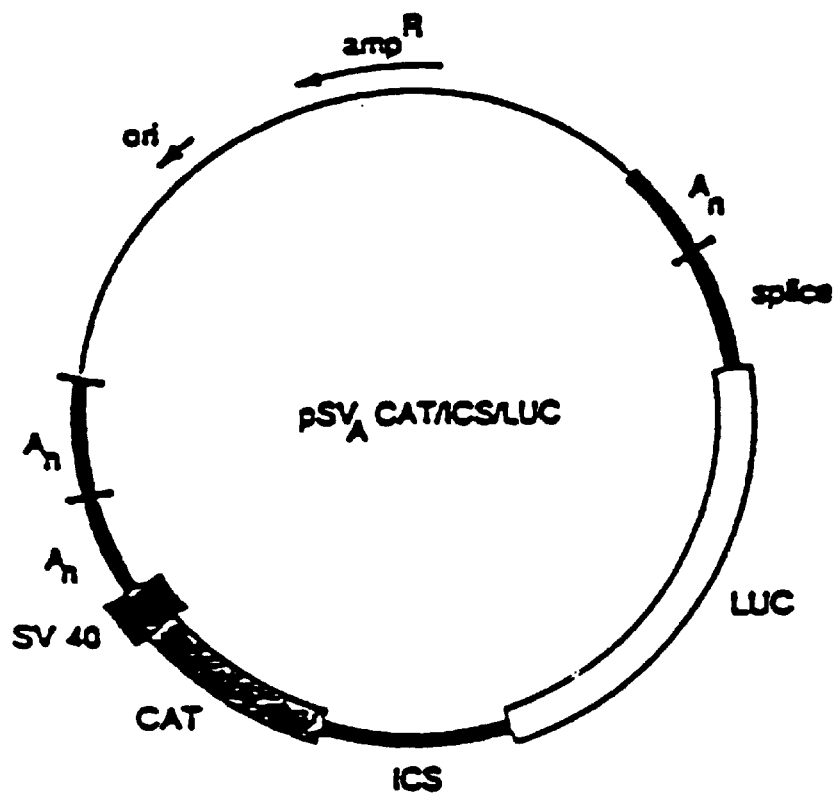
RNA:

Fig. 22

```
          1                       Ca++
H I       AVWQFRKMIK CVIPGSDPFL EYNNYGCYCG LGGSGTPVDE LDKCCQTHDN
H II      NLVNFHRMIK -LTTGKEAAL SYGFYGCHCG VGGRGSPKDA TDRCCVTHDC
H IV      GLLDLKSMIE -KVTGKNALT NYGFYGCYCG WGGRGTPKDG TDWCCWAHDH
R IV      GLLELKSMIE -KVTGKNAVK NYGFYGCYCG WGGHGTPKDG TDWCCRMHDR
R III     SFWQFQRMVK -HITGRSAFF SYYGYGCYCG LGGRGIPVDA TDRCCWAHDC
               .              **   **  *           *  **   **
               9              25   29  32          42 44   48
                              26   30                 45   49

51         ELAPID LOOP
H I       CYDQAKKLDS CKFLLDNPYT HTYSYSCSGS AITCS---SK NKECEAFICN
H II      CYKRLEKR-G C-----GTKF LSYKFSNSGS RITCA----K QDSCRSQLCE
H IV      CYGRLEEK-G C-----NIRT QSYKYRFAWG VVTCE----P GPFCHVNLCA
R IV      CYGLLEEK-H C-----AIRT QSYDYRFTQD LVICE----H DSFCPVRLCA
R III     CYHKLKEY-G C-----QPIL NAYQFAIVNG TVTCGCTMGG GCLCGQKACE
          **                       *          *             *
          51                       73         84            99
           52
          101                            CARBOXY EXTENSION
H I       CDRNAAICFS KAP--YNKAH KNLDTKKY-C QS
H II      CDKAAATCFA RNKTTYNK-K YQYYSNKH-C RGSTPRC
H IV      CDRKLVYCLK RNLRSYNP-Q YQYFPNIL-C S
R IV      CDRKLVYCLR RNLWSYNR-L YQYYPNFL-C
R III     CDKLSVYCFK ENLATYEKTF KQLFPTRPQC GRDKLHC
          ++ *          *
          108        116
```

Alignment of amino acid sequences of mature Human (H) Type I, II and IV and Rat (R) Type III and IV PLA$_2$. Asterisks denote residues that have been conserved among all active PLA$_2$ sequences. The dot indicates a residue conserved in all active sequences, except the Rat Type III shown here. The + indicates residues conserved in all Type I and II enzymes known to date. The position numbers are indictated under the asterisks. The Elapid loop, Ca++ binding site, and carboxy extensions are also shown.

Fig. 27

```
                      1                                              46
RPLA2-Type  I    AVWQFRNMIKCTIPGSDPLREYNNYGCYCGLGGSGTPVDDLDRCCQ
RPLA2-Type  II   SLLEFGQMIL-FKTGKRADVSYGFYGCHCGVGGRGSPKDATDWCCV
RPLA2-8          SFWQFQRMVK-HITGRSAFFSYYGYGCYCGLGGRGIPVDATDRCCW
RPLA2-10         GLLELKSMIE-KVTGKNAVKNYGFYGCYCGWGGHGTPKDGTDWCCR
                          *                **  **  *          *  **

47                                             92
RPLA2-Type  I    THDHCYNQAKKLESCKFLIDNPYTNTYSYKCSGNVITCSDKNND--
RPLA2-Type  II   THDCCYNRLEKR-GC-----GTKFVTYKFSYRGGQISCS-TNQDS-
RPLA2-8          AHDCCYHKLKEY-GC-----QPILNAYQFAIVNGTVTCGCTMGGGC
RPLA2-10         MHDRCYGLLEEK-HC-----AIRTQSYDYRFTQDLVICEHDSF---
                    ** **                        *            *

93                                             137
RPLA2-Type  I    -CESFICNCDRQAAICF--SKVPYNKEYKDL-DTKKHC
RPLA2-Type  II   -CRKQLCQCDKAAAECFARNKKSYSLKY-QFYP-NKFC<u>KGKTPSC</u>
RPLA2-8          LCGQKACECDKLSVYCFKENLATYEKTFKQLFPTRPQC<u>GRDKLHC</u>
RPLA2-10         -CPVRLCACDRKLVYCLRRNLWSYNRLY-QYYP-NFLC
                       *           *              *
```

Alignment of amino acid sequences of rat Type I, II, RPLA₂-8 and RPLA₂-10 PLA₂s. Asterisks denote eighteen residues that have been conserved among all active PLA₂ sequences. Underscored residues denote the amino acid COOH-terminal extensions.

MAMMALIAN PHOSPHOLIPASE A₂ NUCLEOTIDE SEQUENCES LOW MOLECULAR WEIGHT AMINO ACID SEQUENCES ENCODED THEREBY ANTISENSE SEQUENCES AND NUCLEOTIDE SEQUENCES HAVING INTERNAL RIBOSOME BINDING SITES

This application is a continuation, of prior application Ser. No. 08/651,405, filed on May 22, 1996 now abandoned, which is a continuation of Ser. No. 08/097,354, filed on Jul. 26, 1993, now abandoned.

FIELD OF THE INVENTION

The present invention relates to novel mammalian phospholipase $A_2$ nucleotide sequences, low molecular, weight (approximately 14 KD) amino acid sequences encoded thereby, clones and vectors which include the mammalian phospholipase $A_2$ nucleotide sequences, antisense nucleotide sequences complementary to the genes and mRNA transcripts encoding for the phospholipase amino acid sequences, nucleotide sequences having internal ribosome binding sites which allow for internal initiation of mRNA cap-independent translation, and cell lines.

BACKGROUND

Phospholipase $A_2$s—phosphatide 2-acylhydrolase, EC 3.1.1.4 (hereinafter "$PLA_2$") constitute a diverse family of enzymes that hydrolyze the sn-2 fatty acyl ester bond of phosphogylcerides, producing free fatty acid and lysophospholipids. See Dennis, E. A. Phospholiphases. In: *The Enzymes*, edited by Boyer, P. New York: Academic Press, p. 307–353 (1983). Over the past two decades, $PLA_2$ activities have been purified and characterized from different tissues, cultured cells, and exudates from different mammals. See Rordorf, G. et al.: *J. Neuroscience*, 11:1829–1826 (1991); Seilhamer, J. J. et al.: *J. Biochem.*, 106:38–42 (1989); Langlais J. et al.: *Biocham. & Biophys. Res. Comm.*, 182:208–214 (1992); Murakami, M. et al.: *J. Biochem.*, 111:175–181 (1992); and Jordan, L. M. et al.: *J. Chromat.*, 597:299–308 (1992). These enzymes have been found to vary in molecular weight, optimal pH, $Ca^{2+}$ dependence, substrate specificity, and solubility.

To date, two classes of unrelated $PLA_2$s have been reported. One is a family of low molecular mass, approximately 14 kDa $PLA_2$s which are characterized by a rigid three dimensional structure maintained by disulfide bridges and a catalytic requirement for $Ca^{2+}$. The other is a high molecular mass, 82 kDa, intracellular $PLA_2$ found in the cytosolic subcellular fraction in the absence of calcium, but associated with cellular membranes at calcium concentrations from 0.1 to 10 $\mu$M. See Clark, J. D. et al.: *Cell*, 65:1043–1051 (1991) and Sharp, J. D. et al.: *J. Biol. Chem.*, 266:14850–14853 (1991). In addition, several $Ca^{++}$-insensitive $PLA_2$ activities are believed to exist, however, it is also believed that as yet none of the genes encoding such activities have been cloned.

In terms of structure, low molecular weight, e.g., about 14 kDa, $PLA_2$s rank among the best characterized enzymes. Complete primary sequences have been determined for more than 50 $PLA_2$s from organisms such as snakes, bees and humans. See Heinrikson, R. L.: *Methods in Enzymology*, 197:201–214 (1991); Davidson, F. F. et al.: *J. Mol. Evolution*, 31:228–238 (1990); and Dennis, E. A. Phospholiphases. In: *The Enzymes*, edited by Boyer, P. New York, Academic Press, p. 307–353 (1983). In all active 14 kDa $PLA_2$s, 18 amino acids are believed to be conserved. See Heinrikson, R. L.: *Methods in Enzymology*, 197:201–214 (1991) and Davidson, F. F. *J. Mol. Evolution*, 31:228–238 (1990). Based on selected structural determinants, the low molecular weight $PLA_2$s have been classified into two types. See Heinrikson, R. L. et al.: *J. Biol. Chem.*, 252:4913–4921 (1977). Type I enzymes have a disulfide bridge connecting cysteines between amino acids 11 and 77. In addition, there is an insertion of three amino acids between residues 54 and 56, the so-called elapid loop. The only identified mammalian Type I $PLA_2$s, see Seilhamer, J. J. et al.: *DNA*, 5:519–527 (1986) and Ohara, O. et al.: *J. Biochem.*, 99:733–739 (1986), are expressed mainly in the pancreas and function extracellularly in digestion. Type II $PLA_2$s, on the other hand, lack the disulfide bridge between amino acids 11 and 77, have carboxy-terminal (COOH-terminal) amino acid extensions which can vary in length, but are commonly seven amino acids in length, which typically terminate in a half-cysteine joined to Cys-50 near the catalytic site His-48. The mammalian Type II $PLA_2$s reported to date occur in trace amounts in several tissues such as liver and spleen and are secreted from various cells in response to appropriate stimuli. See Seilhamer, J. J. et al.: *J. Biol. Chem.*, 264:5335–5338 (1989); Kramer, R. M. et al.: *J. Biol. Chem.*, 264:5768–5775 (1989); Komada, M. et al.: *J. Biochem.*, 106:545–547 (1989); Kusunoki, C. et al.: *Biochimica Et Biophysica Acta*, 1087:95–97 (1990); Aarsman, A. J. et al.: *J. Biol. Chem.*, 264:10008–10014 (1989); Ono, T. et al.: *J. Biol. Chem.*, 264:5732–5738 (1988); Horigome, K. et al.: *J. Biochem.*, 101:53–61 (1987); Nakano, T. et al.: *Febs. Letters*, 261:171–174 (1990); and Schalkwijk, C. et al.: *Biochem. & Biophys. Res. Comm.*, 174:268–272 (1991). It is believed that Type II $PLA_2$s are associated with the pathologies of several diseases involving infection, tissue damage, and inflammation, such as acute pancreatitis, septic shock, peritonitis and rheumatoid arthritis. See Vadas, P. et al.: *Lab. Invest.*, 55:391–404 (1986); Pruzanski, W. et al.: *Advances in Exper. Med. & Biol.*, 279:239–251 (1990); Uhl, W. et al.: *J. Trauma*, 30:1283–1290 (1990); and Malfertheiner, P. et al.: *Klinische Wochenscrift*, 67:183–185 (1989). Mammalian Type I and II $PLA_2$s share approximately 30–40% amino acid homology; however, eighteen amino acids are invariantly conserved in all known functional $PLA_2$s. Type I mammalian $PLA_2$ genes contain 4 coding exons; Type II mammalian genes contain five exons, the first of which is noncoding.

In 1990, a distinct 120 bp putative $PLA_2$ exon-like fragment (h10a), homologous to the amino-terminus encoding region of known $PLA_2$s, was obtained by screening a human genomic DNA library with a 45 bp human $PLA_2$ Type II oligonucleotide probe. See Johnson, L. K. et al.: *Advances in Exper. Med. & Biol.*, 275:17–34 (1990). Zoo blots indicated that the putative exon has been highly conserved during evolution. However, additional exons indicating the presence of a complete gene, a corresponding cDNA, or evidence of transcription in different human tissues was not found.

Neuronal ceroid lipfuscinoses (NCL), or Batten disease, are terminal, inheritable, lysosomal storage diseases of children. They are characterized by the accumulation of an autofluorescent pigment (ceroid or lipofuscin) in cells, especially neurons and epithelial pigment cells of the retina. NCL patients typically manifest high levels of the highly reactive compound, 4-hydroxynonenal. These levels are believed to be a consequence of a failure to resolve peroxidized, fatty acids in the normal way. It is believed that this failure could be the result of a phospholipase $A_2$ defect.

The infantile form of NCL has now been linked to chromosome 1p33-35. See Jarvela, I. et al.: *Genomics*, 9:170–173 (1991). The non-pancreatic $PLA_2$ (Type II) has also been mapped to chromosome 1. The Type II gene and two additional putative exon-like "fragments" (h8 and h10a), see Johnson, L. K. et al.: *Advances in Exper. Med. & Biol.*, 275:17–34 (1990), are located at about 1p34—in the middle of the region where gene for infantile NCL is believed to reside. See Jarvala, I. et al.: *Genomics*, 9:170–173 (1991). h8 and h10a each contain a unique sequence which is highly homologous to, but distinct from, exon two (which contains the calcium binding domain) of $PLA_2$ Type II.

Consequently, there is a continuing need to further identify and characterize additional $PLA_2$ exons if such exist. Such exons could be part of unidentified genes. To the extent there are additional unidentified $PLA_2$ exons and genes, they may encode proteins (enzymes) that function in a manner different from, similar to, or overlapping with, the known $PLA_2$s. Moreover, such unidentified exons and/or genes and the enzymes encoded thereby may be regulated by some of the same effectors as the known $PLA_2$ genes and their proteins. Investigation of these unidentified exons and/or genes and their encoded enzymes may therefore result in new approaches to therapy of $PLA_2$-related diseases, such as Batten disease and inflammatory disease. Alternatively, these unidentified enzymes may have entirely different physiologic and pathologic functions. Thus, therapeutic approaches designed to block the activity of the known Type II $PLA_2$ enzymes may also block or reduce the activity of these novel enzymes, thereby producing unexpected side effects. Still further, a better understanding of the regulation of expression of the known and unidentified Type II $PLA_2$ genes in different tissues will likely expand the overall understanding of the biology and metabolic processes involving $PLA_2$s.

SUMMARY OF THE INVENTION

In brief, the present invention overcomes certain of the above-mentioned shortcomings and drawbacks associated with the present state of the $PLA_2$ art through the discovery of a novel family of mammalian $PLA_2$ genes or nucleic acid sequences encoding low molecular weight amino acid sequences, clones, vectors, antisense nucleotide sequences, nucleotide sequences having internal binding sites, and cell lines.

More particularly, the low molecular weight, i.e., about 14 kDa, amino acid sequences encoded by the novel family of mammalian $PLA_2$ genes or sequences of the present invention may be generally characterized as enzymes having esterase activity specific for the acyl group at the sn2 position of glycero-phospholipids. Moreover, the novel amino acid sequences of the present invention do not include disulfide bridges between cysteine amino acids 11 and 77 and elapid loops. Still further, the novel amino acid sequences of the present invention may in some instances include COOH-terminal amino acid extensions which can vary in length. In addition, because of the difference in the number of cysteine residues in the encoded amino acid sequences, those novel $PLA_2$s of the present invention that include 16 cysteine amino acid residues have been designated as Type III whereas those novel Type IV $PLA_2$s of the instant invention include 12 cysteines and have been designated at Type IV. Exemplary of Type III $PLA_2$s of the present invention are the genes identified as $RPLA_2$-8 (rat) and partial $HPLA_2$-8 (human), as well as the $RPLA_2$-8 (rat) cDNA. Examples of Type IV $PLA_2$s of the present invention are the cDNAs identified as $RPLA_2$-10 (rat) and $HPLA_2$-10 (human).

In accordance with the present invention, a human $PLA_2$-encoding cDNA, which expresses $HPLA_2$-10, see FIG. 12, has been isolated from human brain RNA by RACE-PCR technique. The $HPLA_2$-10 cDNA also has been isolated from a human stomach cDNA library. In addition, two rat $PLA_2$ encoding cDNAs, designated $RPLA_2$-8 (FIG. 3) and $RPLA_2$-10 (FIG. 11), have been isolated from rat brain and heart cDNA libraries, respectively. The $RPLA_2$-10 is believed to be the counterpart of the $HPLA_2$-10. $RPLA_2$-10 and $HPLA_2$-10 share about 79% and 78% homology at the open reading frame nucleic acid and amino acid sequence levels, respectively. The mature enzyme encoded by the $HPLA_2$-10 clone has a calculated molecular weight of about 13,592, whereas the mature enzyme encoded by the $RPLA_2$-8 clone has a calculated molecular weight of about 14,673. As indicated, a partial human genomic counterpart to $RPLA_2$-8, $HPLA_2$-8 genomic DNA, has been isolated. See FIG. 19.

Comparison of the $RPLA_2$-8 amino acid sequence deduced from the cDNA sequence to Type I and Type II $PLA_2$s is shown in FIGS. 8 and 9. The significant structural features of the $RPLA_2$-8 protein are summarized in TABLE I. Seventeen (17) of the eighteen (18) absolutely conserved amino acids in all active 14 kDa $PLA_2$s are conserved in $RPLA_2$-8. $RPLA_2$-8 protein does not contain either a disulfide bridge between Cysteines 11 and 77 or an elapid loop, which are both characteristic of Type I $PLA_2$s. $RPLA_2$-8 protein, however, does include a seven amino acid COOH-terminal extension having the sequence GRDKLHC, as shown in FIG. 27, which is a characteristic of Type II $PLA_2$s as evidenced in FIGS. 22 and 27. Furthermore, unlike mammalian type I and II $PLA_2$s which have 14 cysteine amino acid residues, $RPLA_2$-8 protein includes 16 cysteine amino acid residues. It is therefore believed that $RPLA_2$-8 encodes a novel $PLA_2$, which has been designated as $PLA_2$ Type III.

The cDNAs of $RPLA_2$-10 and $HPLA_2$-10 are 1.8 kb (FIG. 11) and 1.1 kb (FIG. 12), respectively. A comparison between the deduced amino acid sequences from $RPLA_2$-10 and $HPLA_2$-10 is shown in FIG. 13. FIGS. 14 and 15 are comparisons between the $HPLA_2$-10 deduced amino acid sequence and those of Type I and II human $PLA_2$s, respectively. FIGS. 18 and 16 are comparisons between the $RPLA_2$-10 deduced amino acid sequence and those of Type I and II rat $PLA_2$s, respectively. A comparison between the deduced amino acid sequences from $RPLA_2$-10 and $RPLA_2$-8 is shown in FIG. 17. The major structural features of human and rat $PLA_2$-10 deduced amino acid sequences are listed in TABLE I. All eighteen (18) conserved amino acids in all of the active low-molecular weight, approximately 14 kDa, $PLA_2$s are conserved in both human and rat $PLA_2$-10 amino acid sequences of the present invention. Like the predicted $RPLA_2$-8 amino acid sequence, human and rat $PLA_2$-10 amino acid sequences also lack disulfide bridges between Cys-11 and 77 and elapid loops. However, $PLA_2$-10 amino acid sequences are believed to differ from $RPLA_2$-8 protein by having twelve (12) cysteine residues instead of sixteen (16). They further differ from $RPLA_2$-8 in that $RPLA_2$-10 does not have a COOH-terminal amino acid extension as depicted in FIG. 27 and $HPLA_2$-10 has only a single serine amino acid COOH-terminal extension as illustrated in FIG. 22. The $PLA_2$-10 proteins of the present invention have therefore been designated, as mentioned hereinbefore, as $PLA_2$ Type IV.

The present invention also contemplates antisense nucleotide sequences which are complementary to the genes and mRNA transcripts which encode for the Type III and Type IV PLA$_2$s. Exemplary of antisense sequences in accordance with the present invention are those which are complementary to the entire or portions of the nucleotide sequences set forth in FIGS. 3, 11, 12 and 19. It should therefore be understood that the present invention contemplates any antisense nucleotide sequence which may be useful in connection with inhibiting or interfering with the expression of the Type III and Type IV PLA$_2$ enzyme genes and mRNA transcripts therefor.

The above features and advantages will be better understood with reference to the FIGS., Detailed Description and Examples which are set out hereinbelow. It should be understood that the biological materials of this invention are exemplary only and are not to be regarded as limitations of this invention.

BRIEF DESCRIPTION OF THE FIGS.

Reference is now made to the accompanying FIGS. in which are shown characteristics corresponding to the novel mammalian 14 KD PLA$_2$s of the present invention from which certain of their novel features and advantages will be apparent:

FIG. 3 depicts the RPLA$_2$-8 cDNA (SEQ ID: NO: 21) and derived amino acid sequence (SEQ ID NO: 22) (the first and last eight (8) nucleotides are cloning linkers);

FIG. 5 is a comparison between HPLA$_2$-8 Exon I (SEQ ID NO: 23) and RPLA$_2$-8 Exon I (SEQ ID NO: 24) sequences;

FIG. 6 is a comparison between HPLA$_2$-8 Exon II (SEQ ID: NO: 25) and RPLA$_2$-8 Exon II (SEQ ID NO: 26) sequences;

FIG. 7 is a comparison between HPLA$_2$-8 Exon IV (SEQ ID NO: 27) and RPLA$_2$-8 Exon IV (SEQ ID NO: 28) sequences;

FIG. 8 is a comparison of RPLA$_2$-8 deduced amino acid sequence (SEQ ID NO: 22) and rat PLA$_2$ Type I amino acid sequence (SEQ ID NO: 34);

FIG. 9 is a comparison of the RPLA$_2$-8 deduced amino acid sequence (SEQ ID NO: 22) and rat PLA$_2$ Type II amino acid sequence (SEQ ID NO: 34);

FIG. 11 depicts the RPLA$_2$-10 cDNA sequence (SEQ ID: NO: 29) and derived amino acid sequence (SEQ ID NO: 30) showing primary cDNA sequence and various primer sequences, which are used in sequencing and synthesis, are underlined;

FIG. 12 depicts the HPLA$_2$-10 cDNA (Type IV) sequence (SEQ ID: NO: 31) and derived amino acid sequence (SEQ ID NO. 32) and a secondary (clone HPLA$_2$10–5) cDNA sequence which is slightly different at the 5' end and forshortened. Various primer sequences used in sequencing and synthesis are underlined.

FIG. 13 is a comparison between deduced amino acid sequences of HPLA$_2$-10 (SEQ ID NO: 32) and RPLA$_2$-10 (SEQ ID NO: 30);

FIG. 14 is a comparison between HPLA$_2$-10 deduced amino acid sequence (SEQ ID NO: 32) and human Type I amino acid sequence (SEQ ID NO: 36);

FIG. 15 is a comparison between HPLA$_2$-10 deduced amino acid sequence (SEQ ID NO: 32) and human PLA$_2$ Type II amino acid sequence (SEQ ID NO: 37);

FIG. 16 is a comparison between deduced amino acid sequences of RPLA$_2$-10 (SEQ ID NO: 30) and rat PLA$_2$ Type II amino acid sequence (SEQ ID NO: 35);

FIG. 17 is a comparison between deduced amino acid sequences of RPLA$_2$-10 (SEQ ID NO: 30) and RPLA$_2$-8 (SEQ ID NO: 22);

FIG. 18 is a comparison between deduced amino acid sequence of RPLA$_2$-10 (SEQ ID NO: 30) and rat PLA$_2$ Type I amino acid sequence (SEQ ID NO: 34);

Figure 21:
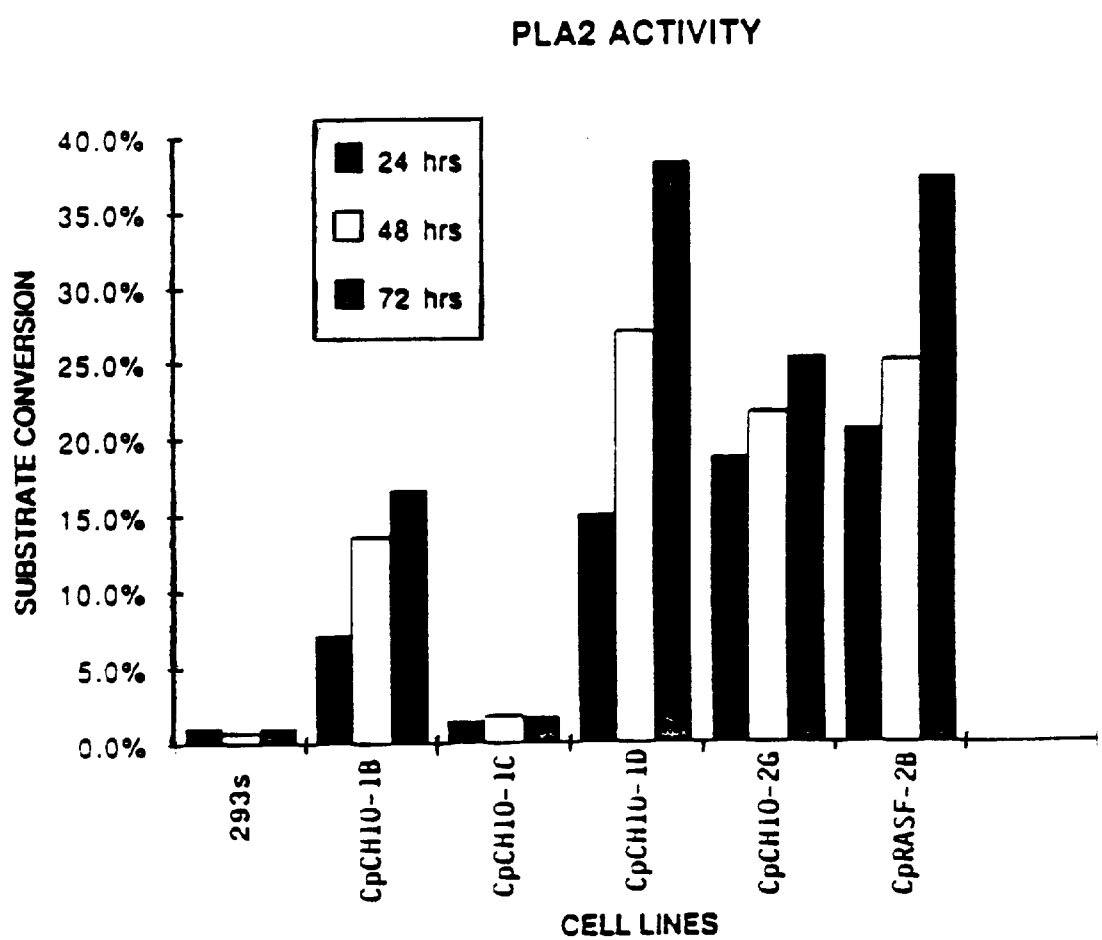

FIG. 19 depicts the partial human genomic HPLA$_2$-8 DNA sequence (SEQ ID NO: 33). Putative exon 1 and exons 2 and 4 are underlined;

FIG. 20 depicts a diagram of the vector to express discistronic mRNA. The chloramphenicol acetyl transferase and luciferase reporter genes are indicated by boxes. The intercistronic sequence that is replaced by part of RPLA$_2$-8 is shown;

FIG. 21 illustrates PLA$_2$ activity of expressed HPLA$_2$-10 cDNA. pCH10 is HPLA$_2$-10 cDNA cloned into an Epstein Barr virus-based expression vector. CpCH10-1B, CpCH10-1C, CpCH10-1D and CpCH20-2G are independent cell lines which express plasmid pCH10. The CpRASF-2B is a cell line which expresses plasmid pRASF into which a known human PLA$_2$ Type II gene has been cloned.

Figure 23:
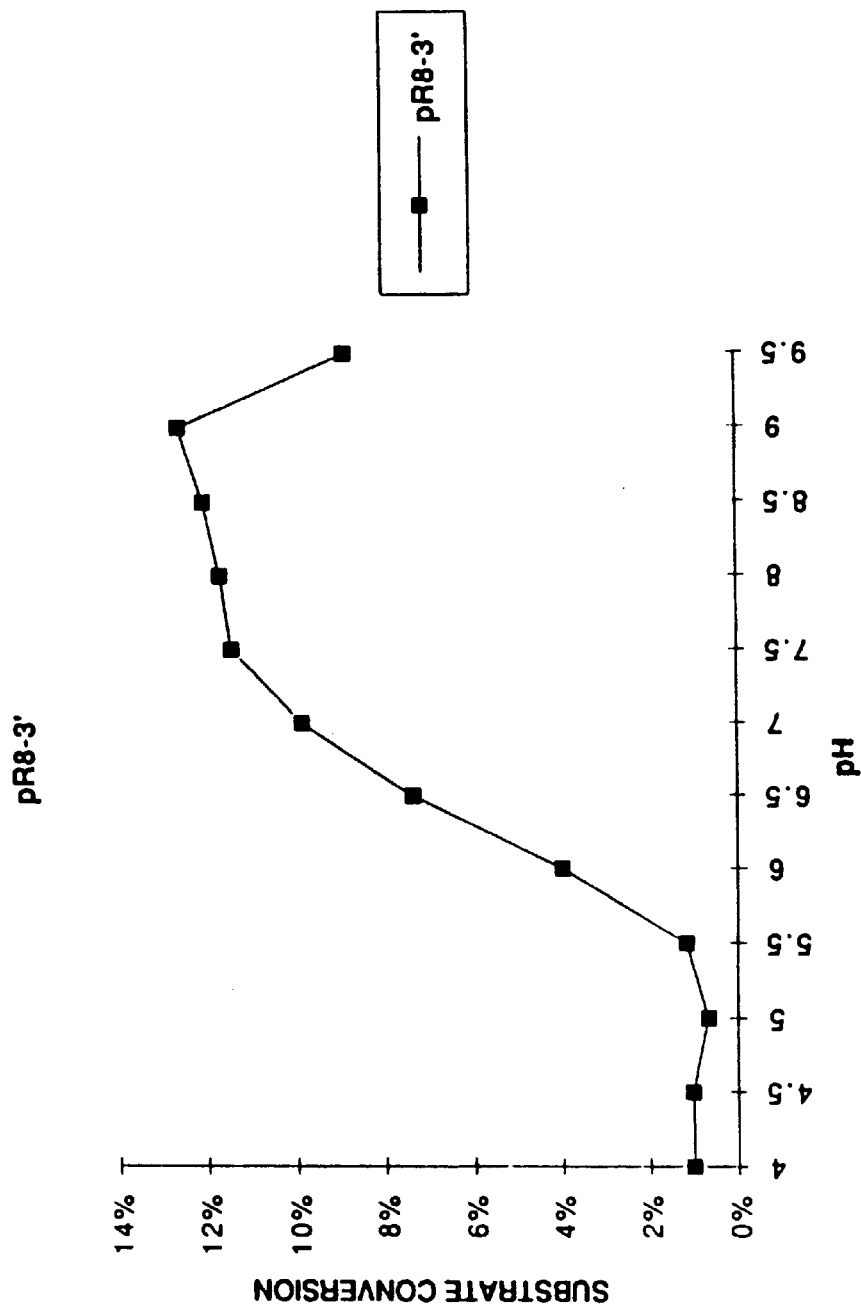
Figure 24:
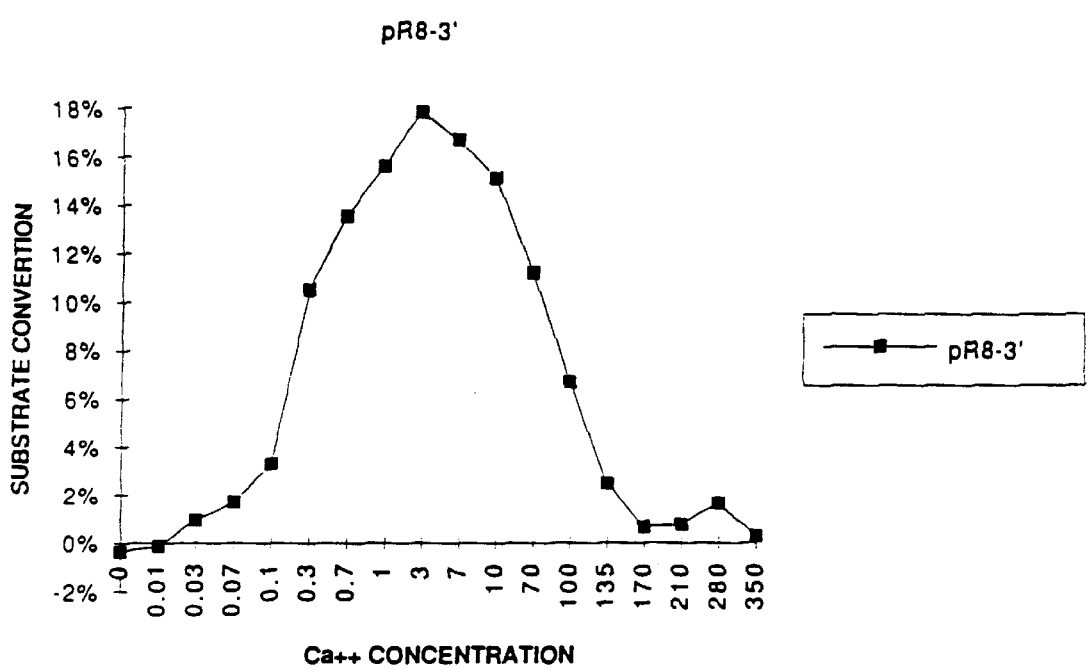
Figure 25:
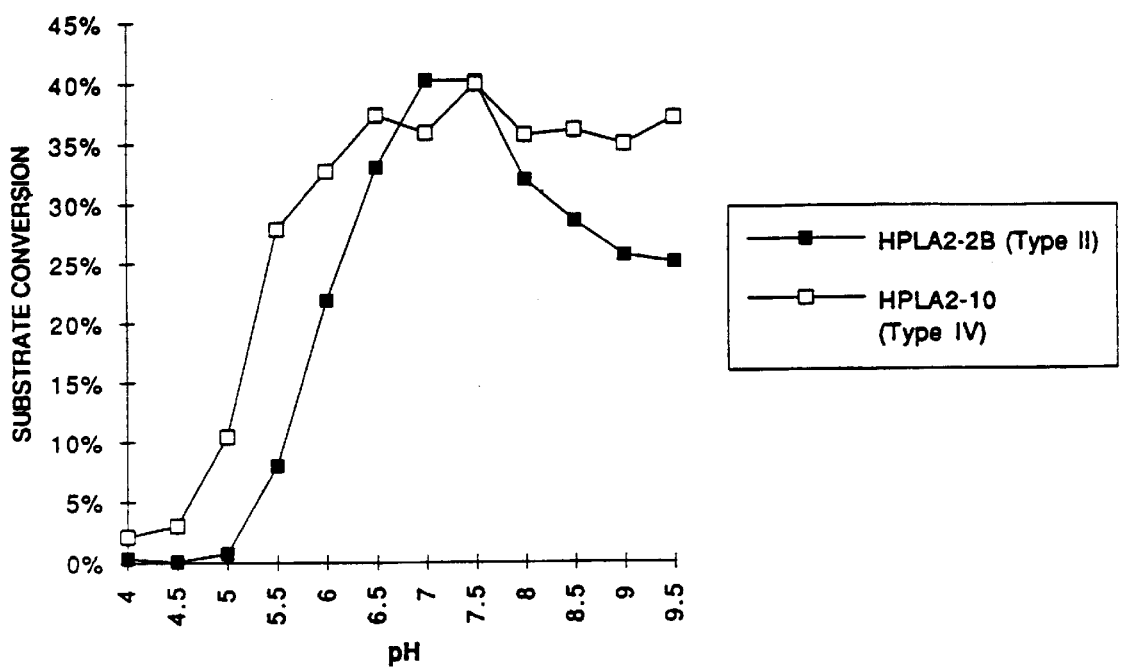

FIG. 22 depicts an alignment of amino acid sequences of human (SEQ ID Nos. 38, 19, 40, 44, and 43). Asterisks denote eighteen residues that have been conserved among all active PLA$_2$ sequences. The COOH-terminal amino acid extensions have been underscored;

FIG. 23 depicts the effects of pH on PLA$_2$ activity of RPLA$_2$-8 encoded enzyme (Type III). More particularly, FIG. 23 depicts the effects of pH on PLA$_2$ activity of RPLA$_2$-8 enzyme expressed by cell line CpR8-3'. The CpR8-3' cell line expresses plasmid pR8-3' which includes the coding region for the mature RPLA$_2$-8 protein (bases 806–1200) which is preceded by the signal peptide of PRASF (bases 131–196). Assay for PLA$_2$ activity is as indicated herein and in Elsbach, P. et al.: *Methods in Enzymology*, 197:24–31(1991);

FIG. 24 depicts the effects of calcium on PLA$_2$ activity of RPLA$_2$-8 encoded enzyme (Type III). More particularly, FIG. 24 depicts the effects of calcium on PLA$_2$ activity of RPLA$_2$-8 enzyme expressed by cell line CpR8-3'. The CpR8-3' cell line expresses plasmid pR8-3' which includes the coding region for the mature RPLA$_2$-8 protein (bases 806–1200) which is preceded by the signal peptide of pRASF (bases 131–196). Assay for PLA$_2$ activity is as indicated herein and in Elsbach, P. et al.: *Methods in Enzymology*, 197:24–31(1991);

FIG. 25 depicts the effects of pH on PLA$_2$ activity of HPLA$_2$-10 encoded enzyme (Type IV). More particularly, FIG. 25 depicts the effects of pH on PLA$_2$ activity of PLA$_2$ Type II enzyme expressed by cell line CpRASF-2B and of PLA$_2$ Type IV enzyme expressed by cell line CpCH10-1D. The CpRASF-2B cell line expresses plasmid pRASF into which a known human PLA$_2$ Type II gene has been cloned.

Figure 26:
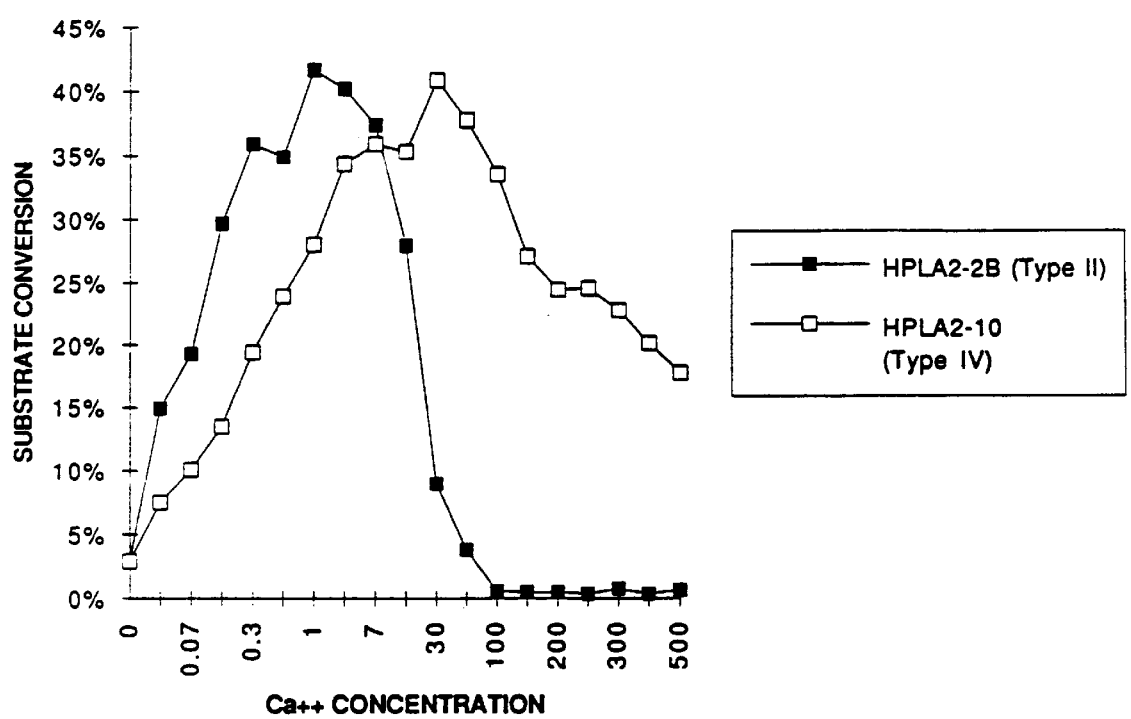

The CpCH10-1D cell line expresses plasmid pCH10 into which the HPLA$_2$-10 cDNA has been cloned. Assay for PLA$_2$ activity is as indicated herein and in Elsbach, P. et al.: *Methods in Enzymology*, 197:24–31 (1991);

FIG. 26 depicts the effects of calcium on PLA$_2$ activity of HPLA$_2$-10 encoded enzyme (Type IV). More particularly, FIG. 26 depicts the effects of calcium on PLA$_2$ activity of PLA$_2$ Type II enzyme expressed by cell line CpRASF-2B and of PLA$_2$ Type IV enzyme expressed by cell line CpCH10-1D. The CpRASF-2B cell line expresses plasmid PRASF into which a known human PLA$_2$ Type II gene has been cloned. The CpCH10-1D cell line expresses plasmid pCH10 into which the HPLA$_2$-10 cDNA has been cloned. Assay for PLA$_2$ activity is as indicated herein and in Elsbach, P. et al.: *Methods in Enzymology*, 197:24–31 (1991); and FIG. 27 depicts an alignment of amino acid sequences of rat Types I, II, RPLA$_2$-8 and RPLA$_2$-10 PLA$_2$s (SEQ ID Nos. 41, 42, 43, 44). Asterisks denote eighteen residues that have been conserved among all active PLA$_2$ sequences. The COOH-terminal amino acid extensions have been underscored.

DETAILED DESCRIPTION

By way of illustrating and providing a more complete appreciation of the present invention and many of the attendant advantages thereof, the following detailed description is provided concerning the novel mammalian PLA$_2$ nucleotide sequences, the low molecular weight amino acid sequences encoded thereby, clones, vectors, antisense nucleotide sequences, nucleotide sequences having internal ribosome binding sites, and cell lines.

Figure 1:
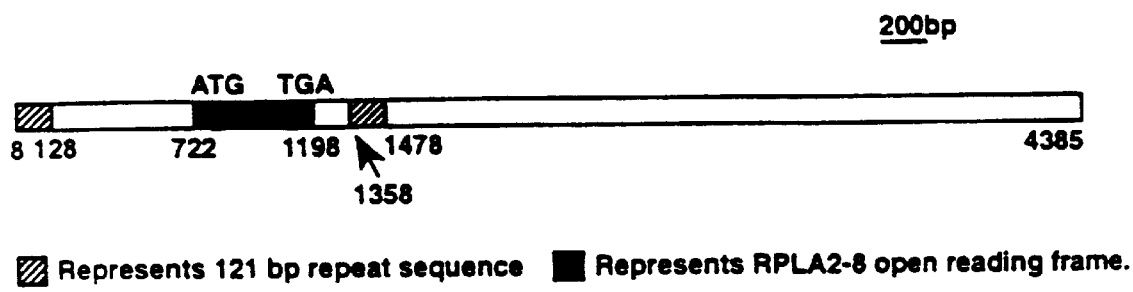
FIG. 1 depicts a diagram of RPLA$_2$-8 cDNA showing positions of open reading frame coding region, repeats, and 5' and 3' termini (the first and last eight (8) nucleotides are cloning linkers)
Figure 2:
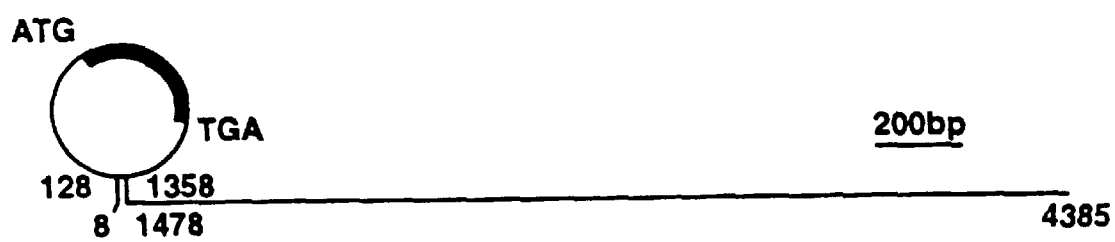
FIG. 2 depicts a postulated secondary structure of RPLA$_2$-8 cDNA showing a stem and a loop containing the open reading frame coding region.

In accordance with the present invention, a 4.4 kb cDNA containing the r8 fragment, a rat genomic fragment containing sequences homologous to h8 fragment, is isolated from a rat fetal brain cDNA library. See FIG. 1. This cDNA is about five-times larger than any mammalian PLA$_2$ cDNA known to date. Uniquely, the entire coding region is contained on a putative 1 kb loop flanked by 121 bp inverted perfect repeats, leaving about a 3 kb 3' "tail." See FIG. 2. The sequence of the entire cDNA is shown in FIG. 3. The size of the gene is about 15 kb. See FIG. 4. A preliminary screen of some rat tissues by reverse transcription and PCR (RT-PCR), using primers Pla8-1 and Pla8-4, reveals the pattern of RPLA$_2$-8 gene expression indicated in Table I.

TABLE I

Structure Features of Type III and IV PLA$_2$

| | Pre* | Pro* | Mature* |
|---|---|---|---|
| Hum Type I | MKLLVLAVLLTVAAA[1] | DSGISPR[2] | AVWQF[3] |
| Hum Type II | MKTLLLAVIMIFGLLQAHG[4] | | NLVNF[5] |
| Rat Type I | MDLLVSSGMKGIAVFLVFIFC[6] | (WTTSTLS)[7] | SFWQF[8] |

TABLE I-continued

| | | |
|---|---|---|
| Hum Type III | MKGLLPLAWFLACSVPAVQG[9] | GLLDL[10] |
| Rat Type IV | MKRLLTLAWFLACSVPAVPG[11] | GLLEL[12] |

Other Sequence Features of Nature Type III and Type IV PLA$_2$

| Rat Type III | Human and Rat Type IV |
|---|---|
| Conserved Structures of the Mature Peptides: | |
| Phe5 | Ile9 |
| Met8 | Met8 |
| YGCYCG Ca$^{2+}$ binding loop | YGCYCG Ca$^{2+}$ binding loop |
| His48, Asp49 active site | His48, Asp49 active site |
| Position of Cys residues (disregarding the two extra Cys residues) | Position of Cys residues (disregarding the two missing Cys residues) |
| Unusual Features of the Mature Peptides: | |
| Val9 | Leu5 |
| Two extra Cys residues | Two missing Cys residues |
| Ala 102, 103 missing | Ala 102, 103 missing |
| Unusually large variable peptide loop | |
| Other Characteristics of Pre, Pro and Mature Peptides: | |
| No elapid loop | No elapid loops |
| No disulphide bridge between Cys 11 and 77 | No disulphide bridges between Cys 11 and 77 |
| Sixteen Cys residues | Twelve Cys residues |
| Seven COOH-terminal amino acid extension-GRDKLHC | Human Type IV-one serine COOH-terminal extension Rat Type IV-no COOH-terminal amino acid extension |

Comment:
Human Type I PLA$_2$ has a 7 residue propeptide, human Type II does not. Human and rat Type IV appear more like Type II; Rat Type III might encode a 7 residue propeptide.
*represents the amino acid sequence for the respective prepeptides and propeptides and the initial amino acid sequence of the mature peptides.
[1]represents SEQ ID NO: 1:; [2]represents SEQ ID NO: 2:; [3]represents SEQ ID NO: 3:; [4]represents SEQ ID NO: 4:; [5]represents SEQ ID NO: 5:; [6]represents SEQ ID NO: 6:; [7]represents SEQ ID NO: 7: [8]represents SEQ ID NO: 8:; [9]represents SEQ ID NO: 9:; [10]represents SEQ ID NO: 10:; [11]represents SEQ ID NO: 11:; [12]represents SEQ ID NO: 12:.
**The numbers designating the positions for the amino acids in Table I are for the mature peptides.

Moreover, according to Northern Blot data of several tissues, a RPLA$_2$ mRNA is detected in only the testis indicating that the RPLA$_2$-8 gene is testis specific, as reported in Table II.

TABLE II

Northern blot data

| | Type IV (cl 10) human |
|---|---|
| brain | – |
| heart | +++ |
| kidney | – |
| liver | – |
| lung | + |
| pancreas | – |
| placenta | ++ |
| skeletal muscle | – |
| spleen | – |
| testis | – |

| | Type IV (cl 10) rat | Type III (cl 8) rat |
|---|---|---|
| brain | – | – |
| heart | ++ | – |

TABLE II-continued

Northern blot data

| | | |
|---|---|---|
| kidney | − | − |
| liver | − | − |
| lung | ? | − |
| skeletal muscle | − | − |
| spleen | − | − |
| testis | − | ++ |

Using parts of RPLA$_2$-8 as probes, a partial human genomic clone which is homologous to rat genomic clone is identified. See FIG. 19. To date, all but the third of the four exons in the human genomic DNA, see FIGS. 5–7, is identified and sequenced. The 3' flanking regions of the human and rat genes show very significant homology (about 50 percent) for about 500 bp. This conservation is unusual and suggests functional importance. It is functionally demonstrated that RPLA$_2$-8 cDNA contains an internal ribosome binding site that enables internal translation initiation.

A comparison of the significant structural features of the putative protein encoded by RPLA$_2$-8 cDNA sequence and encoded amino acid sequence to those of the corresponding pancreatic and non-pancreatic PLA$_2$ enzymes are shown in FIG. 8 and 9. Pancreatic PLA$_2$ is known as Type I and the non-pancreatic PLA$_2$ is designated as Type II. It is believed that PLA$_2$-8 encodes a novel PLA$_2$ which is designated as Type III. An enzyme encoded by a gene containing the h10a sequence is designated Type IV (see below). The proximity (within about a million base pair region in the mouse) of the genes for Types III and IV to the PLA$_2$ Type II gene suggests a common evolutionary origin as does their localization to the same band on human chromosome 1. Further, Types II, III and IV are likely to be members of a gene family and may represent isozymes. However, a homology comparison indicates that the RPLA$_2$-8 protein is relatively distant, evolutionarily, from both Type I and Type II PLA$_2$ enzymes, but is believed to be probably closer to Type II.

In accordance with the present invention, human cDNA that contains the h10a fragment and rat cDNA that contains the rat counterpart are isolated. See FIGS. 11 and 12. The predicted protein sequences of HPLA$_2$-10 and RPLA$_2$-10 and comparisons to each other and Types I and II are shown in FIGS. 13–17. Some of the significant structural features of the proteins encoded by these cDNAs are shown in TABLE I. Importantly, the 18 amino acids that are believed to be requisite for PLA$_2$ function are conserved in both predicted proteins. See FIG. 22. This fact, plus the high degree of conservation between species, suggests that these Type IV proteins play an important role in phospholipid metabolism and processes such as membrane structuring, inflammation and intracellular signaling.

The amino acid sequences of the present invention may be produced by, for example, recombinant technology, chemical synthesis or any other methods available in the art so long as the methodology selected does not interfere with their utilities. Likewise, the nucleotide sequences of the instant invention may be produced by, for instance, PCR technology, chemical synthesis or any other methods available in the art so long as the methodology selected does not interfere with their utilities. Moreover, amino acid residues may be deleted or added or alternative amino acid residues may be substituted for those recited in the amino acid sequences of the instant invention so long as such changes do not defeat the utilities of such amino acid sequences. Still further, it should be appreciated that the present invention contemplates any amino acid sequences which are equivalent to or constitute active fragments of the amino acid sequences for the Type III and Type IV PLA$_2$ enzymes of the present invention. Of course, corresponding or other changes may be made to the nucleotide sequences of the present invention to accomplish the objectives of this invention.

It should also be appreciated that the present invention contemplates a.) any antisense nucleotide sequences which are capable of inhibiting or interfering with expression of genes and mRNA transcripts encoding Type III and Type IV PLA$_2$ enzymes of the present invention, including any amino acid sequences that are equivalent thereto or active fragments thereof, and b.) any nucleotide sequences having bases 116–720 of FIG. 3 and any equivalent fragments thereto or active fragments thereof that allow for internal initiation of mRNA cap-independent translation. Like other nucleotide sequences of the present invention, substitutions, deletions and additions may be made to the antisense nucleotide sequences and the nucleotide sequences having internal ribosome binding sites of the present invention so long as the objectives of the present invention are not defeated.

HPLA$_2$-10

In order to clone an cDNA containing the putative HPLA$_2$ exon, two primers, HClo10-1 and HClo10-1a, are generated according to the 120 bp presumptive exon II sequence. See FIG. 12. PCR amplification with these primers is used to screen human child brain, adult brain, liver, heart, and various white cell cDNA libraries. PCR amplification products are not obtained.

Since zoo blots have indicated that this putative exon is evolutionarily conserved, a rat genomic cosmid library (Clontech, Inc.) is screened using a PCR-generated copy of the HClo10-1-HClo10-1a fragement as a probe. Three unique positive clones are identified. Southern blot anaysis of the three EcoRI-digested clones using the HClo10-1-HClo10-1a fragment as a probe identifies a common 5 kb band. This band is subcloned into EcoRI-digested pUC13 and sequenced. A region (rat-10 putative exon II) in the 5 kb sequence highly homologous to h10a is identified by computer analysis.

In order to search for the presence exon I, the 5 kb human genomic DNA clone containing putative exon II is sequenced completely. Computer analysis of the sequence identified two highly homologous regions. One appears to be exon II. It contains a consensus splice acceptor site at its 5' end and a consensus splice donor site at its 3' end. The other region, located about 1.2 kb 5' of the exon II, contains a consensus splice donor site at its 3, end and a putative in-frame ATG start codon at its 5' end. It is likely to be exon I. Furthermore, when these two putative exons are joined together using the assumed splice donor and acceptor sites, the resulting sequence encodes a signal peptide and 41 amino acids which have significant homology to the amino terminus of known, mature PLA$_2$s.

After determining the putative exon I sequence, H10-A, a 5' primer located within exon I, and H10-1a, a 3' primer located within exon II, see FIG. 12, are used for RT-PCR of total human brain and lymphoblast RNA. A unique 140 bp band from both PCR reactions is sequenced. The 140 bp contains coding exons I and II, but not the putative intron I of HPLA$_2$-10. 5' and 3' RACE-RT PCR techniques, Frohman, M. A. et al.: *PNAS*, 85:8998–9002 (1988); O'Hara, O. et al.: *PNAS*, 86:6883–6887 (1989); and Loh, Y. et al.: *Science*, 243:217–220 (1989), are then used to generate the full length cDNA sequence from total human brain RNA. See FIG. 10. The entire cDNA sequence, designated HPLA$_2$-10, is shown in FIG. 12. Exon-intron junction sites are determined by genomic DNA analysis. Since the genomic DNA clone containing the first 120 bp of HPLA$_2$-10 is not obtained, it has not been determined if there are any introns in this region of the HPLA$_2$-10 genomic sequence. If no additional exons are found, HPLA$_2$-10 will apparently have an exon-intron structure typical of known Type II PLA$_2$s with a 5' untranslated exon followed by four protein coding exons.

Primers H10-A (bases 149–170) and H10-C (bases 520–548) are used to screen by PCR amplification a human stomach cDNA library (Clonetech, Inc.). A 399 bp and a 290 bp PCR amplification product are obtained only from the stomach cDNA library. The two PCR fragments are cloned into pUC19 and sequenced. The sequence of the 399 bp fragment is identical to the HPLA$_2$-10 RACE-RT PCR generated cDNA sequence from bases 148 to 541. The 290 bp fragment is identical to the 399 bp fragment except that it is missing bases 316 to 422 which encompass the 5' end of exon III. See FIG. 11. The same two PCR fragments are also amplified from total human brain and lymphocyte RNA using primers H10-A and H10-C. The 290 bp PCR product is much less abundant than the 399 bp product when amplified from human stomach and brain RNA and stomach cDNA library. Since the 290 bp product codes only for the signal peptide and the first 41 amino acids of the mature protein because of an in-frame stop codon immediately following the 41st amino acid, the in vivo significance of this product is unknown at this time.

Using the 399 bp PCR product as a probe, $6 \times 10^5$ individual plaques from the human stomach cDNA library are screened. Four positive clones are identified. The clones, designated HPLA$_2$-10-2, -3, -5, -7, have inserts of 1.4, 2.3 0.9, and 0.8 kb, respectively. The inserts of these clones are released by EcoRI digestion, subcloned into pUC19 and sequenced completely. HPLA$_2$-10-2 contains exon I-intron I-exon II of HPLA$_2$-10; HPLA$_2$-10-3 contains intron III-exon IV-intron IV of HPLA$_2$-10. The sequences of both HPLA$_2$-10-5 and HPLA$_2$-10-7 are identical to the corresponding regions of the RACE-RT-PCR generated HPLA$_2$-10 sequence except that the 5' end of the HPLA$_2$-10-5 starts at base 142 of the RACE-RT-PCR sequence and the 5' end of HPLA$_2$-10-7 starts at base 23.

To determine the transcription pattern of HPLA$_2$-10, a Human Multiple Northern Blot (Clontech, Inc.) is probed with a 399 bp fragment, i.e., HPLA$_2$-10 PCR probe, generated by PCR with primers H10-A (bases 149–170) and H10-C (bases 520–548). As seen in TABLE II, a 1.2 kb transcript is detected in heart and, less abundantly, in liver and lung RNA. In addition, a 2 kb transcript is detected in placental RNA. This suggests that the expression of HPLA$_2$-10 is not only tissue specific, but that alternative forms of the protein may be expressed in different tissues. The 2 kb transcript seen in placental RNA may result from the use of a different promoter, alternative splicing or the use of an alternative poly A site.

The HPLA$_2$-10 cDNA encodes a mature protein of about 118 amino acids with a calculated molecular mass of about 13,592 Daltons. The amino acid sequence has significant homology to known PLA$_2$s. All of the 18 invariantly conserved amino acids in known active low molecular weight PLA$_2$s, see Davidson, F. F.: *J. Mol. Evolution*, 31:228–238 (1990), are conserved in this novel protein. See FIG. 22. However, HPLA$_2$-10 contains neither the disulfide bridge between Cys 11 and 77 nor the elapid loop characteristic of Type I PLA$_2$s. HPLA$_2$-10 does, however, contain a single serine amino acid COOH-terminal extension, as shown in FIG. 22, which is more characteristic of a Type I than Type II PLA$_2$. As depicted in FIG. 22, Human Type I has a two amino acid COOH-terminal extension whereas Human Type II has a seven amino acid COOH-terminal extension. Furthermore, unlike mammalian Types I and II PLA$_2$s which have 14 cysteine residues, this putative HPLA$_2$ only has 12. The overall homology between HPLA$_2$-10 and a consensus Type I PLA$_2$ is about 30.5% while the overall homology between HPLA$_2$-10 and a consensus Type II PLA$_2$ is about 40.6%. The predicted isoelectric point (pI) of this protein is about 6.2 while that of other known Type II PLA$_2$s is about 10.5.

To test whether this HPLA$_2$-10 gene encodes an active, secreted PLA$_2$, an Epstein Barr virus-based expression vector (pCEP) is used to express the HPLA$_2$-10 cDNA in human 293s cells. pCEP contains two regions of the EBV genome required for episomal maintenance (EBNA-1 and OriP), a drug resistance gene for selection in human cells (hyg), bacterial sequences for maintenance in *E. coli*, a drug resistance gene for selection in *E. coli* (amp), and an expression cassette for the production of high levels of mRNA from an introduced sequence by using an Rous/Sarcoma virus long terminal repeat (RSV LTR) promoter and an Simian virus 40 (SV40) polyadenylation signal. HPLA$_2$-10-5', a 5' primer beginning at base 126 of HPLA$_2$-10 and containing a 10 nucleotide NheI linker at its 5' end, and HPLA$_2$-10-3', a 3' primer ending at base 555 and beginning with a 10 nucleotide XhoI linker, are used for reverse-transcriptase-polymerase chain reaction (RT-PCR) of total human brain RNA to generate the appropriate cDNA insert. The PCR product is blunt-end ligated to HincII-digested pUC19 and sequenced. The insert is then released by digestion with NheI and XhoI and is cloned into the NheI-XhoI sites of pCEP. The resulting plasmid is designated pCh10.

A known human Type II PLA$_2$ cDNA is cloned into pCEP for use as a positive control. PCR primers RASF-5' and RASF-3' are used to amplify bases 130 to 581 of pRASF, a plasmid containing the entire human known PLA$_2$ Type II cDNA. See Seilhamer, J. J.: *J. Biol. Chem.*, 264:5335–5338 (1989). The resulting plasmid is designated pRASF and is used as a control. The HPLA$_2$-2B (Type II) enzyme, as depicted in FIGS. 25 and 26, are expressed by pRASF and used as a control.

Purified plasmid DNA is transfected into human 293s cells which are selected in DMEM containing 200 µg/ml hygromycin. Medium samples from multiple cell lines transfected with either pCH10, pR8-3' or pRASF are then assayed for PLA$_2$ activity. See FIG. 21. PLA$_2$ activities derived from cell lines transfected with plasmids pCH10, pR8-3', and pRASF are accumulated in the medium. Neither 293s cells nor multiple cell lines transfected with an unrelated PLA$_2$ cDNA inactivated by a one base pair deletion at the 5' end of the mature protein show detectable PLA$_2$ activity in the medium even after 72 hours. Cell lysates that are prepared by sonication from cells stably transfected with either pCH10 or pRASF show approximately 50% of the activity of 72 hour medium samples.

Two cell lines, CpCH10-1D expressing pCH10 and CpRASF-2B expressing PRASF, are chosen for comparative study. The pH profile for the enzyme expressed by the cell lines is shown in FIG. 25. PLA$_2$ activity of HPLA$_2$-10 starts at about pH 5 and significant activity is reached at between about pH 6.5 and about pH 7.5 and remains relatively steady up to at least about pH 9.5, whereas the control Type II PLA$_2$ reaches peak activity at between about pH 7.0 and about pH 7.5 and then progressively declines.

Calcium concentration versus enzyme activity profiles for CpCH10-1D and CpRASF-2B are shown in FIG. 26. HPLA$_2$-10 appears to be a calcium-dependent PLA$_2$ having activity starting at about 0.07 mM Ca$^{2+}$ amd reaching maximal activity at between about 7 mM and about 100 mM Ca$^{2+}$. The activity of HPLA$_2$-10 then slowly decreases, but maintains significant activity, as the Ca$^{2+}$ concentration approaches about 500 mM or more. This profile differs from that of the control cell line CpRASF-2 (Type II PLA$_2$) which shows maximal activity at between about 0.5 mM and 3.0 mM Ca$^{2+}$ and becomes inactive at Ca$^{2+}$ concentrations at about 100 mM or greater. Since HPLA$_2$-10 expresses at least half of its maximal activity at Ca$^{2+}$ concentrations between 1 and 100 mM, similar to previously described Type II phospholipases, see Marshall: *Biochemical Pharmacology*, V. 44:1849–1858 (1992), it is likely that HPLA$_2$-10 is capable of functioning at concentrations found intracellularly (0.1 to 2 μM) and extracellularly (1 mM).

RPLA$_2$-8

Two PCR primers, Pla8-1 and Pla8-2 (FIG. 3), are generated using the reported rat r8 presumptive exon II sequence. See Seilhamer, J. J. et al.: *J. Cell. Biochem.*, 39:327–337 (1989). Four size-fractionated, newborn rat brain cDNA XZAPII libraries (two 0.5–1.5 kb, one 1.5–4 kb, and one greater than 4 kb, provided by Dr. L. Yu, Indiana School of Medicine, are directly amplified by PCR, See Friedman, K. D. et al.: *Nucleic Acids Research*; 16:8718 (1988), using primers pla8-1 and pla-2. Only the >4 kb insert library gives the proper size 120 bp fragment prediced by the Clo8 DNA sequence. The band is purified from an agarose gel using a QIAEX gel extraction kit (QIAGEN), cloned into m13mp18, and is sequenced using a Sequenase kit (USB). The sequence data confirms the proper identity of the PCR product. A total of 10$^6$ individual clones from the cDNA library are screened using the PCR product as a probe. Only two clones hybridize. The restriction maps of the two clones are believed to be identical. One of them, clo8–2, is sequenced completely. The sequence, designated RPLA$_2$-8, is shown in FIG. 3.

RPLA$_2$-8 is a 4.4 kb cDNA, which is about five-times larger than any known mammalian 14 kDa PLA$_2$ cDNA. See Seilhamer, J. J. et al.: *DNA*, 5:519–527 (1986); Seilhamer, J. J. et al.: *J. Biol. Chem.*, 264:5335–5338 (1989); Ohara, O. et al.: *Proc. Natl. Acad. Sciences U.S.A.*, 86:6883–6887 (1989); Kramer, R. M. et al.: *J. Biol. Chem.*, 264:5768–5775 (1989); and Komada, M. et al.: *J. Biochem.*, 106:545–547 (1989). The 480 bp coding region is believed to be contained in a putative 1.2 kb loop flanked by 121 bp perfect inverted repeats. See FIG. 2. This stem-loop is flanked by perfect 121 bp inverted repeats. This stem-loop structure leaves about 3 kb of 3' "tail." See FIGS. 1 and 2. Translation of RNAs containing such a secondary structure cannot readily be explained by the conventional translation scanning model. See Pain, V. M.: *Biochemistry J.*, 235:625–637 (1986). Nevertheless, it is believed that there is an internal ribosome binding site between the 5' repeat sequence and ATG translation start site. Cloning the sequence between base 116 and 720, see FIG. 3, in both normal and reverse orientations in front of an internal luciferase gene which lies downstream of a CAT gene, see Macejjak, D. G. et al.: *Nature*, 353:90–94 (1991), see FIG. 20, followed by detecting luciferase gene expression in transfected Hela cells (with positive and negative control constructs), confirms that the fragment does contain a internal ribosome binding sequence. Luciferase expression is significantly higher when the fragment is cloned in normal orientation then in reverse orientation. It is believed that the translation of mRNAs initiated by an internal ribosome binding mechanism may play an important role in mitosis, meiosis or specific viral infection, because cap-dependent translation during mitosis in mammalian cells is unlikely, due to the presence of underphosphorylated and therefore nonfunctional translation initiation factor, eif-4F. See Macejjak, D. G. et al.: *Nature*, 353:90–94 (1991). It is therefore believed that the RPLA$_2$-8 gene product could play a role during these processes.

As a preliminary study, the pattern of RPLA$_2$-8 gene expression, see TABLE III, is examined 5 by screening rat tissues with reverse transcription followed by PCR (RT-PCR), using primers pla8-1 and pla8-2. See FIG. 3.

TABLE III

Reverse Transcription-PCR (RT-PCR) of Total RNA of Different Rat tissues by Primers Clo8-1 and Clo8-1a

| | |
|---|---|
| 1. Brain | + |
| 2. Cerebellum, Brain Stem | + |
| 3. Kidney | + |
| 4. Lung | + |
| 5. Heart | + |
| 6. Muscle (?) | + |
| 7. Pancreas | − |
| 8. Small intestine | − |
| 9. Liver | − |
| 10. Prostate | − |
| 11. Bladder | − |
| 12. Spleen | − |
| 13. Adrenal | − |
| 14. Submaxillary | − |

In addition, to determine transcription patterns of RPLA$_2$-8 and RPLA$_2$-10, a Rat Multiple Northern Blot (Clontech, Inc.) is probed with a 489 bp fragment, i.e., RPLA$_2$-8 PCR probe, generated by PCR with primers RClo8-5' (bases 716–742) and Rclo8-3' (bases 1178–1205). A rat Multiple Northern Blot (Clontech, Inc.) is also probed with a 427 bp fragment, i.e., RPLA$_2$-10 PCR probe, and amplified using primers Rclo10-5' (bases 226–253) and Rclo10-3' (bases 627–653). As seen in TABLE II, an RPLA$_2$-8 mRNA is detected in testis only and an RPLA$_2$-10 mRNA is detected in heart and perhaps lung only.

Figure 4:
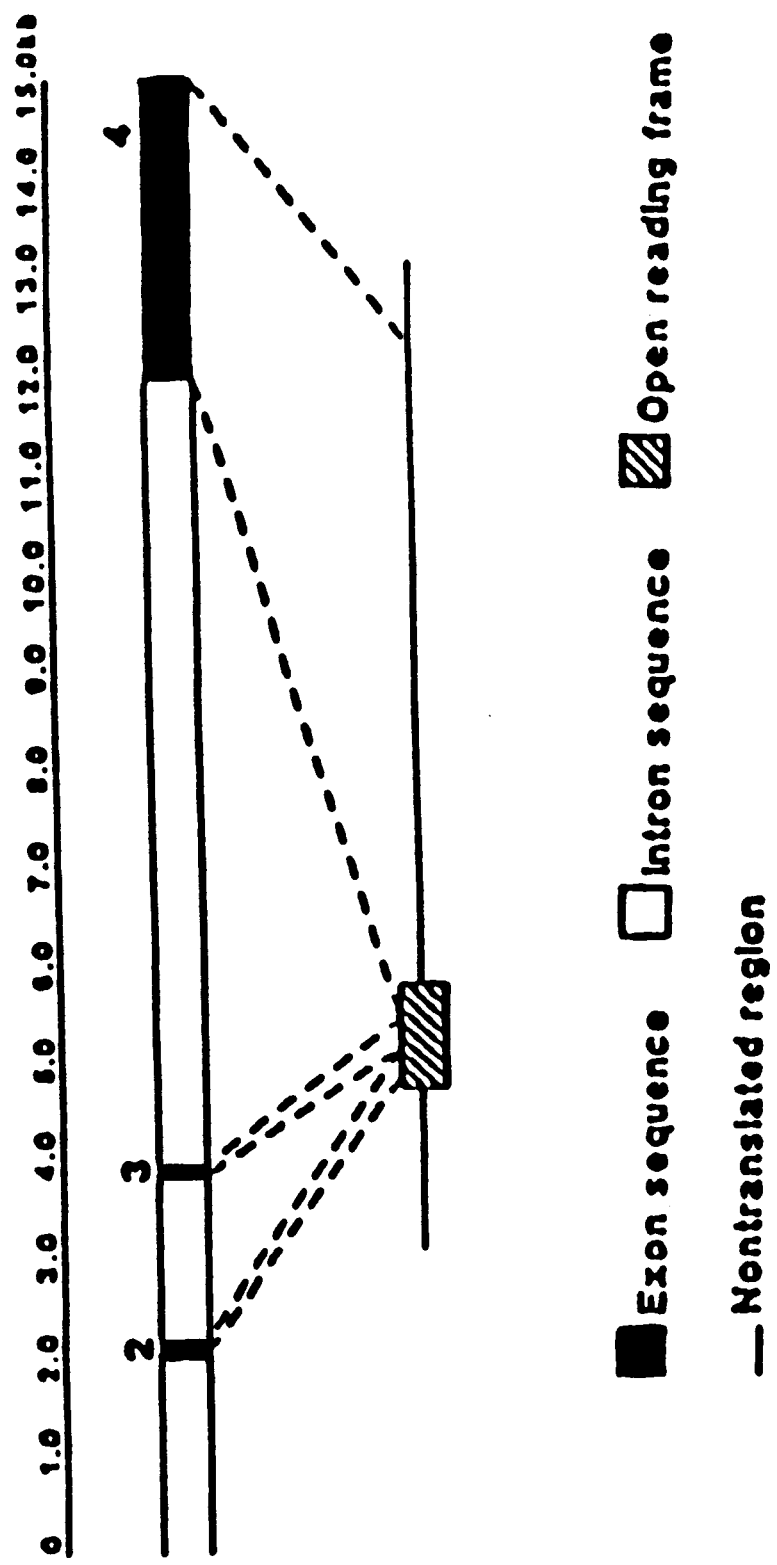
FIG. 4 depicts a diagram of the genomic DNA region containing exons 2, 3 and 4 of RPLA$_2$-8 in comparison to the corresponding cDNA.

In order to determine the exon-intron junction sites and confirm the 121 bp direct repeat sequence in the genomic DNA, a 15 kb rat genomic DNA clone containing RPLA$_2$-8 coding exon II is analyzed by Southern blot, and partial sequencing. The 15 kb genomic DNA structure is shown in FIG. 4. It does not contain exon I and the 5' 121 bp repeat, but it does contain the 3' 121 bp repeat. To further investigate the 5' rat genomic DNA sequence, a cosmid genomic DNA library (Clontech, Inc.) is screened using a PCR-generated fragment containing RPLA$_2$-8 exon I-intron I-exon II. Twelve positive clones are indentified. Restriction mapping indicates that all clones (about 40 kb each) are identical. Unfortunately, the cosmid clones could not contain the 5' 121 bp repeat because their 5' ends are located in intron I. Thus, RT-PCR is used to confirm the presence of the 5' 121 bp direct repeat sequence. Pla8-7, a 22 bp 5' primer starting at base 73, which lies within the 121 bp repeat sequence and pla8-8, a 22 bp 3' primer ending at base 212, see FIG. 3, are generated to conduct RT-PCR of rat brain total RNA. The resulting RT-PCR fragment is purified from the agrose gel and cloned into m13mp18, and the sequence is confirmed to be as predicted by the cDNA.

To test whether this PLA$_2$-8 gene encodes an active, secreted PLA$_2$, an Epstein Barr virus-based expression vector (pCEP) is used to express the RPLA$_2$-8 cDNA in human 293s cells. pCEP contains two regions of the EBV genome required for episomal maintenance (EBNA-1 and OriP), a drug resistance gene for selection in human cells (hyg), bacterial sequences for maintenance in E. coli, a drug resistance gene for selection in E. coli (amp), and an expression cassette for the production of high levels of mRNA from an introduced sequence by using an Rous/Sarcoma virus long terminal repeat (RSV LTR) promoter and an Simian virus 40 (SV40) polyadenylation signal. pR8-3', a chimeric construct, is constructed as follows. RASF-5', a 5' primer beginning with a 10 nucleotide NheI linker followed by 22 nucleotides starting at base 130, and Ju9, a 22 nucleotide 3' primer complementary to base 177 and 198, see Seilhamer, J. et al.: *J. Biol. Chem.*, 264:5335–5338 (1989), are used to PCR amplify plasmid pRASF from bases 130 to 198. pRASF contains the entire known $PLA_2$ Type II cDNA. See Seilhamer, J. et al.: *J. Biol. Chem.*, 264:5335–5338 (1989). The PCR product is purified and is digested with NheI plus NcoI. JuR8–11, a 5' primer with a total length of 31 nucleotides, beginning with GCCATGGGA followed by base 806 to 827 of $RPLA_2$-8 sequence, see FIG. 3, and R8-3', a 3' primer starting with a 10 nucleotide NheI linker at its 5' end, followed by 22 nucleotides complementary to $RPLA_2$-8 base 1178 to 1200, see FIG. 3, are used to PCR amplify plasmid $RPLA_2$-8. The PCR product is purified and digested with XhoI plus NcoI. Both digested PCR products are then ligated together into XhoI-NheI digested pCEP. Sequencing is carried out to confirm the nucleotide sequence of pR8-3'. CpR8-3' is a single clone of cells chosen to represent the typical pH optimum and $Ca^{++}$ dependence of CpR8 transfected 293s cells. The effects of pH and calcium concentration on enzyme activity are illustrated in FIGS. 23 and 24, respectively, for the $RPLA_2$-8 enzyme (Type III) and are similar, but different to the pH and calcium profiles for the $HPLA_2$-10 enzyme (Type IV) encoded for by the $HPLA_2$-10 cDNA cloned into plasmid cPH10, as shown in FIGS. 25 and 26, respectively. In other words, $RPLA_2$-8 also appears to be a pH and calcium-dependent $PLA_2$ enzyme having activity starting at about pH 5.5 and having significant activity at between about pH 7 and about pH 9 and having activity starting at about 0.1 mM $Ca^{2+}$ and having significant activity at between about 0.3 mM and about 2 mM $Ca^{2+}$, respectively. The activity of $RPLA_2$-8, however, apparently progressively declines at a pH of greater than about 9 and at a calcium concentration of greater than about 2 mM. Nonetheless, FIGS. 23–26 illustrate phsopholipase activity for the Type III and Type IV phospholipase enzymes of the present invention. Moreover, FIGS. 23–26 show that the pH and calcium profiles for the Type III and Type IV phospholipase enzymes of the present invention are different from the pH and calcium profiles for phospholipases known heretofore.

It should be appreciated by those skilled in the art that the novel $PLA_2$ Type III and Type IV enzymes described in the instant application may have many different potential uses.

Although both "Type II" soluble $PLA_2$ and intracellular membrane-associated $PLA_2$ have been shown to mediate many aspects of the inflammatory cascade, it may well be that the new $PLA_2$ enzymes may also play a role, either by directly functioning to liberate arachidonic acid and 2-lysophospholipid, or by replacing the functions of the former in tissues and/or individuals in which the enzymes may be otherwise missing. As such, inhibition of these new enzymes by standard strategies known in the art (e.g., crystallography-based rational drug design; antisense; triple helix; monoclonal antibodies) could be valuable in anti-inflammatory therapy.

Phospholipases $A_2$ are involved in other processes vital to sustaining life in humans, including but not limited to pulmonary surfactant turnover, biomembrane maintenance and metabolism, various lipid catabolic pathways, platelet activation factor metabolism, and sperm-mediated egg activation. First, it is possible that certain diseases present today involve alterations in these functions, and could be treated therapeutically with exogenously added recombinant $PLA_2$ or anti-$PLA_2$. Second, as new $PLA_2$-inhibiting anti-inflammatory therapeutics are developed, many may exhibit cross-inhibition with these other new enzymes, thereby causing undesired side-effects. Both knowledge of the sequence/structure of these new enzymes, and the ability to restore their function through addition of the appropriate recombinant enzyme could be of value in reducing such side-effects.

Although these enzymes have been characterized as $PLA_2$ enzymes, they may well have other vital enzymatic activities. For example, LCAT (lecithin-cholesterol acyl transferase) also exhibits $PLA_2$ activity. Alternatively, these enzymes may function as phospholipases Al, phospholipases B, phospholipases C, lysophopholipases, acyl hydrolases, ribonucleases, lipases, or phosphodiesterases, all of which are esterases which resemble phospholipase $A_2$ in chemical activity. If this is the case, these new enzymes could be used to treat defects in a variety of metabolic pathways.

$PLA_2$ is also useful in the food processing industry. See Dutilh et al.: *J. Sci. Food Agricul.*, 32:451–458 (1981), and in the preservation of fish, see Mazeaud et al.: *J. Fish Res. Board Cun.*, 33:1297–1303 (1976). Recombinant forms of the instant new $PLA_2$s may be useful to replace natural sources of these enzymes.

$RPLA_2$-8, by virtue of its specific synthesis in rat testis, may play a key role in activation during fertilization by sperm. Therefore, antagonism of its function may prove useful as a specific anti-fertility reagent in pests such as rodents.

$HPLA_2 10$ and $RPLA_2$-10, by virtue of their specific synthesis in cardiac tissue, may play a key role in cardiac lipid metabolism specific to cardiac tissue, and may indicate a specialized new function for this enzyme. A major component of heart tissue is cardiolipin, and Type IV phospholipase may mediate metabolism of this related diphospholipid in this organ. Therefore, recombinant forms of the new $PLA_2$s could prove useful in the treatment of disorders involving cardiac phospholipid metabolism.

In addition, the new $PLA_2$s have been mapped into a genetic locus known to be associated with Batten's disease (or Neuronal Ceroid Lipfuscinosis; NCL). Since the latter disorder has been shown to involve alterations in activity of certain phospholipases, see Dawson et al.: *Advances in Experimental Medicine & Biology*, 266:259–270 (1989), these new enzymes may be useful as a therapeutic to treat the former, and as a diagnostic to detect the presence of these genetic abnormalities so that proper counseling and early treatment of the disease would be possible.

Examples of various embodiments of the present invention will now be further illustrated with reference to the following Examples.

EXAMPLE I

CpCH10-1D Cell Line Transfected with pCH10 which Expresses $HPLA_2$-10

Figure 10:
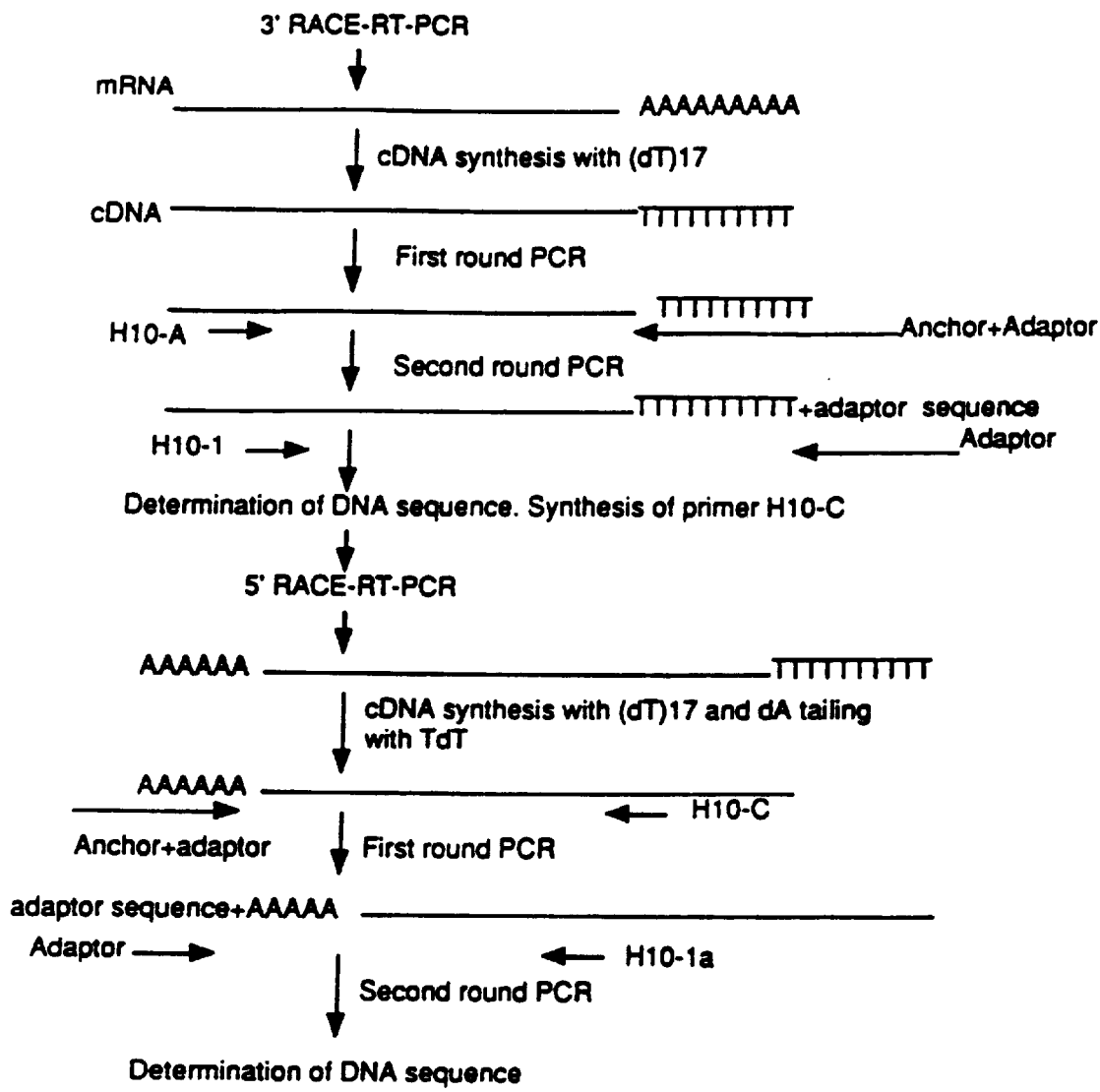
FIG. 10 depicts a flow diagram of 3' and 5' RACE-RT PCR techniques used to obtain a full length HPLA$_2$-10 sequence cDNA from brain mRNA.

Total RNA is prepared according to the method of Chomcyzmski and Sacchi: *Analytical Biochemistry*, 162:156–159 (1987). 5' and 3' RACE-RT PCR techniques are used to generate the full length cDNA from total human brain RNA as described by Ishisaki: *Biochem. Biophysic. res. Comm.*, 162:1030–1036 (1989), and outlined in FIG. 10. PCR amplifications are done using 30 cycles at 95° C. for 20 seconds, 60° C. for 20 seconds and 72° C. for 75 seconds in 100 µl of buffer containing a final concentration of 1.5 mM $MgCl_2$, 200 µM dNTP, 100 mM Tris-$HCl_1$, pH 8.3, and 3 units Taq polymerase. Anchor (300 ng) and adaptor (50 ng) primers are used in both 5' and 3' RACE-RT PCR. Primers H10-C (300 µg) and H10-1a (300 µg) are used for 5' RACE-RT PCR. Primers H10-A (300 µg) and H10-1 (300 µg), see FIG. 10, are used for 3' RACE-RT PCR. Primer sequences are listed in TABLE IV.

TABLE IV

| Primers | Sequences |
| --- | --- |
| H10-A | CTGGCTTGGTTCCTGGCTTGTA[13] |
| H10-1 | GCAAGGAGGCTTGCTGGACCTA[14] |
| H10-1a | ATCGGTGCCATCCTTGGGGGTT[15] |
| H10-C | GCAGAGGATGTTGGGAAAGTAT[16] |
| H10-5' | GAATTCGCTAGCCAGAGATGAAAGGCCTCCTCCCACTGGCTTGG[17] |
| H10-3' | CTCGCTCTCGAGGCCCTAGGAGCAGAGGATGTTGGGAAA [18] |
| Anchor | GGCCACGCGTCGACTAGTAC(T)$_{17}$[19] |
| Adaptor | GGCCACGCGTCGACTAGTAC[20] |

13=SEQ ID No. 13;
14=SEQ ID No. 14;
15=SEQ ID No: 15;
16=SEQ ID No. 16
17=SEQ ID No. 17;
18=SEQ ID No. 18;
19=SEQ ID No. 19;
20=SEQ ID No. 20

$6 \times 10^5$ clones from a human stomach cDNA phage library (Clontech, Inc.) and $5 \times 10^5$ clones from a rat genomic DNA cosmid library (Clontech, Inc.) are screened according to the procedures provided by Clontech Inc.

A Human Multiple Northern Blot (Clontech, Inc.) is hybridized according to the manufacturer's directions.

293s cells (ATCC CRL 1573) are grown in Dulbecco's modified Eagle's medium (DMEM) supplemented with 10% fetal bovine serum. Approximately $7.5 \times 10^5$ cells are transfected with 10 µg of purified supercoiled plasmid DNA from either pCH10 or PRASF to create cell lines of the type CpCH10-1D and CpRASF-2B, respectively, according to the methods of Kingston, R. E.: Calcium Phosphate Transfection in Current Protocols in Molecular Biology. ed. Frederick M. Ausubel et al., pp. 9.1.1–9.1.3 (1989). Twenty-four hours after transfection, 200 units per ml of hygromycin is added to the medium. Stably-transfected, hygromycin-resistant colonies are selected ten days after transfection and are maintained in DMEM containing 200 units per ml of hygromycin. To test for $PLA_2$ activity, $2.0 \times 10^6$ cells are plated in a 25 $cm^2$ flask and medium is collected 24, 48 and 72 hours after plating.

Autoclaved [1-$^{14}$C] oleic acid-labeled *Escherichia coli* (*E. coli*) JM109 is prepared according to the methods described by Elsbach, P. et al.: *Methods in Enzymoloqy*, 97:24–31 (1991) for use as a $PLA_2$ substrate. Briefly, 20 µl medium is incubated for 15 minutes at 37° C. with *E. coli* substrate (a mix of $2.5 \times 10^8$ labeled and unlabeled bacteria to provide 10,000 cpm) in a total volume of 250 µl (40 mM Tris/HCl, pH 7.8, 150 mM NaCl, 10 mM $Ca^{2+}$). The reaction is stopped by the addition of 250 µl ice cold 0.5% (W/V) fatty acid-poor BSA (USB). After incubation on ice for 5 minutes, the samples are centrifuged at 10,000×g for 3 minutes and 250 µl of the supernatant containing released (1-$^{14}$C]oleic acid is counted in a scintillation counter.

The pH optimum for human Type IV $PLA_2$ enzyme activity is determined using 20 µl of medium diluted to produce approximately 10% substrate hydrolysis. Sodium acetate buffer (final concentration 25 mM) is used for the pH range 4–6.5 and Tris/HCl buffer (final concentration 25 mM) for the pH range 7–9. See FIG. 25.

The calcium dependence of the human Type IV enzyme activity is examined in the calcium concentration range 0–400 mM. The buffer solution (Tris/HCl, pH 7.5, final concentration 25 mM) is prepared with doubly distilled, deionized water which contained a minimal amount of metal ions. EDTA (300 mcM) is added to the assay mixture in order to chelate the residual calcium. 20 µl of medium is diluted to produce 10% substrate hydrolysis. See FIG. 26.

EXAMPLE II

CpR8-3' Cell Line Transfected With pCR8 Which Epxresses $RPLA_2$-8

293s cells (ATCC CRL 1573) are grown in Dulbecco's modified Eagle's medium (DMEM) supplemented with 10% fetal bovine serum. Approximately $7.5 \times 10^5$ cells are transfected with 10 µg of purified supercoiled plasmid DNA from pR8-3' to create a cell line of the type CpR8-3' according to the methods of Kingston, R. E.: Calcium Phosphate Transfection in Current Protocols in Molecular Biology. ed. Frederick M. Ausubel et al., pp. 9.1.1–9.1.3 (1989). Twenty-four hours after transfection, 200 units per ml of hygromycin is added to the medium. Stably-transfected, hygromycin-resistant colonies are selected ten days after transfection and are maintained in DMEM containing 200 units per ml of hygromycin. To test for $PLA_2$ activity, $2.0 \times 10^6$ cells are plated in a 25 $cm^2$ flask and medium is collected 24, 48 and 72 hours after plating.

Autoclaved [1-$^{14}$C] oleic acid-labeled *Escherichia coli* (*E. coli*) JM109 is prepared according to the methods described by Elsbach, P. et al.: *Methods in Enzymology*, 97:24–31 (1991) for use as a PLA$_2$ substrate. Briefly, 20 μl medium is incubated for 15 minutes at 37° C. with *E. coli* substrate (a mix of 2.5×10$^8$ labeled and unlabeled bacteria to provide 10,000 cpm) in a total volume of 250 μl (40 mM Tris/HCl, pH 7.8, 150 mM NaCl, 10 mM Ca$^{2+}$). The reaction is stopped by the addition of 250 μl ice cold 0.5% (W/V) fatty acid-poor BSA (USB). After incubation on ice for 5 minutes, the samples are centrifuged at 10,000×g for 3 minutes and 250 μl of the supernatant containing released (1-$^{14}$C]oleic acid is counted in a scintillation counter.

The pH optimum for human Type III PLA$_2$ enzyme activity is determined using 20 μl of medium diluted to produce approximately 10% substrate hydrolysis. Sodium acetate buffer (final concentration 25 mM) is used for the pH range 4–6.5 and Tris/HCl buffer (final concentration 25 mM) for the pH range 7–9. See FIG. 23.

The calcium dependence of the human Type III enzyme activity is examined in the calcium concentration range 0–400 mM. The buffer solution (Tris/HCl, pH 7.5, final concentration 25 mM) is prepared with doubly distilled, deionized water which contained a minimal amount of metal ions. EDTA (300 mcM) is added to the assay mixture in order to chelate the residual calcium. 20 μl of medium is diluted to produce 10% substrate hydrolysis. See FIG. 24.

EXAMPLE III

PLA$_2$ Activity 7.5×10$^5$ 293s cells are transfected with 10 μg of super-coiled plasmid DNA according to the method of Kingston, R. E.: Calcium Phosphate Transfection in Current Protocols in Molecular Biology. ed. Frederick M. Ausubel et al., pp. 9.1.1–9.1.3 (1989). Hygromycin-resistant colonies are selected 10 days after transfection and are maintained in DMEM containing 200 units of hygromycin. CpCH10-1B, CpCH10-1C, CpCH10-1D and CpCH10-2G are independent, hygromycin-resistant cell lines transfected with pCH10, a plasmid containing the human Type IV PLA$_2$ cDNA; CpRASF-2B is a hygromycin-resistant cell line transfected with pMCH6, a plasmid containing the known Type II PLA$_2$ gene. CpR8-3' is a hygromycin-resistant cell line transfected with pR8-3', a plasmid containing the rat Type III PLA$_2$ cDNA. These cell lines are tested two months after their stable transfection. Each has been maintained and subcloned in hygromycin-containing medium. For this experiment, exponentially growing cells are plated at 4×10$^5$ cells per ml. Medium samples are taken 24, 48 and 72 hours after plating. 20 μl of each medium sample is assayed under standard conditions, see Elsbach, P. et al.: *Methods in Enzymology*, 197:24–31 (1991) for PLA$_2$ activity. Activity is expressed as a fraction of autoclaved [1-$^{14}$C]oleic acid labeled *E. coli* Y1090 incubated alone. See FIG. 21.

EXAMPLE IV

Searching for Human cDNA and Genomic DNA Secquences homologous to RPLA$_2$-8

Two primers, clo8-4 and clo8-5, synthesized according the published human h8 presumptive exon II sequence, Seilhamer, J. J.: *J. of Cellular Biochemistry*, 39:327–329 (1989), are used in a PCR amplification screen of human child brain, adult brain, liver, heart, and various white cell cDNA libraries. No PCR amplification is obtained from any of them. Two overlapping human genomic DNA clones, clone 8 and walk 9, containing 10 kb of DNA 5' of h8 exon II and 16 kb of DNA 3' of h8 exon II, respectively, are then analyzed. Southern blot analysis using the PCR fragment containing the RPLA$_2$-8 open reading frame DNA sequence as a probe identified two EcoRI fragments, one in clone 8 and one in walk 9. These two fragments are subcloned into pUC19 and sequenced. DNA sequence homology between these sequences and the RPLA$_2$-8 cDNA indicated that one fragment contains a region homologous to RPLA$_2$-8 exons I and II, and that the other fragment contains a region homologous to RPLA$_2$-8 exon IV. See FIG. 16. In order to search for exon III of a human RPLA$_2$-8 homologue, the entire region between exon II and exon IV is sequenced. No region homologous to RPLA$_2$-8 coding exon III is found by computer analysis of this sequence. To determine if the HPLA$_2$-8 sequence is transcribed, two primers, one in coding exon II and one in exon IV, are used to do RT-PCR of human brain and lymphoblast total RNA. No PCR amplification signal is obtained.

EXAMPLE V

Phospholipase A$_2$ Assay using Auto-claved Labeled Bacterium as a Substrate Autoclaved [1-$^{14}$C]oleic acid-labeled *E.coli* 1-$^{14}$C 109 is prepared according to the methods described by Elsbach: P. et al.: *Methods in Enzymology*, 197:24–31 (1991) for use as the PLA$_2$ substrate. Commercial porcine pancreatic PLA$_2$ (Sigma) is used for the standard assay. Simply, the serialy diluted PLA$_2$ solutions are incubated for 15 minutes at 37° C. with *E.coli* substrate (a mix of 2.5×10$^8$ labeled and unlabled bacteria to provide 10,000 cpm) in a total volume of 250 ul (40mM Tris/HCl, pH 7.8, 10 mM Ca$^{+2}$). The reaction is stopped by the addition of 250 ul ice cold 0.5% (W/V) fatty acid-poor BSA (USB). After incubatation on ice for 5 minutes, the samples are centrifuged at 10,000×g for 2 minutes, and 250 μl of the supernatant containing released [$^{1-14}$C]oleic acid is counted in a scintillation counter.

The present invention may, of course, be carried out in other specific ways than those herein set forth without departing from the spirit and essential characteristics of the invention. The present embodiments are, therefore, to be considered in all respects as illustrative and not restrictive and all changes coming within the meaning and equivalency range of the appended claims are intended to be embraced herein.

Having described our inventions, we claim:

1. A substantially pure Type IV PLA$_2$ enzyme, said Type IV PLA$_2$ enzyme having the following characteristics:
  i) lacking cysteines at amino acids position 11 and 77
  ii) lacking an elapid loop,
  iii) having only 12 cysteine amino acid residues in its mature sequence,
  iv) having an isoleucine at position 9, a tyrosine-glycine at positions 25-26, a cysteine-glycine at positions 29-30, a glycine at position 32, an aspartate at position 42, a cysteine-cysteine at positions 44-45, a histidine-asparate at positions 48-49, a cysteine-tyrosine at positions 51-52, a tyrosine at position 73, a cysteine at position at positions 84, 99 and 108, and a tyrosine at position 116, and
  v) lacking an alanine-alanine at positions 105-106, the positions being numbered as in FIG. 22.

2. The Type IV PLA$_2$ enzyme of claim 1, said Type IV PLA$_2$ enzyme having a molecular weight of about 14 KD.

3. The Type IV PLA$_2$ enzyme of claim 1, said Type IV PLA$_2$ enzyme having an amino acid sequence set forth in SEQ ID NO: 44.

4. The Type IV PLA$_2$ enzyme of claim 1, said Type IV PLA$_2$ enzyme having an amino acid sequence set forth in SEQ ID NO: 40.

5. The Type IV PLA$_2$ enzyme of claim 1, said Type IV PLA$_2$ enzyme having an amino acid sequence which includes SEQ ID NO: 9.

6. The Type IV PLA$_2$ enzyme of claim 1, said Type IV PLA$_2$ enzyme having an amino acid sequence which includes SEQ ID NO: 11.

7. The Type IV PLA$_2$ enzyme of claim 1, said Type IV PLA$_2$ enzyme having the following features:

a) a leucine residue at position 5;
  b) a methionine residue at position 8; and
  c) having leucine-valine at positions 105 and 106, the positions being numbered as in FIG. 22.

8. The Type IV PLA$_2$ enzyme of claim 1, said Type IV PLA$_2$ enzyme having a YGCYCG Ca$^{2+}$ binding loop corresponding to amino acids 24 to 29 of SEQ ID NO: 44.

9. The Type IV PLA$_2$ enzyme of claim 1, said Type IV PLA$_2$ enzyme further including a COOH-terminal amino acid extension.

10. The Type IV PLA$_2$ enzyme of claim 9, said Type IV PLA$_2$ enzyme having an about one amino acid COOH-terminal extension.

11. The Type IV PLA$_2$ enzyme of claim 10, said about one amino acid COOH-terminal extension being a serine and said Type IV PLA$_2$ enzyme being a human Type IV PLA$_2$ enzyme.

12. The Type IV PLA$_2$ enzyme of claim 1, said Type IV PLA$_2$ enzyme having phospholipase activity which is significant at a pH of between about 6.5 and about 7.5 and at a calcium concentration of between about 7 mM and about 100 mM.

13. The Type IV PLA$_2$ enzyme of claim 12, said phospholipase activity progressively declining at a calcium concentration of greater than about 100 mM.

14. The Type IV PLA$_2$ enzyme of claim 1, said Type IV PLA$_2$ enzyme being a rat Type IV PLA$_2$ enzyme.

15. The Type IV PLA$_2$ enzyme of claim 7, said Type IV PLA$_2$ enzyme having phospholipase activity which is about maximal at a pH of between about 6.5 and about 7.5 and at a calcium concentration of between about 7 mM and about 100 mM.

16. The Type IV PLA$_2$ of claim 7, having a lysine at position 6 and a glutamine at position 71, the positions being numbered as in FIG. 22.

17. The Type IV PLA$_2$ of claim 16, having a glutamate at position 10 and an arginine at position 111, the positions being numbered as in FIG. 22.

18. The Type IV PLA$_2$ of claim 17, having a lysine at position 38 and an arginine at position 69, the positions being numbered as in FIG. 22.

19. The Type IV PLA$_2$ of claim 18, having a tyrosine-arginine at positions 75–76, the positions being numbered as in FIG. 22.

20. The Type IV PLA$_2$ of claim 19, having a tyrosine-glutamine-tyrosine at positions 121–123, the positions being numbered as in FIG. 22.

21. The Type IV PLA$_2$ of claim 20, having an aspartate-arginine-lysine at positions 102–104, the positions being numbered as in FIG. 22.

22. The Type IV PLA$_2$ of claim 21, having a glutamate-glutamate-lysine at positions 56–58, the positions being numbered as in FIG. 22.

23. The Type IV PLA$_2$ of claim 22, having a lysine-valine-threonine-glycine-lysine at positions 12–16, the positions being numbered as in FIG. 22.

24. The Type IV PLA$_2$ of claim 23, having a phenylalanine at positions 24, 77 and 93, and a proline at positions 37 and 125, the positions being numbered as in FIG. 22.

25. The Type IV PLA$_2$ of claim 24, having an asparagine at positions 17, 21, 112, 117 and 126 and a tryptophan at positions 31 and 43, the positions being numbered as in FIG. 22.

26. A substantially pure Type III PLA$_2$ enzyme, said Type III PLA$_2$ enzyme having the following characteristics:
    i) lacking cysteines at amino acids position 11 and 77
    ii) lacking an elapid loop,
    iii) having only 16 cysteine amino acid residues in its mature sequence,
    iv) having a valine at position 9, a tyrosine-glycine at positions 25–26, a cysteine-glycine at positions 29–30, a glycine at position 32, an aspartate at position 42, a cysteine-cysteine at positions 44–45, a histidine-aspartate at positions 48–49, a cysteine-tyrosine at positions 51–52, a tyrosine at position 73, a cysteine at position at positions 84, 99 and 108, and a tyrosine at position 116, and
    v) lacking the alanine-alanine at positions 105–106, the positions being numbered as in FIG. 22.

27. The Type III PLA$_2$ enzyme of claim 26, said Type III PLA$_2$ enzyme having a molecular weight of about 14 KD.

28. The Type III PLA$_2$ enzyme of claim 26, said Type III PLA$_2$ enzyme having an amino acid sequence set forth in SEQ ID NO: 43.

29. The Type III PLA$_2$ enzyme of claim 26, said Type III PLA$_2$ enzyme having an amino acid sequence encoded for by the nucleotide sequence of SEQ ID NO: 33.

30. The Type III PLA$_2$ enzyme of claim 26, said Type III PLA$_2$ enzyme having an amino acid sequence which includes a prepeptide amino acid sequence of SEQ ID NO: 6.

31. The Type III PLA$_2$ enzyme of claim 26, said Type III PLA$_2$ enzyme having the following features:
    a) a methionine residue at position 8
    b) a phenylalanin residue at position 5; and
    c) having a serine-valine at positions 105 and 106,
       the positions being numbered as in FIG. 22.

32. The Type III PLA$_2$ enzyme of claim 26, said Type III PLA$_2$ enzyme having a YGCYCG Ca$^{2+}$ binding loop corresponding to amino acids 24 to 29 of SEQ ID NO: 44.

33. The Type III PLA$_2$ enzyme of claim 26, said Type III PLA$_2$ enzyme having an about seven amino acids COOH-terminal extension.

34. The type III PLA$_2$ enzyme of claim 33, said about seven amino acids COOH-terminal extension having the amino acid sequence GRDKLHC corresponding to amino acids 124 to 130 of SEQ ID NO: 43, said Type III PLA$_2$ enzyme being a rat Type III PLA$_2$ enzyme.

35. The Type III PLA$_2$ enzyme of claim 26, said Type III PLA$_2$ enzyme being a human Type III PLA$_2$ enzyme.

36. The Type III PLA$_2$ enzyme of claim 26, said Type III PLA$_2$ enzyme having phospholipase activity which is significant at a pH of between about 7 and about 9 and at a calcium concentration of between about 0.3 mM and about 2 mM.

37. The Type III PLA$_2$ enzyme of claim 36, said phospholipase activity progressively declining at a pH which is greater than about 9 and at a calcium concentration which is greater than about 2 mM.

38. The Type III PLA$_2$ enzyme of claim 31, said Type III PLA$_2$ enzyme having phospholipase activity which is about maximal at a pH of between about 7 and about 9 and at a calcium concentration of between about 0.3 mM and about 2 mM.

* * * * *

UNITED STATES PATENT AND TRADEMARK OFFICE
CERTIFICATE OF CORRECTION

PATENT NO: 5,972,677

DATED: October 26, 1999

INVENTOR(S): Tischfield et al.

It is certified that errors appear in the above-identified patent and that said Letters Patent are hereby corrected as shown below:

Col. 69, claim 26, line 36, please delete "only".

Signed and Sealed this

Third Day of April, 2001

Attest:

NICHOLAS P. GODICI

*Attesting Officer*  *Acting Director of the United States Patent and Trademark Office*

SEQUENCE LISTING (1) GENERAL INFORMATION:

(iii) NUMBER OF SEQUENCES: 44

(2) INFORMATION FOR SEQ ID NO:1:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:1:

Met Lys Leu Leu Val Leu Ala Val Leu Leu Thr Val Ala Ala Ala
1               5                   10                  15

(2) INFORMATION FOR SEQ ID NO:2:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

Asp Ser Gly Ile Ser Pro Arg
1               5

(2) INFORMATION FOR SEQ ID NO:3:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Ala Val Trp Gln Phe
1               5

(2) INFORMATION FOR SEQ ID NO:4:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Met Lys Thr Leu Leu Leu Ala Val Ile Met Ile Phe Gly Leu Leu Gln
1               5                   10                  15

Ala His Gly (2) INFORMATION FOR SEQ ID NO:5:

(i) SEQUENCE CHARACTERISTICS:
        (A) LENGTH: 5 amino acids
        (B) TYPE: amino acid
        (C) STRANDEDNESS: single (D) TOPOLOGY: linear (ii) MOLECULE TYPE: protein (xi) SEQUENCE DESCRIPTION: SEQ ID NO:5:

Asn Leu Val Asn Phe
1               5

(2) INFORMATION FOR SEQ ID NO:6:

(i) SEQUENCE CHARACTERISTICS:
              (A) LENGTH: 21 amino acids
              (B) TYPE: amino acid
              (C) STRANDEDNESS: single
              (D) TOPOLOGY: linear (ii) MOLECULE TYPE: protein (xi) SEQUENCE DESCRIPTION: SEQ ID NO:6:

Met Asp Leu Leu Val Ser Ser Gly Met Lys Gly Ile Ala Val Phe Leu
1               5                   10                  15

Val Phe Ile Phe Cys
            20

(2) INFORMATION FOR SEQ ID NO:7:

(i) SEQUENCE CHARACTERISTICS:
              (A) LENGTH: 7 amino acids
              (B) TYPE: amino acid
              (C) STRANDEDNESS: single
              (D) TOPOLOGY: linear (ii) MOLECULE TYPE: protein (xi) SEQUENCE DESCRIPTION: SEQ ID NO:7:

Trp Thr Thr Ser Thr Leu Ser
1               5

(2) INFORMATION FOR SEQ ID NO:8:

(i) SEQUENCE CHARACTERISTICS:
              (A) LENGTH: 5 amino acids
              (B) TYPE: amino acid
              (C) STRANDEDNESS: single
              (D) TOPOLOGY: linear (ii) MOLECULE TYPE: protein (xi) SEQUENCE DESCRIPTION: SEQ ID NO:8:

Ser Phe Trp Gln Phe
1               5

(2) INFORMATION FOR SEQ ID NO:9:

(i) SEQUENCE CHARACTERISTICS:
              (A) LENGTH: 20 amino acids
              (B) TYPE: amino acid
              (C) STRANDEDNESS: single
              (D) TOPOLOGY: linear (ii) MOLECULE TYPE: protein (xi) SEQUENCE DESCRIPTION: SEQ ID NO:9:

Met Lys Gly Leu Leu Pro Leu Ala Trp Phe Leu Ala Cys Ser Val Pro
1               5                   10                  15

Ala Val Gln Gly
            20

(2) INFORMATION FOR SEQ ID NO:10:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

```
Gly Leu Leu Asp Leu
1               5
```

(2) INFORMATION FOR SEQ ID NO:11:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

```
Met Lys Arg Leu Leu Thr Leu Ala Trp Phe Leu Ala Cys Ser Val Pro
1               5                   10                  15
Ala Val Pro Gly
            20
```

(2) INFORMATION FOR SEQ ID NO:12:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

```
Gly Leu Leu Glu Leu
1               5
```

(2) INFORMATION FOR SEQ ID NO:13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

CTGGCTTGGT TCCTGGCTTG TA                                 22

(2) INFORMATION FOR SEQ ID NO:14:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

GCAAGGAGGC TTGCTGGACC TA                                 22

(2) INFORMATION FOR SEQ ID NO:15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

ATCGGTGCCA TCCTTGGGGG TT                            22

(2) INFORMATION FOR SEQ ID NO:16:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

GCAGAGGATG TTGGGAAAGT AT                            22

(2) INFORMATION FOR SEQ ID NO:17:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

GAATTCGCTA GCCAGAGATG AAAGGCCTCC TCCCACTGGC TTGG          44

(2) INFORMATION FOR SEQ ID NO:18:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

CTCGCTCTCG AGGCCCTAGG AGCAGAGGAT GTTGGGAAA               39

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

GGCCACGCGT CGACTAGTAC T                              21

(2) INFORMATION FOR SEQ ID NO:20:

(i) SEQUENCE CHARACTERISTICS:
        (A) LENGTH: 20 base pairs (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:20:

GGCCACGCGT CGACTAGTAC                                                  20

(2) INFORMATION FOR SEQ ID NO:21:

(i) SEQUENCE CHARACTERISTICS:
            (A) LENGTH: 4325 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS
            (B) LOCATION: 722..1195

(xi) SEQUENCE DESCRIPTION: SEQ ID NO:21:

GAATTCCGCC TCCACCTCTC AAATGCTGGG ATTGCAGGAT GTCCCCCCAC CCCTGCTCCC         60

TTGTGTCCTT GCTTCCTGCT GCCGGAATGT ATCACTTAAT TGCCAGGTAC CCATGGTCTG        120

ATTCCAGGAT AGAAGGGCGG GCGAGGGGGT TGGAGGAGAG GCCTCTATTA TTTCCGCGGT        180

CTGGCAGGCC TGGAAGCAAA GCTTCAAGTG CAGAAGGAGG AGTGTCGGGG AATGGCAGAA        240

AAGGCTGGAA CAGCAATGCA GACCTAGGTA AAGGGCACAG AGCTGAGGGA AGCTCCTGGG        300

AGGCTCCCTG CAGCTCCTGC CTCTGCACAT GACCCGGACT CCTTTTCTCT CTTTGGATCT        360

GCGTCCAGGG ACTGGCTTGT ACACACCCCT CCCAGGAGAC CCCTTGGCAG CTGCACACTC        420

AGGCTCCATC CAAGTTGGCT CTGCCCCTGG GGAAGGCTGC TCAAAAGGCC TGGCTCCCAG        480

TTTCTGGGGA CCCACAGAGA GCCTCTCACC TCGCAGCTCA GCTCCATCCG CCTCCTGTGC        540

CTGGCTGCGA CCAGCTGGGT CTAACTATAG ACAGTCAGCA ACTTCAGCCA CTTCACCGAG        600

TTTCCCAACA GCTTTGAGAT TTGGAAGCCG GAAGCCTGAT CGCCTTCTCA GAAGCTACGG        660

TCCACTACCT CAGCCATTCT GTTGGAGCTG AACTGGCAGA TGAAGGTGAG ACCCAGGCAC        720

C ATG GAC CTC CTG GTC TCC TCA GGA ATG AAG GGC ATC GCT GTC TTC            766
  Met Asp Leu Leu Val Ser Ser Gly Met Lys Gly Ile Ala Val Phe
  1               5                  10                  15

CTT GTC TTT ATC TTC TGC TGG ACA ACC TCC ACC CTC AGC AGC TTC TGG          814
Leu Val Phe Ile Phe Cys Trp Thr Thr Ser Thr Leu Ser Ser Phe Trp
            20                  25                  30

CAG TTC CAG AGG ATG GTC AAA CAC ATC ACG GGG CGC AGC GCC TTC TTC          862
Gln Phe Gln Arg Met Val Lys His Ile Thr Gly Arg Ser Ala Phe Phe
                35                  40                  45

TCC TAT TAC GGA TAT GGC TGC TAC TGT GGG CTT GGG GGC CGA GGG ATC          910
Ser Tyr Tyr Gly Tyr Gly Cys Tyr Cys Gly Leu Gly Gly Arg Gly Ile
            50                  55                  60

CCT GTG GAC GCC ACA GAC AGG TGC TGC TGG GCT CAT GAC TGT TGC TAC          958
Pro Val Asp Ala Thr Asp Arg Cys Cys Trp Ala His Asp Cys Cys Tyr
 65                  70                  75

CAC AAG CTT AAG GAA TAT GGC TGC CAG CCC ATC TTG AAT GCC TAT CAG         1006
His Lys Leu Lys Glu Tyr Gly Cys Gln Pro Ile Leu Asn Ala Tyr Gln
 80                  85                  90                  95

TTT GCC ATT GTC AAC GGG ACC GTG ACC TGT GGA TGC ACC ATG GGT GGC         1054
Phe Ala Ile Val Asn Gly Thr Val Thr Cys Gly Cys Thr Met Gly Gly
                100                 105                 110

GGC TGC TTG TGC GGG CAG AAA GCC TGT GAG TGT GAC AAA CTG TCT GTG         1102

-continued

| | | | | | | | | | | | | | |
|---|---|---|---|---|---|---|---|---|---|---|---|---|---|
|Gly|Cys|Leu|Cys|Gly|Gln|Lys|Ala|Cys|Glu|Cys|Asp|Lys|Leu|Ser|Val|
| | | |115| | | |120| | | |125| | | |

| | | | | | | | | | | | | | | |
|---|---|---|---|---|---|---|---|---|---|---|---|---|---|---|
|TAC|TGC|TTC|AAG|GAG|AAC|CTG|GCC|ACC|TAC|GAG|AAA|ACT|TTC|AAG|CAG| 1150
|Tyr|Cys|Phe|Lys|Glu|Asn|Leu|Ala|Thr|Tyr|Glu|Lys|Thr|Phe|Lys|Gln|
| | |130| | | | |135| | | | |140| | | |

| | | | | | | | | | | | | |
|---|---|---|---|---|---|---|---|---|---|---|---|---|
|CTC|TTC|CCC|ACC|AGG|CCC|CAG|TGT|GGC|AGG|GAC|AAA|CTC|CAT|TGC| 1195
|Leu|Phe|Pro|Thr|Arg|Pro|Gln|Cys|Gly|Arg|Asp|Lys|Leu|His|Cys|
| |145| | | | |150| | | | |155| | | |

```
TAGGCCTTCC CCTCCAAGAG TCCCCAGGCT CCTGCAGCTC AGCCTTGCTG TCTAGGGAGT   1255
GTCTTCTCAG GCATTAGGGG ACCGGAGGTG GAGAATTCCT GCCCTGGAAT CAGACCATGG   1315
GTACCTGGCA ATTAAGTGAT ACATTCCGGC AGCAGGAAGC AAGGACACAA GGGAGCAGGG   1375
GTGGGGGAC ATCCTGCAAT CCCAGCATTT GAGAGGTGGA GGCAAGAGGT GGGGGGTAGC    1435
CTCCACTATA CGGTAAGTTC AAGGCTAACC TGAGCTACCT GAGACCTTGC CTTGAAAAAA   1495
CTTTTTTAAA AAACGTTTAA AGGAAAAGAA AACAGAAAGA CACGGGGACT GGGCTGAAAG   1555
GTACTCTCAA ACCGATTTCC CAGGAAGAGC GGAGAGCCCC AGGTTCAGCT CCAGCCTGAA   1615
CTCCCCCATA CCCTCAGTCC TGGTCAGGAT GTGTGTCTGA CTGGGAACC AAGTCCTCCA    1675
CCCGGGTGGA GCTTAGCTGG GAACTACGCA GGTGTCCTAG AAAATACAGT CCTAAGAGCC   1735
TCACCCGGAG TCTCATCCCC ATTTGCTCCA GGACTGACCT CTGTAAATCT TCCAGCAGGA   1795
AGCAGGCTGT ACCCATCTCA GGAGGTGGGG TGCTGTTAGA CAATGGTGT GCACCAGTGA    1855
CACAAAGATG TCATGGTTAA GATGGCATCA AGAAGTGGAA AGGACATTCG AACAGTGGG    1915
TCCAAGGCAC CCAAAGTCCT CACCCCAATT TAGAAGCCGT TGGTCCTGTA AGACTTAAAT   1975
CTACTAAACA AGGAAGGTCT AACTGGGCTG GAATCTGAAG TTCATGGTGC CAGGCTGGGG   2035
CGGTGGGTGG GGACGTGGCC GTGGCCATGA CCATGATTGC CTCTCTGCAT GGTGACACTT   2095
GCCTTTTGCA CCCTAGCTCT CAGCACATCT GAAAAGGACA GACTCTCCTG TTCATTCCTT   2155
GAATCTGAGA CTCTCCTCAC TAATGTAGCA AAAATGGAGG TCTAAAGTGC AGGCTTCAGC   2215
CTCTGAGGTC CAGGGCAGGA GGAAGCTGGG GCTCAGCCTC CTGGAGGATG AGAGCTTGCC   2275
GGGTGAGCAT CAGCGACAGC AGACCCTTGG GCTCAGAGAG TCCGCAAGCC TGGGAGAGCC   2335
TGGCCGAGCC CTGACTGCAG CACACAGAGC CGTGAGCCTC ATACAAGAAG CCACATTTTG   2395
GGGAAGCTTC AGGGTGGCTG ATTCCACAGC TGTTGGGTTC AGAACGGAAG CCGGGAGCAC   2455
TCACTTCAGA TATGGAAGCT TTGTTTTACG AGCGCTTAGC ACCAGTTCAG GATCTGAACT   2515
TCGTCCTGAC CGGAGAGTCC GTACCACATT TTTATAGGAT GGGAACACAG AGCGAGGGGC   2575
GTGGAGTAAG CTGTTGAACG ACCGATCATA TTTTGACCTA AGAGGTTAAG TAAGGACGTT   2635
AACATGGGTG ACTGGGCATT AGTCAGGTCA CCTGGTTTTG GGGTCTTTGA ATCAGCTTTC   2695
GTGGCCAGGT CCCTTCCTGG ACTTTGGCTC GGAATTTAGA ACGATAAGGG AACGAAGAGG   2755
TGGGCAAGCT TCGGGCAGTC AGTAAGAGGC AGCACATTCA TGACCTGTGT GCCTTGTTTA   2815
GATAATGGGA TAAGAGTATC TCCTCTCTTA CACCCCTTAC TGGTTAACAG ACAAACACGA   2875
GACATCTGAA GAAGCAGGAC AGGAGTTAGG TTCTGGGGCA CAGGAACATG AACTCGGTTT   2935
TGATCCTGCC GGCAAGGTGG ATCTTGTTCC TGAGAAGGCT GGACTCAGGA AACTTCCTCT   2995
TAACAAGTTA GTTGATGGCG CTGGTCCTTA GTCACCGATA CTGTCAGGCT CTCAGCTCTT   3055
GGGCCAGACT TGGCGGCCAT GGGAGTGTGG TCACTTGCCC CGTCCCCTTC TTCCAGGAGG   3115
TACTGGGGAA AATGGTTGGA TTTGTGGAGT TGTAGGGAAC ACTCATGGCT CCCTTCACTT   3175
AGTAGGTCAG CTAACATATG TGTATCGAGC CCATACCGTG TGCCATGTGC AGTGCTGAGC   3235
AGCAGGGAGT CAGAGATTTA AAGACACACA CACAGACTTC AAGTCTGAGA ATTTTGAATC   3295
```

```
CCAGGGAGAA CCGCTGAGAG CCATGGCGCT TCTACCAATG CCAGAGGCTA ACACCCGGAC      3355

TGAGAAAACT AAGCACGAGG AGACAGCAGG GTCAGCAGAG GGCCTGGGAG CTAGGGCCCT      3415

GAGCAGTACC TAGTTCAAAT CACAGAGTCG TCTTTCTTCC TCCACCCTAC CCAGGTACAG      3475

CAAGTAGACA CGGGTGGGGG CAGGGCAGGG ATGCAGGAAC ATTAGGGCAC ACCGATGTGG      3535

CTAGGCTAAG CTAGAGCATG TTACCTTCTC AGGGGTCCTG TCATGTCAGA GACTGGTTCC      3595

AACCTGGAAA GATGTCTGAG TGACAGCTGT GGTAGAAGAA GAGAGGCCAG GGTGATATCA      3655

GCATGAAGGG CTGGATTGCT ATGTGAGATC CAGATCTCTT CTGCCACTGG GGTCAGCTTC      3715

TACACTGGAA ATAGATGGGC TGCGTTATGG AGGGTGGTGT GAGTCCCTGT CTGCGTTGTG      3775

CCGGGAATCA GAGCAGAGTG TTAGCGCTGT AAAAGGACAT GCTGGTGTTT GCAGGAAATC      3835

ATCGATTTCT TGGAAGGGCA GCCATTCATC TACACCAGGG ATTGACTTTA TGCCAGGCTT      3895

GTGATGAGGG TAGAAAAGTA GAAATTCTGT CCGCTGCAAG GAGCAGTCAG AGGACACAAG      3955

GACCAAATAG CTTGGGAGTT GCGGAAGTAG GTGTCTGCTG AGGGAGCAGT GACCACTGGG      4015

GGAAAGGCTC CTTCAAGGAA TTCAGGGACA GGGGTGAGGG CTGACATCTT GCCTGAGACC      4075

CTAAAGAAGA GAAGGAGTTG AGAGGGCTGA GTATGCTGTG TGGAGCCCCA CCCCCACCCC      4135

CACCCCCACC CCCACCCCAG GTATATGGAT GGAGGATAAT GCGGGGTCG GGTTCCTCTC       4195

AAATCCATCA TCCCACCTTC GAGCTGCTGG CACGGCCTTG CCAGCACAGC CCGATTCTGT      4255

GTTGACAAAA TACTCGAACG AAATGATTAC ATGCAAATAA AATGCAAGAG GAAAAATCTA      4315

AACGGAATTC                                                            4325
```

(2) INFORMATION FOR SEQ ID NO:22:

(i) SEQUENCE CHARACTERISTICS:
(A) LENGTH: 158 amino acids
(B) TYPE: amino acid
(D) TOPOLOGY: linear (ii) MOLECULE TYPE: protein (xi) SEQUENCE DESCRIPTION: SEQ ID NO:22:

```
Met Asp Leu Leu Val Ser Ser Gly Met Lys Gly Ile Ala Val Phe Leu
  1               5                  10                  15

Val Phe Ile Phe Cys Trp Thr Thr Thr Leu Ser Ser Phe Trp Gln
             20                  25                  30

Phe Gln Arg Met Val Lys His Ile Thr Gly Arg Ser Ala Phe Phe Ser
         35                  40                  45

Tyr Tyr Gly Tyr Gly Cys Tyr Cys Gly Leu Gly Gly Arg Gly Ile Pro
     50                  55                  60

Val Asp Ala Thr Asp Arg Cys Cys Trp Ala His Asp Cys Cys Tyr His
 65                  70                  75                  80

Lys Leu Lys Glu Tyr Gly Cys Gln Pro Ile Leu Asn Ala Tyr Gln Phe
                 85                  90                  95

Ala Ile Val Asn Gly Thr Val Thr Cys Gly Cys Thr Met Gly Gly Gly
            100                 105                 110

Cys Leu Cys Gly Gln Lys Ala Cys Glu Cys Asp Lys Leu Ser Val Tyr
        115                 120                 125

Cys Phe Lys Glu Asn Leu Ala Thr Tyr Glu Lys Thr Phe Lys Gln Leu
    130                 135                 140

Phe Pro Thr Arg Pro Gln Cys Gly Arg Asp Lys Leu His Cys
145                 150                 155
```

(2) INFORMATION FOR SEQ ID NO:23:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

```
ACCTCAGACC CCCTGGTCTC CTCAGGAATG AAGGTCATTG CCATCCTCAC CCTCCTCCTC      60

TTCTGCT                                                                67
```

(2) INFORMATION FOR SEQ ID NO:24:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

```
ACCATGGACC TCCTGGTCTC CTCAGGAATG AAGGGCATCG CTGTCTTCCT TGTCTTTATC      60

TTCTGCT                                                                67
```

(2) INFORMATION FOR SEQ ID NO:25:

(i) SEQUENCE CHARACTERISTICS:
        (A) LENGTH: 151 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

```
TGGTGGCAGC CCCCACCCAC AGCAGTTTCT GGCAGTTTCA GAGGAGGGTC AAACACATCA      60

CGGGGCGAAG TGCCTTCTTC TCATATTACG GATATGGCTG CTACTGTGGG CTTGGGGATA     120

AAGGGATCCC CGTGGATGAC ACTGACAGGT G                                    151
```

(2) INFORMATION FOR SEQ ID NO:26:

(i) SEQUENCE CHARACTERISTICS:
        (A) LENGTH: 151 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

```
CAGGGACAAC CTCCACCCTC AGCAGCTTCT GGCAGTTCCA GAGGATGGTC AAACACATCA      60

CGGGGCGCAG CGCCTTCTTC TCCTATTACG GATATGGCTG CTACTGTGGG CTTGGGGGCC     120

GAGGGATCCC TGTGGACGCC ACAGACAGGT G                                    151
```

(2) INFORMATION FOR SEQ ID NO:27:

(i) SEQUENCE CHARACTERISTICS:
        (A) LENGTH: 170 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

```
TAGGTGGATG CACCCTTGGT CCTGGTGCCA GCTGCCACTG CAGGCTGAAG GCCTGTGAGT      60

GTGACAAGCA ATCCGTGCAC TGCTTCAAAG AGAGCCTGCC CACCTATGAG AAAAACTTCA     120

AGCAGTTCTC CAGCCGGCCC AGGTGTGGCA GACATAAGCC CTGGTGCTAG               170
```

(2) INFORMATION FOR SEQ ID NO:28:

(i) SEQUENCE CHARACTERISTICS:
        (A) LENGTH: 167 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

```
CAGGTGGATG CACCATGGGT GGCGGCTGCT TGTGCGGGCA GAAAGCCTGT GAGTGTGACA      60

AACTGTCTGT GTACTGCTTC AAGGAGAACC TGGCCACCTA CGAGAAAACT TTCAAGCAGC     120

TCTTCCCCAC CAGGCCCCAG TGTGGCAGGG ACAAACTCCA TTGCTAG                  167
```

(2) INFORMATION FOR SEQ ID NO:29:

(i) SEQUENCE CHARACTERISTICS:
        (A) LENGTH: 1828 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 233..643

(xi) SEQUENCE DESCRIPTION: SEQ ID NO:29:

```
GAATTCCGGT GGATGGAGGG GGCTGAGCAG GATGTTGACT GGCTATCGTT CATTGAGCAC      60

TCTCACGATC AGCATCACGC ACGGAATCCA TCCTTCCTGT GTTGCAGCTT GTAGACCCTG     120

ATGCTTGGGC TGCCAGCATA AACGTGGGGA TCCAGACTCT GTCTACCGAG CTGCCCATA     180

GGGACAGGCC CTGGGAAGAG GAGCTGAGAC CAGGCTAAAA AGAACCCAAG AA ATG          235
                                                          Met
                                                           1

AAG CGC CTC CTC ACG CTG GCT TGG TTC CTG GCT TGC AGT GTG CCT GCA      283
Lys Arg Leu Leu Thr Leu Ala Trp Phe Leu Ala Cys Ser Val Pro Ala
            5                  10                  15

GTC CCA GGG GGC TTG CTA GAA CTG AAG TCC ATG ATT GAG AAG GTG ACT      331
Val Pro Gly Gly Leu Leu Glu Leu Lys Ser Met Ile Glu Lys Val Thr
        20                  25                  30

GGG AAG AAT GCC GTA AAG AAC TAT GGC TTC TAC GGC TGC TAC TGT GGC      379
Gly Lys Asn Ala Val Lys Asn Tyr Gly Phe Tyr Gly Cys Tyr Cys Gly
    35                  40                  45

TGG GGC GGC CAC GGG ACC CCT AAG GAT GGC ACT GAT TGG TGC TGT CGG      427
Trp Gly Gly His Gly Thr Pro Lys Asp Gly Thr Asp Trp Cys Cys Arg
 50                  55                  60                  65

ATG CAC GAC CGT TGT TAT GGG CTA CTG GAG GAG AAA CAC TGT GCC ATC      475
Met His Asp Arg Cys Tyr Gly Leu Leu Glu Glu Lys His Cys Ala Ile
                70                  75                  80

CGG ACC CAG TCC TAT GAC TAC AGA TTC ACA CAG GAC TTA GTC ATC TGC      523
Arg Thr Gln Ser Tyr Asp Tyr Arg Phe Thr Gln Asp Leu Val Ile Cys
            85                  90                  95
```

```
GAA CAC GAC TCC TTC TGT CCA GTG AGG CTT TGT GCT TGT GAC CGG AAG      571
Glu His Asp Ser Phe Cys Pro Val Arg Leu Cys Ala Cys Asp Arg Lys
        100                 105                 110

CTG GTC TAC TGC CTG AGG AGA AAC CTC TGG AGT TAC AAC CGT CTT TAC      619
Leu Val Tyr Cys Leu Arg Arg Asn Leu Trp Ser Tyr Asn Arg Leu Tyr
        115                 120                 125

CAG TAT TAC CCC AAC TTC CTC TGC TAATGTCCTC TGTGGGCTCT CGCCGGGAGT     673
Gln Tyr Tyr Pro Asn Phe Leu Cys
130                 135

GCCTCCCACA GTGGCGGCCC CCCTCGGCTG TATTCCTGAT CCGTCCACCC AAGGTCTTGG    733

ATCTGCCTTC CTCTGTGTAC CACTGGGCTG GACAGAGCCC AGGGTTACAC CCTACCCTCC    793

AGAATCCTAG AGAGGGACTC TGATGTAGAG TCTGCGGACT CTGGATAGCT GAGCCTGCAC    853

TTGCAGAATT TGGCGCTGGG CCCCGGAGCT CCCTCAGCTC CAGGCCAGTG TCGTGTTGAC    913

TTTCCTTTCA ATTTCTGGAA CCCAACTGCC ATTACCACCC TCCAGAGACC TCTTACTAGA    973

GGAGAAGCCA AATTAACTCT ATAAATCTGC CATGTAGCTA TTAAATAAAA CCCATTCACG   1033

AGGCGAGAAG AACACCACCC CAGCACTCCC TCTGACAGGG CTGGGGTAGG AGTGCCAATG   1093

CTTCTCTAAC CCCTGAGGCA TCTGTGCACC CTCTAGGATG GAGGTCAGGA AACAGGTGGG   1153

GGCCTTACAT GCCTTTCATG GTTTGTCTTG AGTTTATTTT CTTAAACCTT AGGGTCTTTC   1213

AAGCCAGACC TGGAGCTCAA GATTCTTCTG GAGGAAGGTG AGACACAGCC CTATGCCACC   1273

TTGAGCTCCA GGCTAGAAAG GGACAGCCCC TAGCCCTGGC TTCTGCAACT GTGTGGTCTT   1333

GAACCTCCGT ATAGTCCGAA TCCCTCTGGC TCTCCTCAAA ATATAAAACA AGCCTCCTTC   1393

CAATAGCATA TTGGTGCACA CCCCTAATCC CATCACCTGG GAGGAGGAGG CGGCAGGAGC   1453

ATCAGGAGTT CAAGGCCAGC TCCTGCCCCC TAGCAGGGAT GGTAGGCTGC ATGAGAGTGT   1513

GTCTCAGAAA GAACCACCTG GTGCGGGTAC AGGGATGCTG GGATTCTGAG ATGTCACTCA   1573

GTGCGGGAAA AGATTCAAGG AGGGGAACAG ATCAATGGCA GAATGACTGT CTGTGCCGAG   1633

TTAAGGGCAC TGAAAATCTC AGCTCATCTA TCGCTTTATA GAAGATAGAG CTTTGGGAGG   1693

AAGCAAGGCA CTCTACAGTA AAGGAGTGGC CTTTCCAAGG AAGGGTCTAG GCTCCTTCTT   1753

CTCCAGAACA TGCACAGGAC ATAGGAGATC CATTATTTAG AGACCTTTCG TGTTCGAACG   1813

TTTTCTCCGG AATTC                                                    1828
```

(2) INFORMATION FOR SEQ ID NO:30:

(i) SEQUENCE CHARACTERISTICS:
        (A) LENGTH: 137 amino acids
        (B) TYPE: amino acid
        (D) TOPOLOGY: linear (ii) MOLECULE TYPE: protein (xi) SEQUENCE DESCRIPTION: SEQ ID NO:30:

```
Met Lys Arg Leu Leu Thr Leu Ala Trp Phe Leu Ala Cys Ser Val Pro
1               5                   10                  15

Ala Val Pro Gly Gly Leu Leu Glu Leu Lys Ser Met Ile Glu Lys Val
                20                  25                  30

Thr Gly Lys Asn Ala Val Lys Asn Tyr Gly Phe Tyr Gly Cys Tyr Cys
            35                  40                  45

Gly Trp Gly Gly His Gly Thr Pro Lys Asp Gly Thr Asp Trp Cys Cys
        50                  55                  60

Arg Met His Asp Arg Cys Tyr Gly Leu Leu Glu Glu Lys His Cys Ala
65                  70                  75                  80

Ile Arg Thr Gln Ser Tyr Asp Tyr Arg Phe Thr Gln Asp Leu Val Ile
```

```
                    85                  90                  95
Cys Glu His Asp Ser Phe Cys Pro Val Arg Leu Cys Ala Cys Asp Arg
            100                 105                 110

Lys Leu Val Tyr Cys Leu Arg Arg Asn Leu Trp Ser Tyr Asn Arg Leu
        115                 120                 125

Tyr Gln Tyr Tyr Pro Asn Phe Leu Cys
    130                 135
```

(2) INFORMATION FOR SEQ ID NO:31:

(i) SEQUENCE CHARACTERISTICS:
        (A) LENGTH: 1014 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 131..544

(xi) SEQUENCE DESCRIPTION: SEQ ID NO:31:

```
GGATACCAAT GTTCCGACTG GAGACGGGGA GCCCGCGAGA CCCGGGTCTC CAGGGTCTGC     60

CCAAGGAAGT TGCTCATGGG AGCAGACCCC TAGAGCAGGA TTTGAGGCCA GGCCAAAGAG    120

AACCCCAGAG ATG AAA GGC CTC CTC CCA CTG GCT TGG TTC CTG GCT TGT      169
           Met Lys Gly Leu Leu Pro Leu Ala Trp Phe Leu Ala Cys
             1               5                  10

AGT GTG CCT GCT GTG CAA GGA GGC TTG CTG GAC CTA AAA TCA ATG ATC      217
Ser Val Pro Ala Val Gln Gly Gly Leu Leu Asp Leu Lys Ser Met Ile
     15                  20                  25

GAG AAG GTG ACA GGG AAG AAC GCC CTG ACA AAC TAC GGC TTC TAC GGC      265
Glu Lys Val Thr Gly Lys Asn Ala Leu Thr Asn Tyr Gly Phe Tyr Gly
 30                  35                  40                  45

TGT TAC TGC GGC TGG GGC GGC CGA GGA ACC CCC AAG GAT GGC ACC GAT      313
Cys Tyr Cys Gly Trp Gly Gly Arg Gly Thr Pro Lys Asp Gly Thr Asp
             50                  55                  60

TGG TGC TGT TGG GCG CAT GAC CAC TGC TAT GGG CGG CTG GAG GAG AAG      361
Trp Cys Cys Trp Ala His Asp His Cys Tyr Gly Arg Leu Glu Glu Lys
         65                  70                  75

GGC TGC AAC ATT CGC ACA CAG TCC TAC AAA TAC AGA TTC GCG TGG GGC      409
Gly Cys Asn Ile Arg Thr Gln Ser Tyr Lys Tyr Arg Phe Ala Trp Gly
     80                  85                  90

GTG GTC ACC TGC GAG CCC GGG CCC TTC TGC CAT GTC AAC CTC TGT GCC      457
Val Val Thr Cys Glu Pro Gly Pro Phe Cys His Val Asn Leu Cys Ala
 95                 100                 105

TGT GAC CGG AAG CTC GTC TAC TGC CTC AAG AGA AAC CTA CGG AGC TAC      505
Cys Asp Arg Lys Leu Val Tyr Cys Leu Lys Arg Asn Leu Arg Ser Tyr
110                 115                 120                 125

AAC CCA CAG TAC CAA TAC TTT CCC AAC ATC CTC TGC TCC TAGGCCTCCC       554
Asn Pro Gln Tyr Gln Tyr Phe Pro Asn Ile Leu Cys Ser
                130                 135

CAGCGAGCTC CTCCCAGACC AAGACTTTTG TTCTGTTTTT CTACAACACA GAGTACTGAC    614

TCTGCCTGGT TCCTGAGAGA GGCTCCTAAG TCACAGACCT CAGTCTTTCT CGAAGCTTGG    674

CGGACCCCCA GGGCCACACT GTACCCTCCA GCGAGTCCCA GGGGAGTGAC TCTGGTCATA    734

GGACTTGGTA GGGTCCCAGG GTCCCTAGGC CTCCACTTCT GAGGGCAGCC CCTCTGGTGC    794

CAAGAGCTCT CCTCCAACTC AGGGTTGGCT GTGTCTCTTT TCTTCTCTGA AGACAGCGTC    854

CTGGCTCCAG TTGAACACT TTCCTGAGAT GCACTTACTT CTCAGCTTCT GCGATCAGAT     914
```

```
TATCATCACC ACCACCCTCC AGAGAATTTT ACGCAAGAAG AGCCAAATTG ACTCTCTAAA      974

TCTGGTGTAT GGGTATTAAA TAAAATTCAT TCTCAAGGCT                           1014

(2) INFORMATION FOR SEQ ID NO:32:

(i) SEQUENCE CHARACTERISTICS:
        (A) LENGTH: 138 amino acids
        (B) TYPE: amino acid
        (D) TOPOLOGY: linear (ii) MOLECULE TYPE: protein (xi) SEQUENCE DESCRIPTION: SEQ ID NO:32:

Met Lys Gly Leu Leu Pro Leu Ala Trp Phe Leu Ala Cys Ser Val Pro
 1               5                  10                  15

Ala Val Gln Gly Gly Leu Leu Asp Leu Lys Ser Met Ile Glu Lys Val
                20                  25                  30

Thr Gly Lys Asn Ala Leu Thr Asn Tyr Gly Phe Tyr Gly Cys Tyr Cys
            35                  40                  45

Gly Trp Gly Gly Arg Gly Thr Pro Lys Asp Gly Thr Asp Trp Cys Cys
        50                  55                  60

Trp Ala His Asp His Cys Tyr Gly Arg Leu Glu Glu Lys Gly Cys Asn
65                  70                  75                  80

Ile Arg Thr Gln Ser Tyr Lys Tyr Arg Phe Ala Trp Gly Val Val Thr
                85                  90                  95

Cys Glu Pro Gly Pro Phe Cys His Val Asn Leu Cys Ala Cys Asp Arg
            100                 105                 110

Lys Leu Val Tyr Cys Leu Lys Arg Asn Leu Arg Ser Tyr Asn Pro Gln
        115                 120                 125

Tyr Gln Tyr Phe Pro Asn Ile Leu Cys Ser
    130                 135

(2) INFORMATION FOR SEQ ID NO:33:

(i) SEQUENCE CHARACTERISTICS:
        (A) LENGTH: 15328 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

AAGCTTTGTG GGATTTCTAT TATGAACAAC ATAGGTGCCT TTCCAACTCG GGAACAGAGG        60

AAATATGGAC TCCTCAAAAG AAAAAAAGAA GAGATGAAGG GATGATGTTG CCAAAGAAAG       120

AAATTTGGAA AAAAAAAAAC CAAACCAACA TTTGCACTTT CAAAACCATG GAACCCTTCT       180

TATTTTTATA TGTTCAGATC TAAATGCCAG AAAGGTTACC ACATTCAAAG GAATGAGAT        240

TTGAAAATGA TTTCTTTGAG TCCTCTGCTG AGGTCTTTCC AAGGCACTAC AATTAGGGCT       300

TTGCACCCAA ATACCCTTGC CTCATTTTGG TCATTTTTGT CCTGGAACAG AGGTTCAGCT       360

GGGAGACCCC TCACACACAG GTGAAGGCGT GGCTGTAGAA CCTCAGACCC CCTGGTCTCC       420

TCAGGAATGA AGGTCATTGC CATCCTCACC CTCCTCCTCT TCTGCTGTAA GTAGAGAGCG       480

TTGGTGGGTC AGCACCAAGC TTCTGTCTTC CTGTTTATGT CAGTGGGAGG GGGACTCTC        540

CAGGTGGCAC CAGGTGAGGG AAGTCACAAG TCCCGCAGAA AAGAATCAGG AAAGGAACGG       600

GCTCCCACCA ACGTCCTCTT GCTTCTGTTT CTGCTATAAA ATGGGCTGAT CCAGTGTTG        660

GGATCTTATA AAGTGTCTAG GAAATCAGAG GTTGCCAACC ATTTGCTAGA AAGGGAGTTT       720
```

```
GAGTAGTATT TTACCCCCCC TCACCCTCAA GAGTCTTTTT ACTTTGGATG CTAGTAGCCT      780

TTTATTTAGG CATTGGATCA GAACAAAAAT GCAGGACATA TATCCAGCCT AATTTAACCA      840

ATGGATTAAA TGGCCTTATC AGGAAAAGAC CATTTTATGG TGACTTATGG GATAATTGGT      900

AGTTATAAGT CATTGCTGCC GGGAGATCCG ATTGCTTACC TCTGCAAAGT GAAGAAAGAC     960

CTACTGGGAA ACAGTTTGGG GTCTACTGGA GACTGATAGA CTCTTTTGCT GGATTCGTTG    1020

AGTGGAGGTT TCTCCAGATC CATTTTCCTG TCTCTTTCAA TTGAGTCACA ATAACTTTTG    1080

AGTCCCTAAG TCAAAGATGT CAAAAACAGA CTTCCTTTCC CCACAGTGAG TGGTGGAATT    1140

TACACTTTGC AAGGTGATAG TGCAGGAGGA TACCTGTACG CAGGGATGAC CGCCTCTGCA    1200

GCCCTCAGTG CGGCTCCAGG ACTGCTTGGG CACCAGTGAC CGCCCCATGG GTTTCTTCCG    1260

CCACACCCCC GTTTAGACTG AACACGATAG GTAGATCGAA GGCCACCTGA GAAAACTCCC    1320

CCAAAACTCT ATTTCTGTTT CTCTTCTTCA AAGTTCATGT CTTTGTTGTA TTTTTATTGC    1380

AAATTTACTA CATGCTTATA GTTAAAAAGT AAAATAAATG AGTATATAGC AACAAGGTAA    1440

AGCTCCTCCT CATCCTCCCC AGACCCCAGT TTTTTCCCTA CATCCAGATG TGACCACTCT    1500

TAAGAGTTTG ATATACATCC TCTATACAGC GTTACCACA CACACATTCA AAACACCATA     1560

ATAGGAAGGG AACACATGCT GGGCCGGGCG CGGTTGTTCA TGACTATAAT CCCAGCACTT    1620

TGGGAGGCCG AGGCGGGCGG ATCACCTGAG GTCAGGAGTT CGAGACCAGC CTGGCCAGCT    1680

GGCAACATGG TGAAACCCGT CTCTATTAAA AATACAAAAA ATTAGTCAAG CATGGCAGTT    1740

GGGCACCTGT AATCCCAGCT ACTCAGGAGG CTGAGGCAGG AGAATTGCCT GAACCCGGGA    1800

GGCGGAGGTT GCAGTGAGCC GAGATCACAC CATTGCACTC CAGCCTGGGT AACAACAGCG    1860

AAACTCCGTC TCAAAAAAAA AAAAAAAGA AGGAAAGGGA CACACGCTTA TTATGAAAGA     1920

CATGAGACAG CGGAGACGTG TATAAATGAT GTTGCCTGTT TTCTTTCTCT CTCTTCATCC    1980

ATGCTAGAGA TAGTGCTATC AAATGTAGTT ATTTTTGAGA CACATATTTC GTATTATCCC    2040

TGTCGTGACA TGTGGGTGGT TTCCAATTTT TTGATATCAC AGATAATGCT TCAGGAAACC    2100

ATTTTGTGTA TCGATTTGTG CCCACTCTCA TAAGCATCTT GTAGAAGCAA AAACAGCTGA    2160

GTTCATGTGT ACTTGTCATT TAAAAAAATA ATAATTGAGG ATACCTTTCC TGCCTCTTAA    2220

GTATTTTGTT TCTCCTGTGA GATAGTAAAG GCCTGATGAC ATCTGGAGGG ACTGGCGTTT    2280

CTGGCTTTGA ACTTTTGCCA TTCATGTTGC ATCAGACCCG AGGGTGTTCT GCCTAGAACT    2340

GTGGTTTCTT GCTTTGAGGG GGAAGACTAT GGTTGATGGG AAAGCCTTGT TCTGAACCTC    2400

ATGGAAACTG GGTATTCATC TGGGTTAGCA AAAAACTAGC TGTGTTACAG GGGCAAATCT    2460

GAACCTATTT TATTCCCCAG GAAAGAGGCT GGTGATTCCA GCCATGCCCC TTGCACTTCG    2520

CTTTGGGGAT CTGGTGATAT TTCGAATGCT CAGCACTCTA GTAAGGGGAG GGGACATCAA    2580

GGCAGCATCA TGCTCATTGC AACTTCCTTC TTCCTTTTTT TCTCATCGGT GGTGGCAGCC    2640

CCCACCCACA GCAGTTTCTG GCAGTTTCAG AGGAGGGTCA AACACATCAC GGGGCGAAGT    2700

GCCTTCTTCT CATATTACGG ATATGGCTGC TACTGTGGGC TTGGGGATAA AGGGATCCCC    2760

GTGGATGACA CTGACAGGTG GGTGCAGAGG CTCTAAGGCC ACTTATCATT TGTTTTGCAT    2820

TAAAGTTCAT GCTCAAAGCC AGAGAGAGGG TCTTAGGATT CTTGCCTGGC AAATAACAGA    2880

AAACAACTCA GGCTAATGGA AGGAAGAACT GAACGGGATT TGGAGGATGG GTCTTGAGAA    2940

ACCCAGGGTC GGGGCCAGCT TCTTGAGTGT GTGACCTGTG AAGTTTCACA GGGCCCAACA    3000

CTCATAAGGG TCAGGGCCAG CTTCTTGAGC GTGTGATCTG TAAAGTTTCA CAGGGCCTGG    3060

CACTCATAAC CCCCTAAACA TGGTTTACTG CTCTGCTGCC ACATCTTGAA ATTCTTAATA    3120
```

```
AAGGGCCTCA TGTTTTCATT TTGCTTTACT CTCTGCAATT ATGCCGTTGG TCCTGCCCAG      3180

AGCTCTAGAA GCTGTTTCAT CCTCATAGTA AAAGTGCTCT GCTTTCAGCT CTCCAGCTTT      3240

TAGCACTATA CCCACAGCAC AACTGACTCA CTAGTCCTAA TTCCATATTC TGGAGAGGGC      3300

TCCAAAGTGG CCCACTTTGG AGAAGTTGTC CATCTGGGTG AGGTTGCATG GCACAAACCT      3360

GGCTTCAGGC CTACTCCAAA GGATGGGGGT GGGGAGTGT GAGTTCCTAG AAAAAGTAGA      3420

GGTGGGTGTC ATCTGGTGAA TGTACGTGTG GGGAGGTAAG AAACGGGACA GTTTGCGTCT      3480

CAATTCATTT GAAGACATAA GAAAGCAAAA TGTTCCTTGC CACATTTAAG GTAGTATGGA      3540

GAAACATGTC CCACAGTGGC CTTAAATATC ACTCTGAGCT CGAGTCTTGT GGTGGCTCAT      3600

GAACCATGGA GGACCTAGAG GTTCGAAGGG CAATTGACGC TTATCAAATG CCCTTATGTG      3660

CCAAGCACTG GGACTGGCCG ATTGGCATAC AAACCTAATT TAATTCTCGC AGGGAATGCA      3720

CGACACAGTT GATACCAGCC CATTTGACAG CCTGAGGACA TGTGAGTTGC TAAACCACCT      3780

CCTAAAGGCA ATGCAGCTTC TAAGTGGCAG AGTTTAGGAT TGAACGAGAA TTTGCCTATT      3840

TCAAAGTTTG TCCCCTCTCC TTGATGGTCT GTGCCTCCCC TGTCAAAGTC CAAAGGCTGA      3900

TTAGAAATTG AACATCATTA GCCAAAGCTG ATCAACAGCA GAGCCCCCAC TTGCAGATGG      3960

GAATGGTGAG AGAGGGAGAC TGAAACACTT TTTTCTTGGC CTTTCAGGGT TTAGAATCCA      4020

AGCTTAAGTT TCTGCCTTCC TGTCCCTTGT GTAGTGGTTG AGGACATGGA CTGAGCCCAT      4080

GCTCCAGATG GTATTTCTCC TCCAGTGCTC TCCCATCCAG CCCCCAGCCA ACTCTGGGTG      4140

CCATGAATGG GACTACGTCG GCTTTTACAG ACAGTTGTCT CCTCAGAGAC CGTTACAGTG      4200

CCTGACTCAC AGTAGGTGCT CAGTAAAAAG TGTTAAATGA ATGAATGGGC CTAGGTTTGT      4260

GTCCTGGGTC TATCATTCTC CAGCTGCCTA AGTTTGGGAA ATTGGCCTCT TGGAATCTCA      4320

GTCCCTCCCC TACAAAAGGG CAGCAATGAT TGTACTTTAT AGTTCTAGT AGCTAATGAG      4380

ATAGCAACAG ATACTACAGA GGGCTCAGGA AATGCTACTG GTTATTATTA TTATTTTTA      4440

TTTTATTTAT TTTTTGGGAG ACGGGGTCTT GCTCTATTAT CCAGGCCTGG GGTGGAGAGG      4500

CTCAATCAGA GCTCACTGCA GGTCCTCAAG CAATCCACCC ACTTCACCTC CTGAGTAGCC      4560

GGGACCACAG GCTGGTGCCA CCATGCCTGG CTTTTTTTTT TTTTTAAAC TTAAAAAACA      4620

TAGGCGGCTC CCTATGTTGC CCAGGCTGGT CTCAAACTCC TGGACTGAAG CGATCCTCCT      4680

GCCTTATCCT CACAAAGTGC TGGGATTGCA GGCATGAGCC ACCACACCTG GCCTATGTTT      4740

AATATTATTG ATAATTCACC TCCTCACCTT CAATGCCTTC TTGCCTAGAG GAGGAGGCAG      4800

GTGAGCCCTT TCTAGTCCCC AGATAAGGTC CTCCAGCAGA TTCCTGAGGG ACCCACTTCC      4860

AGGCACAGCC CCTCATCTCC CTCTCCCTAC GAGAAGCTGA AGGAGTTCAG CTGCCAGCCT      4920

GTGTTGAACA GCTACCAGTT CCACATCGTC AATGGCGCAG TGGTTTGTGA GTAGCCTTTT      4980

CTGTATGGAA ATGTCTTTTA ACCTGGGCCT TTCCTTAACG TTCACCTCCT CTTTGACCCA      5040

GAGATCTTTT AGAAAATGAA ATGCTTCCAA GTGCTTGGAA GGAGATATTC CTGAGCTTTC      5100

TCCTGATGCT CCAGAGCTTC TCAGAGTGTC CGTGCTCATC CTGCCCTGGT CTCTCCCACC      5160

CATGAGTGTA CCTCCTGAAC TCTCTGGGGG CCCAGAGCCT GGCAGATAGT ACATGCTCAG      5220

TAAATACTTG TTCACTTGAG CTAATCTTGA AGCTTCCCTT GACAACTGCT GCTGTTGAGA      5280

ACATGTTTCC TTGTTTCTGT GATTTTGTTA ACAAAACGGC TCAGCTGTCT TCCAGTTGGA      5340

CAAATATTTA TTAAGGGCGA CTGCATGCCA AGCACTAAGA TAGGTGCTGC CAGGGCCACA      5400

AAAGCAAATA GGTGGGAAGG GAAGGGGGAC TCACATGTTA CTGAGACCAT TCAAGGAGCC      5460

ATGTGGGCAA GTGGATCAGT GCCCTTCACA TGGGGCGTGG CCTGGCATCC GGAGCGTGTT      5520
```

-continued

```
CTGCGGCTGG TAGGGTATGG GTATGTGCAG GGCAATCCTG GCCTAGACAG CAGGCACATT    5580

TGGAGGCACG GGACAGTAGT CTTTCGTGAG CACCATCCTT TCCAGCATAG CCAGGGTGGA    5640

TCCTGGGGTC CTGGGCTGGG AGGGTGAAGA GCAACAAATA AAGAAGTGGC TTCTTGGCCG    5700

GGCGCGGTGG CTCACGCTTG TAATCCCAGC ACTTTGGGAG GCCGAGGCGG GCGGATCACG    5760

AGGTCAGGAG ATCGAGACCA TCCTGGCTAA CACGGTGAAA CCCCGTCTCT ACTAAAAATA    5820

CAAAAAAAT TAGCCGGGCG TGATGGTGGG CGCCTGTAGT CCCAGCTACT CGGGAGGCTG     5880

AGGCAGGAGA ATGGCGTGAA CCCGGGAGGC GGAGCTTGCA GTGAGCCGAG ATTGCGCCAC    5940

TGCACTCCCG CCTGGGCCAC AGAGCGAGAC TCCGTCTCAA AAAAAAAAAA AAAAAAAAG     6000

AAGAAGTGGC TTCTTATAGT GTGTGGCTCA CTTCCTGCCT GGCCTCGTGG GGTTGCATGA    6060

ATCACTTTCC TTCCCAGGTG TATTTATTCA GAGCTGTGAG TGCACCTTGG AGTTCCTCTG    6120

TTTCCTCCTG AGGTCAGGGA ACTACCACCT CTCTGCCACT CATCCCCTAT GGCGGGAGAT    6180

ACATCCTCCA TCCCGTAGTG GGTTCCAGGG CTCAGAACCC TGGTACTCCT GAGCTCCCCA    6240

ACCCACCACT TCAGCTCAGC ACACACCAAT ACCCAGAGTT AGGACTGTGA GGTCTCCCTG    6300

GCACCAGCTG TGTGGGTTGG GGGCTCGGAC CCCTGCACCG GGAGGACCTG CCTCAGCTCT    6360

TGGCCTGCCC TGCCCACTGC CACCAGCACG TGGTTGACAG GGAAAGAACC CCCTTTTGTT    6420

CCCCACGTGA GCTCAAGCAA TCCACCCACT TCAGCCTCCT GAGTAGCTGG GATTACAGGT    6480

GCCCACTGCC ATGCTTGACT AATTTTTTGT ATTTTTAATA GAGACGGGGT TTCACCATCT    6540

TGGCCAGCTC AGCACACACC AATACCCAGA GTTAGGACTG TGAGGTCTCC CTGGCACCAG    6600

CTGTGTGGGT TGGGGGCTCG GACCCTGCAC CGGGAGACCT GCCTCAGCTC TTGGACTGCC    6660

TGCCACTGCC ACCAGCACGT GTTGACAGGG AAAGAACCCC TTTTGTTCCC ACGTGAGCTC    6720

AAGGAGACTT CCCTGAGTTG GAGCTCTCTG GTGTGGTCCT TCTCAGGCCT AAAGCAAAGT    6780

GTCTTTTCTG TGACACCTCC AAGGCCATGT TCAGGAGAGG GGAAGGGATC AGGGCCTGGT    6840

GGGAGGGATG GGGAGAGGGG ACTGGAGAAG GTGGCCTCCA GGGATCGAGT TTCCCATGGC    6900

CTCTTCCCAC CTGTCTTTGC CACAGGGGTG GGGACACCTG GCTGGCCCAG CCCAAGCCTC    6960

CACCCTGGGC TCCTGTGGGC TGGCTGCACT CGCCAGGGCT GGCCTAGGCT CTCTGCACCC    7020

AGGGAAGCTT CTCTATTCAA TGCTCTTCAC CCTCCCAGCC CAGGACCCCA GGAGATGAGG    7080

GAGAGTGGAG CAAAGGTTGA GGAGCAGAGG CTGGAGCCCC AGGCAGTGGC ACTGCTGGGC    7140

AGTGGTGGGA GGTGCCAGCC AGGGCTGGGA GTTGGACCCG AAAGTACGTG GCCTGGGCTG    7200

TACTTTCTTC CCACGTTGCC CCTTCAGAGC AGAAGCAGCC AGTTGCTCCT GAAGCCTTGA    7260

CCAGGGCTCC TGAGTCCAGA GCCTTGCTCA GGGCACTAGC GTGGGAGGAG GCTTCCGCAT    7320

CAGTACAGGG CATCAGCACC CGCCTCCTCA GCTGACCCAG CCCCGTGAGG ACCCAGGCCC    7380

AGCCCCTGT CATCCCCACC CCCACCTTGC CAAGCCCCTG CCCCCAGGAG CAGGGCTGAG     7440

AGCGAGGTGA TCTGGGTTCT AATCCAGAGT CTGCTGCTGA CATGTGCTGA GCCCCAGGCC    7500

CATTGGTTTA CTTGCCCCAG TATTGAGCGA GCATCCACTG GGTACCCGCC CAGTGCCGGT    7560

GCTGTGCCAG GGGCCGGGGC ACAGAATAAA GCAGACCCGT CCCTGCTCTT CTGGCATTCA    7620

CAGTCTTGTG GAAACTCCAG ACTGAAAGTG CCCTTAGAGA TTATCCAGAT CAGCCCCTCC    7680

TTGTAGCAAT GAAGAGACTG AGACCCACAG AGGGGATGAG TTTGATCCAA GAAACAGACA    7740

AGATTAAGAT GCATGTGTCT TGAACCTTTT CAGTGCTCTG GAACATACCG TCTGGCCGGA    7800

GTTGTCTGGG CTTTGGTTTT CCCATCCATG AAATGGGTAC AATAACAACA GCTATAGTGT    7860

ATGAGCCTCT GTGATAGATG CTGTACGCAC AGCACCTGAA CTCACATGAT AAACCACTGA    7920
```

```
GGTGAGCATT ATCTCCCATT ATCAAGGAGG ACCCTGGGGC TCAGAGAGGT TAAGCACGAT    7980

GCCAAGGCCA CACAGCCAGG GAAAGAAGAG TTGGAATTCA AACCCCGGGT GCCCTGTCTC    8040

ACACTAGCTT CCCCTGTGGA GGGTGCTGGT GTGTGCATGA TTGGAGGCCC TCACACAGTG    8100

TAAGTCTCAG GATCTGCAGC AAACTGGTCA GAATGCTCTG CCCTGGCCCA GGGAAGGAAA    8160

GAGGGGCAGA TGGAGTTTGC TTCGCTGTAA GGCCCCGGAG CTTTGTGTTC CTGCTGAGAA    8220

GCCTCAGAGT CGGGCAACAC TGGGTCTAAT TCCAGCTCCA CCCCTTGTAT TAATAGCTGG    8280

GCCTTAATCT CCTCATCTGT AAAATGGAGA GAATCGTCGC CTGTACTTCA TAAGGCTGCT    8340

GGAAGGATTA GCTAAAGCAA CCCAGCTACA GTGGCTGGCC TACAGTAGGT GCTTCATTAA    8400

TGCCCTTCCT TTTAGATGTG GAAATTCCTC TTTTTGTCCA AGTTTTCTTT TCCTCTTTGC    8460

TTACGGCACT GGGATTTTCT TTATTACTGT TTCTTTGAAG AGTCCGCTCT GTACTTGTGC    8520

CCACGGCTAT GGTCAGTAAC CCCTTATGGA ATAAAACCCC TTTCCTGGCC AGGTGTGGTG    8580

GCTCATACCT GTAATCCCAG CACTCTGGGA GGCTGAGGCG GGAGGATCAC TTGAGCCCAG    8640

GAGTTCGAGA CCAGCCTGGG CAACACAGTG AGACCCCTGT CTCTACTAAA CATACAAACA    8700

ATTAGCCAGA TGTGGTGGTG CATACCTGTA GTCCCAGCTA CTCAGAAGGC TGAGATAGGA    8760

GGATCACCTG AGCCCAGGAG ATGAGGCCAC AGTGAGCTGT GATTGCACCA CTGCACTCCA    8820

GCCTGGGCAA CAGAGTGAGA CCCTACCTCA AAAAGAAAGC AACAACAGAA AACCTATTTC    8880

CCTATCCTAA TTGCACCTCC ATTCAAAGAG CTGCCCCTGC AAGAGTTAAC CAACTCCCTA    8940

GCCTCCCATG AGTTCTGAAA TCCTGCACCC AGGCCTGGTC CCAGTTGCCT AGCAACCGGG    9000

GGCTGCTCTG GGATGCAGTA GGTAAGCAGG GGAGGGAGAG GAAGAAAACA ACTTGGTCTG    9060

TCCACGACTC TAAATGTCAC TGAGAGATCA GTGCAGAGAA AGGCCTGTCA CCAGAGCCCA    9120

GGGCCCAATT TGCCTGGTGG TAGGGACAGC TGCCCTCAGG CCACCTGGGA GGTGGTTATC    9180

CCTCCTTTGA GTGGGCTTAC ATAACTACTT GGCATTTTTG CAAGGGACTT TAAGCTCACT    9240

CAGCAGTGAC ACCCCCCTCC GCCCACATGC ACATACATGT GTGGTACAGG GAGGACCCGG    9300

TGTGGGAGGC AGAGATGGGG TTCCAGCCAA CTGAAACTCC ATCATCTGCA TCTCCCGGCC    9360

TCTGACTGCC TCCCTCTGCC AAAGCGGGAA GATGAAAATG GTAACTGCTG GAATTTGTAT    9420

TTTGCAAAGA CTTTTCTCAT TTACTGCTGA ATATATTCCT CATCTCAGCC TCCACTCGCT    9480

GACACGCTAC CCACTGTCTC TCCCAGCATT CATCTCTACC TGAAATGATC TTGTTTACTT    9540

CTCTGTGTCT GTGTGCCTCG ACTCTCCCCC ACCGACTAGA AAGGTCCGTG AGAGCAAGGA    9600

GCAAGCCTGT CTTGTTTGAG GGCACTGGTT CTCATAGAGC CACAGGGAAT GATGCCCCTG    9660

GACTAAGCAG TGTGGGGTCT GCTGGCTTGC ACCTGTGCCC CCAGCTCCTA GCCAAAGACC    9720

AGACACATGT TGGGAACTCA ATACTTGTTT GTTTAATGAG TAGATGAACA AAAGCACTCA    9780

TGAAATAGGC AGTGCACGTA TCTTTATCAC CATTTGAAAG CTGAGGAAAC AGGCTTGGAG    9840

AGGGAAGCAA CTTGCCTGAC ACCCCAAATC ACAGAAGCAG CATATTTGGC CCAAGAACCT    9900

GGCTTCCTGT CTCCAAGGGG TCAGGTCCAG CTGGCATTGG CCTGTAGGCA TGTGAGTGTG    9960

GCAAGGTAGT CAGCAAAGAG CCTTTACTGC ATGTTGGGGT CAGAAGATCA GCAATAAGGA   10020

GGACAAAATC CTTGCCTGGA AGGAGCTTGT GTTCCAAAAA GAACAAGAGA CCACAGCATA   10080

TTCATTAATA AAGACACATT CAAACAGGGC CAAGTGCTCT GAAGCACCTC AGACAAAGCG   10140

ACAGGCTGCA AAATGACAGC GTTTGGGGGT CAGGAGACAG AAGGGTGCCT GCTTTAGGTG   10200

GTCGAAGAAG GCCTCTCTGG GGAGGTGGCA TTTGGTCTGA GACCTCAGGG CCAATGTGCT   10260

AGGAGCAGAG GAGCCTTGGG GAAGAATGGA GATGAGGTTG GACAGGATGA GACACGTGCC   10320
```

```
TTCTATGTCA ATGGCAAGGG AGTCATTGGA GCATGTGAAG CAGAGGATGC TCTACTTTTG     10380

CCCCAGAAAG ATCACTCTGG CTACAGTGCA GAGAAAGAAG AGAGTCAAGG AGGAAAGAAG     10440

GGCCTCATTA GGGGACTGTT GCAAAGCACA GGGAGGCACA ACCACAGCCA AGATCAGCAT     10500

GGTGACCAAT GGATGGAAGT GTCAGATGTC GCATGCTGTC GGTAGGTCAG GGCCGACAGG     10560

ACCTGTCGAT GGGTTCAGCG TGGGGTGTGA AGGAACACAG GCTGCACCCC AGCTCCTGGC     10620

CTGAGTGGCT GTAGATAGTG GCACCAAATA CTGAGCTCGT GAAGATGGGG GAGAGCTGAT     10680

GATGAAGACA GCAAGAGTTT GGTGTGAGTC ACCTTGAGTT TGAGACACGT GTCAGACATG     10740

TAAGGGGTAG GCAGGTGGAC ACGTGCTTAT TGAAGTCTGG AGCCAAGGGA GAGGTGTGGG     10800

CTGCAGCGGA GAAGTTGGGA GTATTCAGAG TTCTGACACT GACCAAGAAC ACCCCTCAGA     10860

GAATTCAGAG ACAACCAGGG CTGAGGCGAG GGGCTTAGAC TGGGGCCTGG GACAGCCACA     10920

GGCAGGAATG CAGACTTGCT GCCTCTTCTT ATTTGTGGAG ATGTAGTTCA TGCAGCAAGA     10980

AAGTCATTCC AAAGCCCTCC TTTCCTTTCT TCATGCCTCA GTTTCTCCAT TAGCACATTA     11040

AAAGATGCAA GATCTGGAGT TAAGCTTGTT TTTAAAAGGT GGCCTCCAAA GACGGTTTTT     11100

CTTGGCCTGG GGCTGTCTCA TCATCCAGGT CATGACAGGC CCGGTCCATG GTTGAGGAAT     11160

GCCACAGAAG TGACAGTCCA CTGCAAAAGA CTGCTGCTCC AGATCAGTTC TGGAAGGCCT     11220

GGCAATGGGG CAGGCCACTG AAGTAGAACT GGATGTCAGA TGCACGCATT AGAAAGGACA     11280

GGAAGACCAA ATGAGAAAGG GAGAGGGGGC AGGGAGAAAG GAAGGAGAGC TAGAGACTTG     11340

AGGCAAAGGA AACAAGAGAT GGAATAGAAG AAGACAGAGG ACCAGAAGAC AGTGAGACCA     11400

ACAGAAAGAG AGAGGGACGA GAAAGAAGGT GGCTGAGGAA GGTGAGAAAA GTGTTTCCAG     11460

GGCGACAGCA ACTGGACCAG GCCCTCTAGT TGGACAGTGA GGCTGGCTGG GGGGCCTGAG     11520

CTCAAGTAGC CCTCGTCCCC TGAGAGAGTG GGGGCTACCT GGGGAGCTGG GCTTGATGCA     11580

TCTGGAAGGA TCTTCACAGA GGCAGGAGGG GGAGTGGGAG GGCAGAGGGC ACCCAGGCGC     11640

TAGAACAGTG GGAGTGGCGG GACGCAAAAC CGGAGAGCCA GAGGAGTGAA CATCCCTGGC     11700

AGATTCCCCT GCGGCCGAGC AGGAGGGCAG GAAGCTCAGT GGTGTTGGCA CAACGTGAGA     11760

AGTTCCAGGG AGGCGTGGGA GGACGGCTTC TGCAGGACGC AGACTTTGCA GAGGGAGAGT     11820

GGCAAACAGA CTGACTGCAG GCAGCTCTGC CGGCTCCACA GGGCGCTGCT TTTTCTCCAC     11880

GGTGGAGCTG GAGTGCATCA CCCTGAGAAC CAGCAGCAAG CCCCCACAGG GCACCTTCTG     11940

CGTGCCAGGC ACATCCGGAC CACTTGTCGG TAGACACCAG TGACCCTCAC CACCACCCCA     12000

GGAATGGGAC AGTGTCATGT GTTTCTGAAA TGACTAGGTT TTAGCACCAT TTCATAGATG     12060

AGGAAGCTGA AGCTAACTTG CCCAAGGTCA TAAACCGGGC GTCTGGTGGC CTCCCCTCCT     12120

CACTGCCAAC CCTGAGAGCG GACTAGGGTG GAGTTATCTG GAAAGAGGAA GCTGTACCTG     12180

AGAGCCCTAA ACACACATGC GCGCGCACGA CACACACACA CGCACAAACA CACAATGCAC     12240

GCACACACAT GCGCACGCAC ATACACACAC ATGCACACAT GGACACATAC CTGCACACAC     12300

AAGCATACAC ATGCACACAG GCACACGCAT GCACACACGC GCATGCACAC ACATGCACAC     12360

ACATGTGCAT GCACACAGTG CGACAGCTCT GATTAGTAGG TAAATAAAAG GTTCCCATCT     12420

AGTGGTGACT CGGCCAAAGT GCAGACACTG AACCCCAAAG GCCCATAGAG GCTTCATTCA     12480

TCCCTTCTCT TATTCTTCAT TCATGGATTC TATTGAGCAT CTGCTCTGTG CAGCATCTGT     12540

CCTGGATGCT GGGGATACTG TGATGACTTA GACAAGGTCT CAGCCGCACA CAGCTTATGC     12600

TTCTTTGAGG GGAGGCAGAC ACAAGCCAGG AAACCAATAA GAGAAGTTAA GTAAAAAGCA     12660

CAGTGAGTGA GACAAACGGG TACGGAGGAC ATGGCCAGAG AGAGCTTTAG TTCAGGTGGT     12720
```

```
CAGGGAGCAC CTCTCTGAGG AGGTGAAATT TGACCAAGCC TCAAACAGTG GCAGGGATCC    12780

CACTGCTTGC AGATCCTGGG GAGAAGCATT TTAGACAAAA AGAACAGCAA GTCCAAAGGC    12840

CCAGAGACAA GACAGAGCAA GACCTGTGAC ATGAAACAGG CTGGTGTGCC CAGAGCAGGG    12900

AGGCTGGGAG AGTGGAGGGG GAGGGCGATG AGGGTGGAGA AGCTGGTGAG GGTGGCATCC    12960

CGGCAAGTGT GCCTGGCCAC GGAGGCCACG GAAGGATTCA GCATGTCTTT CCCGAATAGG    13020

AACCACACTG GGCTGTAACA GAGAGTGACG TACTCGGTAC GTTGAGAAGG TCCTGCTTAT    13080

TTCCTTCCGT GAAGGAGGAA GAGCTGCTGA TGACAGAGAT TGGCAGTGGC CAAAGACATA    13140

GAGAGAAGAG GGCAGAACAT GGGCTATTTT AAACACAGAG AAGATTAGCG GGACCCGCTG    13200

GCAGACCGGA CGTGAAATGT GGAAGGAGCG GGGGCAGCGA GGTCGGCTCC TAGTTTCCTG    13260

AGAATGTGGG TGAATCACGG GCTCACAGGC AGAGGGAGCA CTAGGATATC AAGGGTTCCC    13320

TTGTGAACGC CTCAAGTTGG AGATGCCTGA GACATCCAAG TGAGATGTCA AGCAGGCAGC    13380

TGGAAATAGG AGATGAGCTC TGGGAAAATG CTCCCATCAC CCTGGCCTGT GTGCTGCCTG    13440

GGCGCACCCA TTCAGGGCCC TCCACGCAGC CCACGCCCCT GCCTCCTGAT TCCTTCTAGG    13500

CTTCTCCAGC ACTCGTGGGA TGCCCAGATG TGATCAGGGA AGGGCTTGAG GATGCAGGGA    13560

AGCTGTGGCT GAGAGCCCTA AACACACACA TGCACACGCA CACACACATA CACAGGCACA    13620

TGCACACACG ACCATACACA CACACAAATG CACGCAGATG CACACAAATG CATATGCACG    13680

CACACAAATG CATATGCACA CACACACATG CACACATATG CATACACGTA TCCCTTTCAG    13740

TGGCTTTCCT TTCTGTCCTT AACCCTTGGC CCCTTACAGT GAGCTCCCAG TTCTCCCCAG    13800

CCTTAGAACC AAACCCTGGG GCTGGGCTGG GAGCCCCCAG TGACCCTCTG TGTCTCTGTA    13860

GGTGGATGCA CCCCTTGGTCC TGGTGCCAGC TGCCACTGCA GGCTGAAGGC CTGTGAGTGT    13920

GACAAGCAAT CCGTGCACTG CTTCAAAGAG AGCCTGCCCA CCTATGAGAA AAACTTCAAG    13980

CAGTTCTCCA GCCGGCCCAG GTGTGGCAGA CATAAGCCCT GGTGCTAGGG ACACCACAGG    14040

GTCCCTCTCA TCATCCAGCA TCCGCTCTAG TGTTGCTCTT CCAGGAAGCC TTCTCAGATC    14100

ATCCCCAACA GGCCCCTGTT CTTCCACTGG GAGGGAGGAC AAAATGTCTC CCGCAGGGCA    14160

GCTCACCCTT CAGCATTCTG ACCAAGGGGA CTCCCTGTCG TTCAGCATCA GAGGGCTGGA    14220

GAGCAGAAAT GGGAAAGATG AGATGCCTGC CCTGCAGGAG CTGGCATTCT GTGGAGTGGG    14280

GAGGACTACA AATGCATGGA TATAGAAGTA AGAGACACAT TAGACTGTAG TAAGTGCTAT    14340

GATGCAGTAA AACAAAGGGA CGGGATAGAG ATGCACCCAA CCCCACATCC CAGGGGTTTC    14400

CAGGAGGGGA GAAGCCCCAG GATCTACCCC AAACTCTCTC TTCACCCCCA CTGCAAACCG    14460

GGACACAGAG CAGACTTGAG CGCCAGGCCC ATGCCCAGCT CTAGCTGGCA ACAAAGCCAC    14520

CACTTTCCTT GCCCCTCTGC GTCCTCAGTT TTTATGATGT CATTCTTAGC TTTTCTTATC    14580

AAGAGGCAGA ATCTGTTTTC CCCATCCCAT GAATCTGAAC TGGTCTTGTG GCTTAGTTTG    14640

GTCAATAGAA TGTTGTGGGA GGGATGGTTT ACCAGTTTTG AGCTAGGCCT CAGGAGGTCT    14700

AGGGCATGTC TACTCTCTCT TAGGACAGCT GCCCCCACCC TGCAAAAAAG CCTGGGCTAG    14760

CCTGCTGGAG GATGAGAGCC CACCTGGATC AGTTGTCTCA GCTGATTTCA GACACGTGAG    14820

AGAGAGCTCA GCGAGACTCA GCTTGTAGCT GACTACAGAT GTGTGAGGGA ACCTGGCTGA    14880

GACCAAAACA ACTGTCCAGC TGAGCCCAGG CTAAACTGCC AACATGCAGA ATTGTGAGCT    14940

AAATAAAGGC TGCTGTTCTA AGTCACTGGG TTTTGGTATG GTTTGTTAGG CAGCCATAAC    15000

TAACAGGTGT AATTGGTCCT TATTCCCTTA TTCACTGAGA GTGATGGGTT CTCAGCCCTG    15060

AGCTGGACTT GGAGGCCATG GAAATGCAGT GGACATGGCC TTTGTTCCTT ACCTTGAAGC    15120
```

```
TGTGGAAGGA GGTCAAGTTC ATGGAATAAT GGAGAACACA CAGCTGTAAT CGTTTGCTTG    15180

TTCAGGGAAC ACACATTTAT TGAGCACTTG CTATGTGCCA GGCACAGTGC CAGGCAGTAG    15240

GGATCCAGAT ATTTAAAGAA AACAAACAAA AATCAGGTCC AAAACTCCTG GGAGAATGC     15300

TGAGAGTGGT ATCAGCTTTT AGGAATTC                                       15328
```

(2) INFORMATION FOR SEQ ID NO:34:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:34:

```
Met Lys Leu Leu Leu Leu Ala Ala Leu Leu Thr Ala Gly Val Thr Ala
1               5                   10                  15

His Ser Ile Ser Thr Arg Ala Val Trp Gln Phe Arg Asn Met Ile Lys
                20                  25                  30

Cys Thr Ile Pro Gly Ser Asp Pro Leu Arg Glu Tyr Asn Asn Tyr Gly
            35                  40                  45

Cys Tyr Cys Gly Leu Gly Gly Ser Gly Thr Pro Val Asp Asp Leu Asp
        50                  55                  60

Arg Cys Cys Gln Thr His Asp His Cys Tyr Asn Gln Ala Lys Lys Leu
65                  70                  75                  80

Glu Ser Cys Lys Phe Leu Ile Asp Asn Pro Tyr Thr Asn Thr Tyr Ser
                85                  90                  95

Tyr Lys Cys Ser Gly Asn Val Ile Thr Cys Ser Asp Lys Asn Asn Asp
            100                 105                 110

Cys Glu Ser Phe Ile Cys Asn Cys Asp Arg Gln Ala Ala Ile Cys Phe
        115                 120                 125

Ser Lys Val Pro Tyr Asn Lys Glu Tyr Lys Asp Leu Asp Thr Lys Lys
    130                 135                 140

His Cys
145
```

(2) INFORMATION FOR SEQ ID NO:35:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:35:

```
Met Lys Val Leu Leu Leu Ala Val Val Ile Met Ala Phe Gly Ser
1               5                   10                  15

Ile Gln Val Gln Gly Ser Leu Leu Glu Phe Gly Gln Met Ile Leu Phe
                20                  25                  30

Lys Thr Gly Lys Arg Ala Asp Val Ser Tyr Gly Phe Tyr Gly Cys His
            35                  40                  45

Cys Gly Val Gly Gly Arg Gly Ser Pro Lys Asp Ala Thr Asp Trp Cys
        50                  55                  60

Cys Val Thr His Asp Cys Cys Tyr Asn Arg Leu Glu Lys Arg Gly Cys
65                  70                  75                  80

Gly Thr Lys Phe Val Thr Tyr Lys Phe Ser Tyr Arg Gly Gly Gln Ile
```

```
                    85                  90                  95
Ser Cys Ser Thr Asn Gln Asp Ser Cys Arg Lys Gln Leu Cys Gln Cys
                100                 105                 110

Asp Lys Ala Ala Ala Glu Cys Phe Ala Arg Asn Lys Lys Ser Tyr Ser
            115                 120                 125

Leu Lys Tyr Gln Phe Tyr Pro Asn Lys Phe Cys Lys Gly Lys Thr Pro
            130                 135                 140

Ser Cys
145

(2) INFORMATION FOR SEQ ID NO:36:

(i) SEQUENCE CHARACTERISTICS:
         (A) LENGTH: 148 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO:36:

Met Lys Leu Leu Val Leu Ala Val Leu Leu Thr Val Ala Ala Ala Asp
1               5                  10                  15

Ser Gly Ile Ser Pro Arg Ala Val Trp Gln Phe Arg Lys Met Ile Lys
            20                  25                  30

Cys Val Ile Pro Gly Ser Asp Pro Phe Leu Glu Tyr Asn Asn Tyr Gly
            35                  40                  45

Cys Tyr Cys Gly Leu Gly Gly Ser Gly Thr Pro Val Asp Glu Leu Asp
        50                  55                  60

Lys Cys Cys Gln Thr His Asp Asn Cys Tyr Asp Gln Ala Lys Lys Leu
65                  70                  75                  80

Asp Ser Cys Lys Phe Leu Leu Asp Asn Pro Tyr Thr His Thr Tyr Ser
                85                  90                  95

Tyr Ser Cys Ser Gly Ser Ala Ile Thr Cys Ser Ser Lys Asn Lys Glu
                100                 105                 110

Cys Glu Ala Phe Ile Cys Asn Cys Asp Arg Asn Ala Ala Ile Cys Phe
            115                 120                 125

Ser Lys Ala Pro Tyr Asn Lys Ala His Lys Asn Leu Asp Thr Lys Lys
            130                 135                 140

Tyr Cys Gln Ser
145

(2) INFORMATION FOR SEQ ID NO:37:

(i) SEQUENCE CHARACTERISTICS:
         (A) LENGTH: 144 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO:37:

Met Lys Thr Leu Leu Leu Ala Val Ile Met Ile Phe Gly Leu Leu Leu
1               5                  10                  15

Gln Ala His Gly Asn Leu Val Asn Phe His Arg Met Ile Lys Leu Thr
            20                  25                  30

Thr Gly Lys Glu Ala Ala Leu Ser Tyr Gly Phe Tyr Gly Cys His Cys
            35                  40                  45

Gly Val Gly Gly Arg Gly Ser Pro Lys Asp Ala Thr Asp Arg Cys Cys
```

```
            50                  55                  60
Val Thr His Asp Cys Cys Tyr Lys Arg Leu Glu Lys Arg Gly Cys Gly
 65                  70                  75                  80

Thr Lys Phe Leu Ser Tyr Lys Phe Ser Asn Ser Gly Ser Arg Ile Thr
                 85                  90                  95

Cys Ala Lys Gln Asp Ser Cys Arg Ser Gln Leu Cys Glu Cys Asp Lys
            100                 105                 110

Ala Ala Ala Thr Cys Phe Ala Arg Asn Lys Thr Thr Tyr Asn Lys Lys
        115                 120                 125

Tyr Gln Tyr Tyr Ser Asn Lys His Cys Arg Gly Ser Thr Pro Arg Cys
    130                 135                 140
```

(2) INFORMATION FOR SEQ ID NO:38:

(i) SEQUENCE CHARACTERISTICS:
        (A) LENGTH: 126 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:38:

```
Ala Val Trp Gln Phe Arg Lys Met Ile Lys Cys Val Ile Pro Gly Ser
 1               5                  10                  15

Asp Pro Phe Leu Glu Tyr Asn Asn Tyr Gly Cys Tyr Cys Gly Leu Gly
                20                  25                  30

Gly Ser Gly Thr Pro Val Asp Glu Leu Asp Lys Cys Cys Gln Thr His
            35                  40                  45

Asp Asn Cys Tyr Asp Gln Ala Lys Lys Leu Asp Ser Cys Lys Phe Leu
    50                  55                  60

Leu Asp Asn Pro Tyr Thr His Thr Tyr Ser Tyr Ser Cys Ser Gly Ser
 65                  70                  75                  80

Ala Ile Thr Cys Ser Ser Lys Asn Lys Glu Cys Glu Ala Phe Ile Cys
                85                  90                  95

Asn Cys Asp Arg Asn Ala Ala Ile Cys Phe Ser Lys Ala Pro Tyr Asn
            100                 105                 110

Lys Ala His Lys Asn Leu Asp Thr Lys Lys Tyr Cys Gln Ser
        115                 120                 125
```

(2) INFORMATION FOR SEQ ID NO:39:

(i) SEQUENCE CHARACTERISTICS:
    (A) LENGTH: 124 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:39:

```
Asn Leu Val Asn Phe His Arg Met Ile Lys Leu Thr Thr Gly Lys Glu
 1               5                  10                  15

Ala Ala Leu Ser Tyr Gly Phe Tyr Gly Cys His Cys Gly Val Gly Gly
                20                  25                  30

Arg Gly Ser Pro Lys Asp Ala Thr Asp Arg Cys Cys Val Thr His Asp
            35                  40                  45

Cys Cys Tyr Lys Arg Leu Glu Lys Arg Gly Cys Gly Thr Lys Phe Leu
    50                  55                  60

Ser Tyr Lys Phe Ser Asn Ser Gly Ser Arg Ile Thr Cys Ala Lys Gln
```

```
                65                  70                  75                  80
Asp Ser Cys Arg Ser Gln Leu Cys Glu Cys Asp Lys Ala Ala Thr
                    85                  90                  95
Cys Phe Ala Arg Asn Lys Thr Thr Tyr Asn Lys Lys Tyr Gln Tyr Tyr
                100                 105                 110
Ser Asn Lys His Cys Arg Gly Ser Thr Pro Arg Cys
                115                 120
```

(2) INFORMATION FOR SEQ ID NO:40:

(i) SEQUENCE CHARACTERISTICS:
       (A) LENGTH: 118 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:40:

```
Gly Leu Leu Asp Leu Lys Ser Met Ile Glu Lys Val Thr Gly Lys Asn
1               5                   10                  15
Ala Leu Thr Asn Tyr Gly Phe Tyr Gly Cys Tyr Cys Gly Trp Gly Gly
                20                  25                  30
Arg Gly Thr Pro Lys Asp Gly Thr Asp Trp Cys Cys Trp Ala His Asp
            35                  40                  45
His Cys Tyr Gly Arg Leu Glu Glu Lys Gly Cys Asn Ile Arg Thr Gln
        50                  55                  60
Ser Tyr Lys Tyr Arg Phe Ala Trp Gly Val Val Thr Cys Glu Pro Gly
65                  70                  75                  80
Pro Phe Cys His Val Asn Leu Cys Ala Cys Asp Arg Lys Leu Val Tyr
                85                  90                  95
Cys Leu Lys Arg Asn Leu Arg Ser Tyr Asn Pro Gln Tyr Gln Tyr Phe
                100                 105                 110
Pro Asn Ile Leu Cys Ser
            115
```

(2) INFORMATION FOR SEQ ID NO:41:

(i) SEQUENCE CHARACTERISTICS:
       (A) LENGTH: 124 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:41:

```
Ala Val Trp Gln Phe Arg Asn Met Ile Lys Cys Thr Ile Pro Gly Ser
1               5                   10                  15
Asp Pro Leu Arg Glu Tyr Asn Asn Tyr Gly Cys Tyr Cys Gly Leu Gly
                20                  25                  30
Gly Ser Gly Thr Pro Val Asp Asp Leu Asp Arg Cys Cys Gln Thr His
            35                  40                  45
Asp His Cys Tyr Asn Gln Ala Lys Lys Leu Glu Ser Cys Lys Phe Leu
        50                  55                  60
Ile Asp Asn Pro Tyr Thr Asn Thr Tyr Ser Tyr Lys Cys Ser Gly Asn
65                  70                  75                  80
Val Ile Thr Cys Ser Asp Lys Asn Asn Asp Cys Glu Ser Phe Ile Cys
                85                  90                  95
Asn Cys Asp Arg Gln Ala Ala Ile Cys Phe Ser Lys Val Pro Tyr Asn
```

```
                    100                 105                 110
Lys Glu Tyr Lys Asp Leu Asp Thr Lys Lys His Cys
            115                 120

(2) INFORMATION FOR SEQ ID NO:42:

(i) SEQUENCE CHARACTERISTICS:
        (A) LENGTH: 125 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:42:

Ser Leu Leu Glu Phe Gly Gln Met Ile Leu Phe Lys Thr Gly Lys Arg
1               5                   10                  15

Ala Asp Val Ser Tyr Gly Phe Tyr Gly Cys His Cys Gly Val Gly Gly
            20                  25                  30

Arg Gly Ser Pro Lys Asp Ala Thr Asp Trp Cys Cys Val Thr His Asp
        35                  40                  45

Cys Cys Tyr Asn Arg Leu Glu Lys Arg Gly Cys Gly Thr Lys Phe Val
50                  55                  60

Thr Tyr Lys Phe Ser Tyr Arg Gly Gly Gln Ile Ser Cys Ser Thr Asn
65                  70                  75                  80

Gln Asp Ser Cys Arg Lys Gln Leu Cys Gln Cys Asp Lys Ala Ala Ala
            85                  90                  95

Glu Cys Phe Ala Arg Asn Lys Lys Ser Tyr Ser Leu Lys Tyr Gln Phe
            100                 105                 110

Tyr Pro Asn Lys Phe Cys Lys Gly Lys Thr Pro Ser Cys
            115                 120                 125

(2) INFORMATION FOR SEQ ID NO:43:

(i) SEQUENCE CHARACTERISTICS:
        (A) LENGTH: 130 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:43:

Ser Phe Trp Gln Phe Gln Arg Met Val Lys His Ile Thr Gly Arg Ser
1               5                   10                  15

Ala Phe Phe Ser Tyr Tyr Gly Tyr Gly Cys Tyr Cys Gly Leu Gly Gly
            20                  25                  30

Arg Gly Ile Pro Val Asp Ala Thr Asp Arg Cys Cys Trp Ala His Asp
        35                  40                  45

Cys Cys Tyr His Lys Leu Lys Glu Tyr Gly Cys Gln Pro Ile Leu Asn
50                  55                  60

Ala Tyr Gln Phe Ala Ile Val Asn Gly Thr Val Thr Cys Gly Cys Thr
65                  70                  75                  80

Met Gly Gly Gly Cys Leu Cys Gly Gln Lys Ala Cys Glu Cys Asp Lys
            85                  90                  95

Leu Ser Val Tyr Cys Phe Lys Glu Asn Leu Ala Thr Tyr Glu Lys Thr
            100                 105                 110

Phe Lys Gln Leu Phe Pro Thr Arg Pro Gln Cys Gly Arg Asp Lys Leu
            115                 120                 125

His Cys
```

130

(2) INFORMATION FOR SEQ ID NO:44:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:44:

```
Gly Leu Leu Glu Leu Lys Ser Met Ile Glu Lys Val Thr Gly Lys Asn
 1               5                  10                  15

Ala Val Lys Asn Tyr Gly Phe Tyr Gly Cys Tyr Cys Gly Trp Gly Gly
                20                  25                  30

His Gly Thr Pro Lys Asp Gly Thr Asp Trp Cys Cys Arg Met His Asp
            35                  40                  45

Arg Cys Tyr Gly Leu Leu Glu Glu Lys His Cys Ala Ile Arg Thr Gln
50                      55                  60

Ser Tyr Asp Tyr Arg Phe Thr Gln Asp Leu Val Ile Cys Glu His Asp
65                  70                  75                  80

Ser Phe Cys Pro Val Arg Leu Cys Ala Cys Asp Arg Lys Leu Val Tyr
                85                  90                  95

Cys Leu Arg Arg Asn Leu Trp Ser Tyr Asn Arg Leu Tyr Gln Tyr Tyr
             100                 105                 110

Pro Asn Phe Leu Cys
            115
```